(12) United States Patent
Attias et al.

(10) Patent No.: US 12,163,120 B2
(45) Date of Patent: Dec. 10, 2024

(54) MYCELIUM-CONTAINING HYBRID MATERIALS

(71) Applicant: Technion Research & Development Foundation Limited, Haifa (IL)

(72) Inventors: Noam Attias, Haifa (IL); Jacob Grobman, Haifa (IL); Tiffany Abitbol, Stockholm (SE)

(73) Assignee: Technion Research & Development Foundation Limited, Haifa (IL)

( * ) Notice: Subject to any disclaimer, the term of this patent is extended or adjusted under 35 U.S.C. 154(b) by 132 days.

(21) Appl. No.: 17/471,311

(22) Filed: Sep. 10, 2021

(65) Prior Publication Data

US 2022/0073865 A1 Mar. 10, 2022

Related U.S. Application Data

(60) Provisional application No. 63/076,490, filed on Sep. 10, 2020.

(51) Int. Cl.
*C12N 1/14* (2006.01)
*C08L 1/04* (2006.01)

(52) U.S. Cl.
CPC . *C12N 1/14* (2013.01); *C08L 1/04* (2013.01)

(58) Field of Classification Search
CPC .. C12N 1/14; C12N 1/22; B32B 9/046; C08L 1/04; A01G 18/20
USPC ..... 435/254.1, 256.8, 244, 252; 106/163.01; 977/902
See application file for complete search history.

(56) References Cited

U.S. PATENT DOCUMENTS

| 2011/0268955 A1 | 11/2011 | Rocco et al. |
| 2016/0264926 A1* | 9/2016 | Winiski ................. C12N 1/22 |
| 2017/0218327 A1 | 8/2017 | Amstislavski et al. |
| 2019/0090436 A1 | 3/2019 | Betts et al. |

FOREIGN PATENT DOCUMENTS

WO WO 2019/170355 9/2019

OTHER PUBLICATIONS

Rowell, Roger M.; Pettersen, Roger; Tshabalala, Mandla A. 2013. Cell wall chemistry. In: Rowell, Roger. ed. Handbook of wood chemistry and wood composites, Second edition. Boca Raton, FL: CRC Press: 33-72. Chapter 3 (Year: 2013).*

(Continued)

*Primary Examiner* — Stefanie J Cohen
*Assistant Examiner* — Ritu S Shirali

(57) ABSTRACT

A method of preparing a composition comprising mycelium along with a cellulose and/or plurality of nanoparticles is described herein. The method comprises inoculating a liquid medium with fungus, the liquid medium comprising nutrients and the cellulose and/or nanoparticles. Further described herein are compositions comprising mycelium along with a cellulose and/or plurality of nanoparticles, as well as articles-of-manufacture comprising such a composition, wherein at least 10% of the cellulose and/or nanoparticles in the composition is incorporated within the mycelium. A method of enhancing fungal growth is also described, comprising contacting the fungus with a liquid medium comprising a polymer which comprises carboxylic acid groups.

10 Claims, 36 Drawing Sheets
(7 of 36 Drawing Sheet(s) Filed in Color)

(56) References Cited

OTHER PUBLICATIONS

Machine translation of WO 2019170355 A1 originally published Sep. 2019 to Schwarze et al. (Year: 2019).*
Alfaro et al. "Glucose Counteracts Wood-Dependent Induction of Lignocellulolytic Enzyme Secretion in Monokaryon and Dikaryon Submerged Cultures of the White-Rot Basidiomycete Pleurotus Ostreatus", Scientific Reports, 10(1): 12421-1-12421-10, Jul. 24, 2020.
Appels et al. "Fungal Mycelium Classified in Different Material Families Based on Glycerol Treatment", Communications Biology, 3(1): 334-1-334-5, Jun. 26, 2020.
Appels et al. "Hydrophobin Gene Deletion and Environmental Growth Conditions Impact Mechanical Properties of Mycelium by Affecting the Density of the Material", Scientific Reports, 8(1): 4703-1-4703-7, Published Online Mar. 16, 2018.
Attias et al. "Mycelium Bio-Composites in Industrial Design and Architecture: Comparative Review and Experimental Analysis", Journal of Cleaner Production, 246: 119037-1-119037-45, Feb. 10, 2020.
Bowman et al. "The Structure and Synthesis of the Fungal Cell Wall", BioEssays, 28(8): 799-808, Aug. 2006.
Ferrer et al. "Nanocellulose in Packaging: Advances in Barrier Layer Technologies", Industrial Crops and Products, 95: 574-582, Jan. 1, 2017.
Girometta et al. "Physico-Mechanical and ThermodynamikProperties of Mycelium-Based Biocomposites: A Review", Sustainability, 11(1): 281-1-281-22, Jan. 8, 2019.
Grimm et al. "Mushroom Cultivation in the Circular Economy", Applied Microbiology and Biotechnology, 102(18): 7795-7803, Published Online Jul. 19, 2018.
Haneef et al. "Advanced Materials From Fungal Mycelium: Fabrication and Tuning of Physical Properties", Scientific Reports, 7: 41292-1-41292-11, Jan. 24, 2017.
Isogai "Wood Nanocelluloses: Fundamentals and Applications as New Bio-Based Nanomaterials", Journal of Wood Science, 59(6): 449-459, Published Online Sep. 18, 2013.
Jones et al. "Waste-Derived Low-Cost Mycelium Nanopapers With Tunable Mechanical and Surface Properties", BioMacromolecules, 20(9): 3513-3523, Published Online Jul. 29, 2019.
Kang et al. "Molecular Architecture of Fungal Cell Walls Revealed by Solid-State NMR", Nature Communications, 9(1): 2747-1-2747-12, Jul. 16, 2018.
Moon et al. "Cellulose Nanomaterials Rview: Structure, Properties and Nanocomposites", Chemical Society Reviews, 40(7): 3941-3994, Published Online May 12, 2011.
Nawawi et al. "Plastic to Elastic: Fungi Derived Composite Nanopapers With Tunable Tensile Properties", Composites Science and Technology, 198: 108327-1-108327-8, Sep. 29, 2020.
Okal et al. "Mini Review: Advances in Understanding Regulation of Cellulase Enzyme in White-Rot Basidiomycetes", Microbial Pathogenesis, 147: 104410-1-104410-23, Published Online Jul. 21, 2020.
Papagianni "Fungal Morphology and Metabolic Production in Submerged Mycelial Processes", Biotechnology Advances, 22(3): 189-259, Jan. 2004.
Reid et al. "Benchmarking Cellulose Nanocrystals: From the Laboratory to Industrial Production", Langmuir, 33(7): 1583-1598, Published Online Dec. 1, 2016.
Ruiz-Herrera et al. "Cell Wall Glucans of Fungi. A Review", The Cell Surface, 5: 100022-1-100022-14, Mar. 21, 2019.
Sun et al. "Fully Bio-Based Hybrid Composites Made of Wood, Fungal Mycelium and Cellulose Nanofibrils", Scientific Reports, 9(1): 3766-1-376612, Published Online Mar. 6, 2019.

* cited by examiner

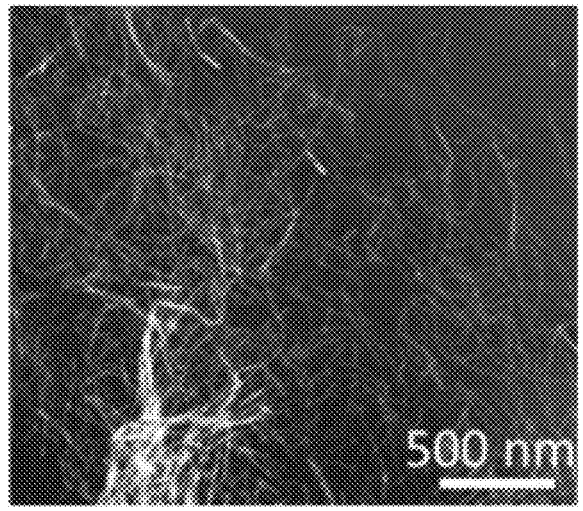
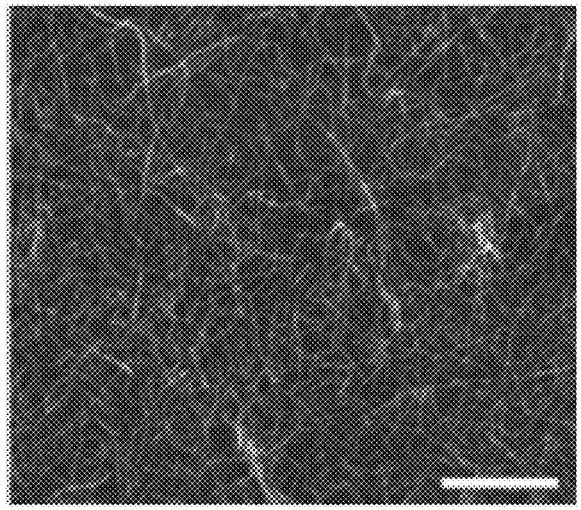
FIG. 1A
FIG. 1B
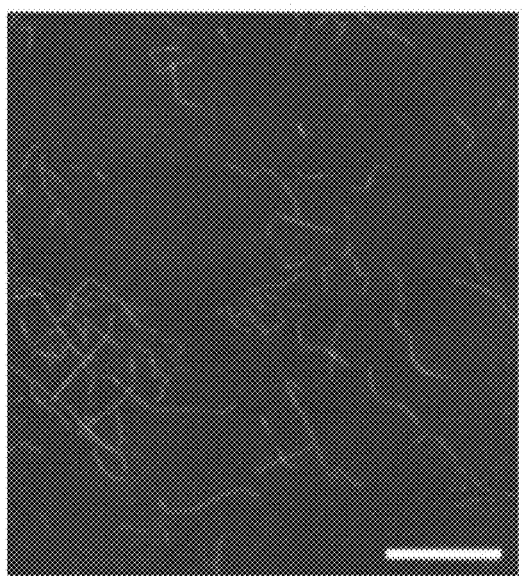
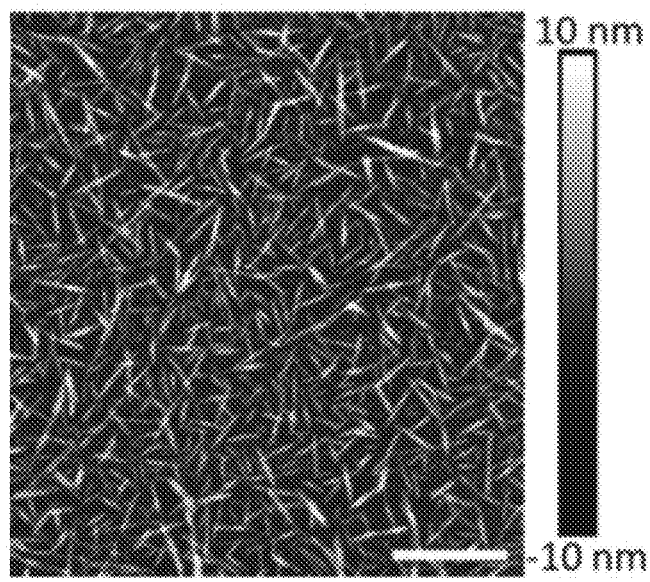
FIG. 1C
FIG. 1D

MYCELIUM-CONTAINING HYBRID MATERIALS

RELATED APPLICATION(S)

This application claims the benefit of priority under 35 USC § 119(e) of U.S. Provisional Patent Application No. 63/076,490 filed on Sep. 10, 2020, the contents of which are all incorporated by reference as if fully set forth herein in their entirety.

FIELD AND BACKGROUND OF THE INVENTION

The present invention, in some embodiments thereof, relates to materials, and more particularly, but not exclusively, to composite (hybrid) materials that comprise mycelium in combination with plant-derived substances or synthetic analogs thereof, such as, for example, cellulose and/or cellulose-based materials.

Two emerging forest-based materials, fungal mycelium and nanocellulose, are exceptionally promising as they can be processed into a versatile range of sustainable alternatives, such as packaging, flame-retardants, and substitutes for meat and leather.

Most fungi form continuous, filamentous multicellular structures called hyphae, which branch, fuse, and extend to produce the complex three-dimensional network known as mycelium. The fungal cell wall is composed of a dynamic and heterogeneous interwoven mesh of chitin, glucans, glycoproteins, and other polysaccharides [Bowman & Free, BioEssays 2006, 28:799-808; Kang et al., Nat Commun 2018, 9:2747], creating interconnected layers, which together provide the properties required to withstand high internal hydraulic pressures, provide physical protection, and maintain internal humidity. These properties play an important role when mycelium is employed as a structural material.

In nature, white-rot fungi mycelium develops on wood, dispersing within and around it, preferentially decomposing lignin while leaving much of the cellulose intact. Industrially, mycelium may be grown in submerged culture, forming macroscopic hyphal aggregates, which are then processed to extract different microbial products [Papagianni, Biotechnol Adv 2004, 22:189-259]. Mycelium development is accompanied by the secretion of exopolysaccharides and various proteins, including hydrophobins. White-rot fungi express lignocellulose-degrading enzymes under specific conditions, but the activity of these enzymes can be suppressed by the addition of easily digestible simple sugars or other nutrients into the growth medium [Alfaro et al., Sci Rep 2020. 10:12421; Okal et al., Microb Pathog 2020, 147:104410].

In recent years, the use of white-rot fungi to produce composite materials has been investigated. For example, U.S. Patent Application Publication No. 2019/0090436 describes a flexible substrate of fibrous material with mycelial tissue enmeshed with the substrate, which may be used to form rigid products upon being subjected to heat and pressure in molds.

Different fungal species, substrates, and approaches have been used to produce bio-composites with distinct properties. Space-filling composites produced from the solid-state cultivation of *Trametes versicolor, Trametes ochracea*, or *G. sessile* with various substrates from agricultural waste presented different characteristics depending on the fungus-substrate combination [Attias et al., J Clean Prod 2019, 119037]. Films from *G. licidum* or *Pleuroius ostreatus* were stiffer when grown from a feeding substrate composed of microcrystalline cellulose (MCC) than of a mixture of MCC and easier to digest potato dextrose broth [Haneef et al., Sci Rep 2017, 7:41292].

The term nanocellulose (NC) includes cellulose nanocrystals (CNCs), cellulose nanofibrils (CNFs), microfibrillated cellulose (MFC), and bacterial nanocellulose (BNC). NC may be derived from wood, or from other natural cellulose sources, including waste streams and may be processed from feedstocks of different purity and composition (lignin, hemicellulose, pectin). CNCs and CNFs are the highly crystalline cellulosic structural building blocks of the plant cell wall, with CNFs being liberated by mechanical delamination and CNCs by chemical degradation [Isogai, J Wood Sci 2013, 59:449-459]. CNCs are comparatively short and monodisperse (~100 nm length and 5-10 nm width) [Reid et al., Langmuir 2017, 33:1583-1598]; whereas CNF sizes can vary significantly depending on pulp pretreatment and extent of fibrillation, with the finest grades usually produced from highly delaminated chemically modified pulps. Nanocellulose's mechanical properties and ability to form densely packed films make it a candidate for composite reinforcement and barrier applications [Moon et al., Chem Soc Rev 2011, 40:3941-3944; Ferrer et al., Ind Crops Prod 2017, 95:574-582].

Sun et al. [Sci Rep 2019, 9:3766] describe composites based on wood and mycelium, with cellulose nanofibrils (CNFs) added as a binder; and reports that growing mycelium on the wood and then adding CNFs resulted in enhanced physical and mechanical properties, such as reduced water absorption, as compared with physically mixing wood, mycelium and CNFs.

U.S. Patent Application Publication No. 2011/0268955 describes a method of forming a molded part using a mixture of a fungal inoculum and a liquid aggregate, with homogenously distributed nanoparticles, such as nanoclay, nanocarbon fiber or metallic nanoparticles. The mixture is inserted into a mold cavity and live mycelium is grown to fill the cavity.

Additional background art includes Appels et al. [Sci Rep 2018, 8:4703]; Appels et al. [Commun Biol 2020, 3:334]; Grimm & Wosten [Appl Microbiol Biotechnol 2018, 102: 7795-7803]; Jones et al. [Biomacromolecules 2019, 20:3513-3523]; Nawawi et al. [Compos Sci Technol 2020, 198:108327]; U.S. Patent Application Publication No. 2017/0218327; and International Patent Application Publication WO 2019/170355.

SUMMARY OF THE INVENTION

According to an aspect of some embodiments of the invention, there is provided a method of preparing a composition comprising mycelium of a fungus and a cellulose, the method comprising inoculating a liquid medium with the fungus, the liquid medium comprising nutrients and the cellulose, thereby obtaining the composition comprising the mycelium and the cellulose.

According to an aspect of some embodiments of the invention, there is provided a composition comprising mycelium and a cellulose, the composition being obtainable according to the method of preparing a composition comprising mycelium and a cellulose, according to any of the respective embodiments described herein.

According to an aspect of some embodiments of the invention, there is provided a composition comprising mycelium and a cellulose, wherein at least 10 weight percent of the cellulose is incorporated within the mycelium.

According to an aspect of some embodiments of the invention, there is provided a method of preparing a composition comprising mycelium of a fungus and a plurality of nanoparticles, the method comprising inoculating a liquid medium with the fungus, the liquid medium comprising nutrients and the nanoparticles, thereby obtaining the composition comprising the mycelium and the nanoparticles.

According to an aspect of some embodiments of the invention, there is provided a composition comprising mycelium and a plurality of nanoparticles, the composition being obtainable according to the method of preparing a composition comprising mycelium and a plurality of nanoparticles, according to any of the respective embodiments described herein.

According to an aspect of some embodiments of the invention, there is provided a composition comprising mycelium and a plurality of nanoparticles, wherein at least 10 weight percent of the nanoparticles is incorporated within the mycelium.

According to an aspect of some embodiments of the invention, there is provided an article-of-manufacture comprising a composition according to any of the respective embodiments described herein.

According to an aspect of some embodiments of the invention, there is provided a method of enhancing growth of a fungus, the method comprising contacting the fungus with a liquid medium comprising a polymer which comprises carboxylic acid groups.

According to some of any of the respective embodiments described herein, the nutrients comprise at least one monosaccharide.

According to some of any of the respective embodiments described herein, the nutrients suppress cellulase activity of the fungus.

According to some of any of the respective embodiments described herein, the cellulose comprises nanocellulose.

According to some of any of the respective embodiments described herein, an initial concentration of the cellulose in the liquid medium is in a range of from 0.05 weight percent to 5 weight percent.

According to some of any of the respective embodiments described herein, an initial concentration of the nanoparticles in the liquid medium is in a range of from 0.05 weight percent to 5 weight percent.

According to some of any of the embodiments described herein relating to a method preparing a composition comprising mycelium, the method further comprises homogenizing the mycelium so as to obtain a homogenized composition comprising the mycelium and cellulose.

According to some of any of the embodiments described herein relating to a method preparing a composition comprising mycelium, the method further comprises homogenizing the mycelium so as to obtain a homogenized composition comprising the mycelium and nanoparticles.

According to some of any of the respective embodiments described herein, the composition is in a form of a layer or a porous structure.

According to some of any of the respective embodiments described herein, the cellulose incorporated within the mycelium comprises at least 10% of the total dry weight of the mycelium and the cellulose incorporated within the mycelium.

According to some of any of the respective embodiments described herein, the nanoparticles incorporated within the mycelium comprises at least 10% of the total dry weight of the mycelium and the nanoparticles incorporated within the mycelium.

According to some of any of the respective embodiments described herein, a water uptake of the composition is no more than 1000% of the dry weight of the composition.

According to some of any of the embodiments described herein relating to a method, a viscosity of the liquid medium is at least 10 cP.

According to some of any of the embodiments described herein relating to a method of enhancing growth of a fungus, the polymer comprises carboxymethylated cellulose.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1D present atomic force microscopy (AFM) height images of various types of nanocellulose: carboxymethylated cellulose nanofibrils (CNFs)—DS 0.1, 1p grade (FIG. 1A), carboxymethylated CNFs—DS 0.1, 4p grade (FIG. 1B), carboxymethylated CNFs—DS 0.3, 4p grade (FIG. 1C), and cellulose nanocrystals (FIG. 1D); DS represents degree of substitution by carboxymethyl, and p represents number of passes through a processor (at 1700 bar).

Figure 2A:
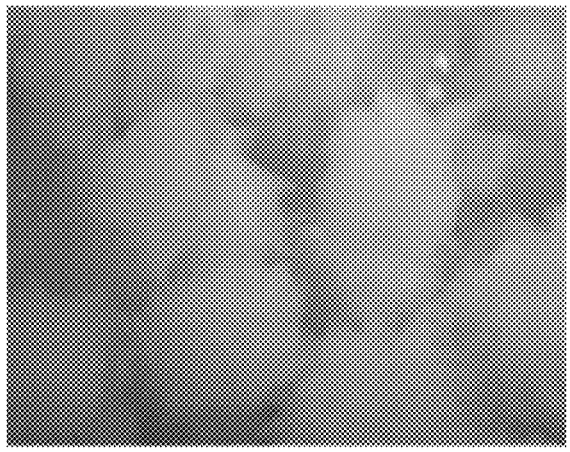
Figure 2B:
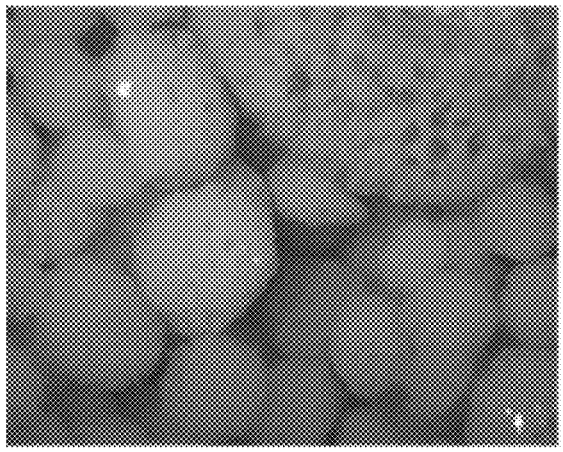
Figure 2C:
Figure 2D:
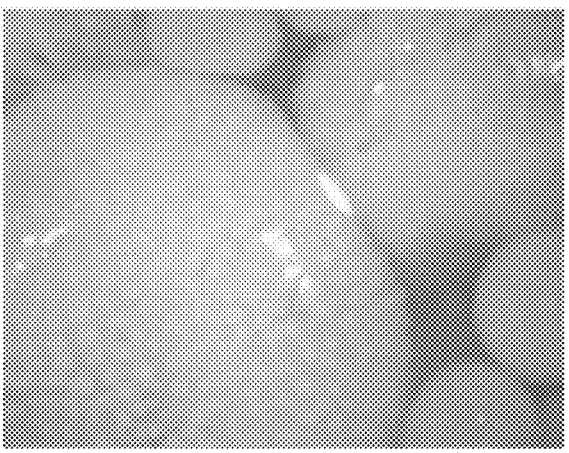
Figure 2E:
Figure 2F:
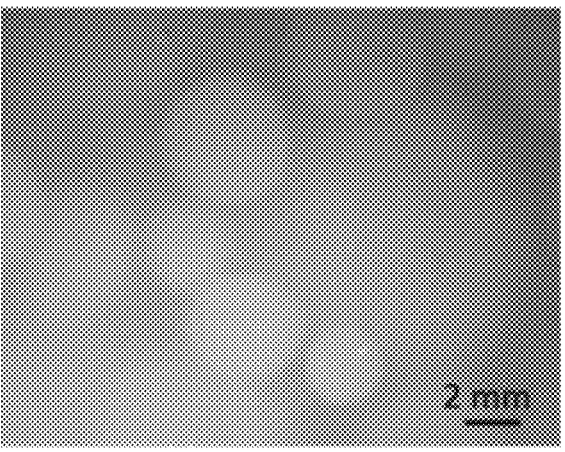

FIGS. 2A-2F present stereomicroscope images of autoclaved (1 hour at 121° C.) never-dried pellets showing different sizes and textures obtained through the co-incubation process, from round and smooth to rough with finger-like protrusions or sponge-like; pellets are obtained from pure *T. ochracea* (FIGS. 2A and 2B) and co-incubation of *T. ochracea* with 0.2% CNF DS 0.3, 4p grade) (FIG. 2C), 0.2% CNF DS 0.1, 1p grade (FIG. 2D), 0.2% CNF DS 0.1, 4p grade (FIG. 2E), and 0.5% CNF DS 0.1, 1p grade (FIG. 2F).

Figure 3A:
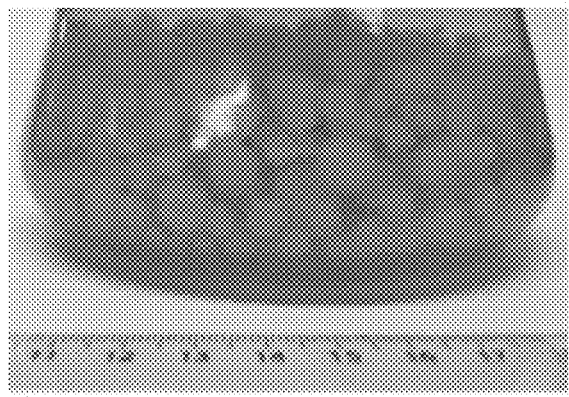
Figure 3B:
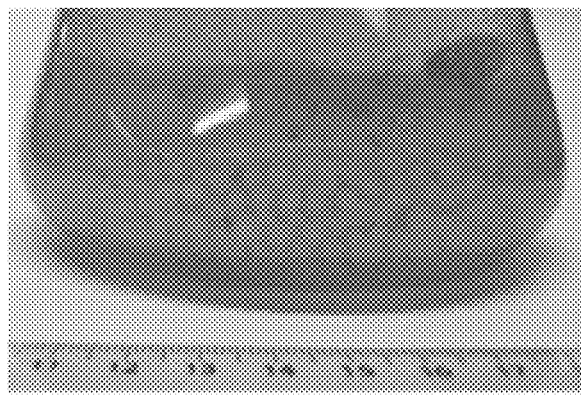
Figure 3C:
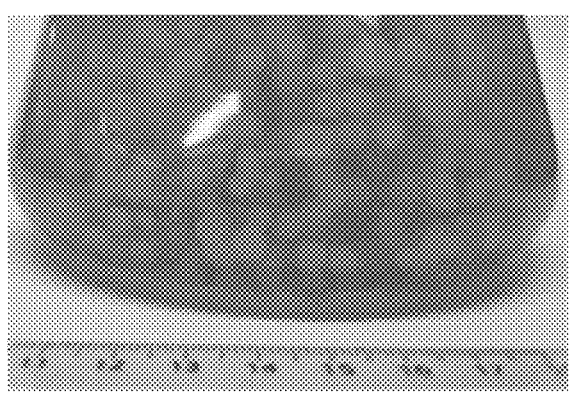
Figure 3D:
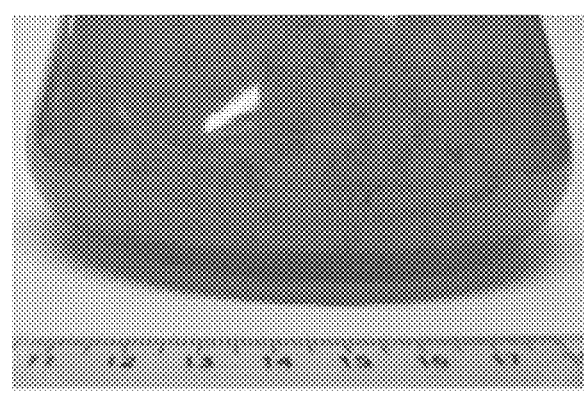
Figure 3E:
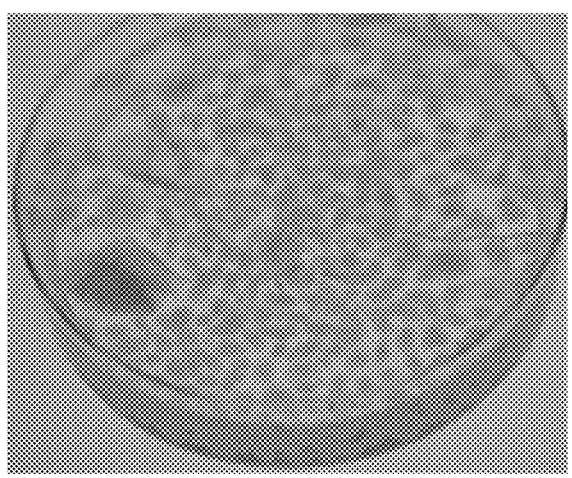
Figure 3F:
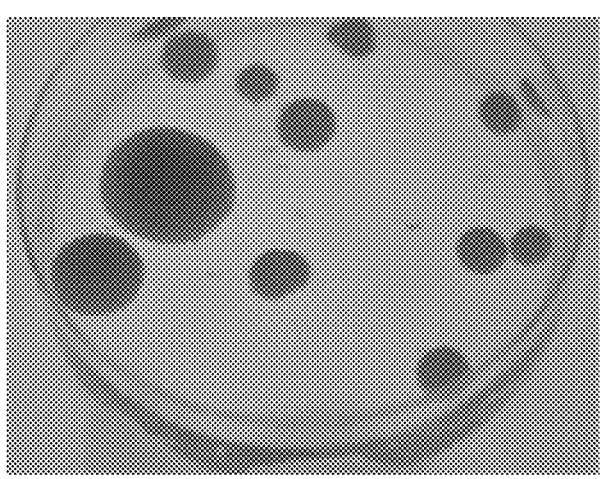

FIGS. 3A-3F present photographs of pellets after incubation of pure *T. ochracea* (FIGS. 3A and 3B) and co-incubation of *T. ochracea* with cellulose nanofibrils (CNFs) (FIGS. 3C and 3D), as well as small elongated pellets obtained upon co-incubation with 2% cellulose nanocrystals (CNCs) (FIG. 3E) and spherical pellets obtained upon co-incubation with 0.2% CNFs (FIG. 3F); FIGS. 3A-3D show pellets in 1 liter Erlenmeyer flasks in which incubation was performed, whereas FIGS. 3E and 3F show pellets transferred to water in 9 mm diameter glass Petri dishes.

FIGS. 4A-4C present scanning electron micrographs of pellets (after critical point drying) showing interior of pellets obtained from pure *T. ochracea* (FIG. 4A) or from co-incubation of *T. ochracea* with 0.2% (FIG. 4B) or 2% (FIG. 4C) CNFs (DS 0.1, 1p grade) (all scale bars=5 μm).

Figure 5A:
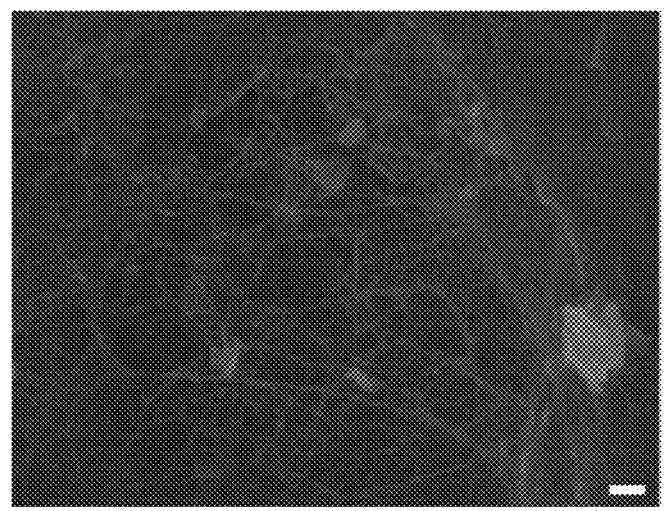
Figure 5B:
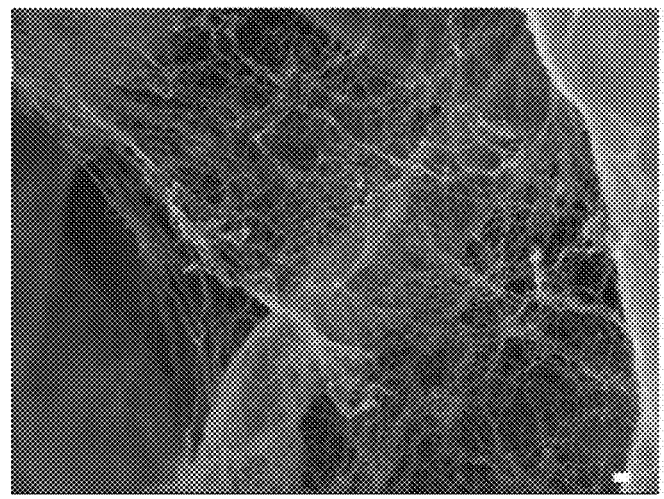
Figure 5C:
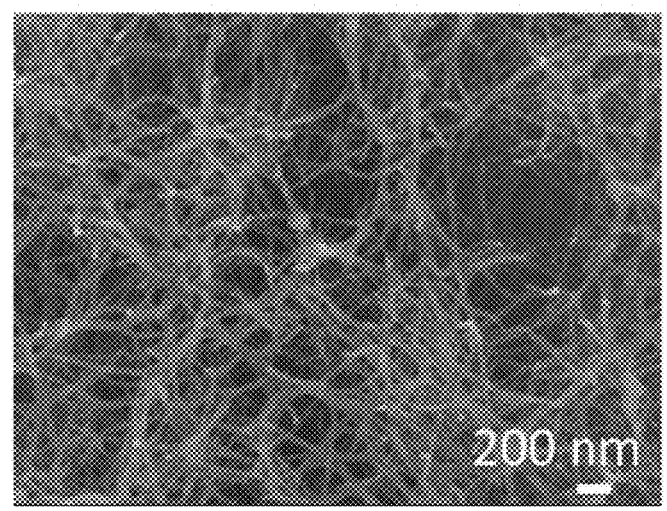

FIGS. 5A-5C present scanning electron micrographs showing nanofibrillar elements present in pellets obtained from pure *T. ochracea* (FIG. 5A) and from co-incubation of *T. ochracea* with 0.2% CNF (DS 0.1, 1p) (FIG. 5B) or 2% CNCs (FIG. 5C) (all scale bars=200 nm).

Figure 6A:
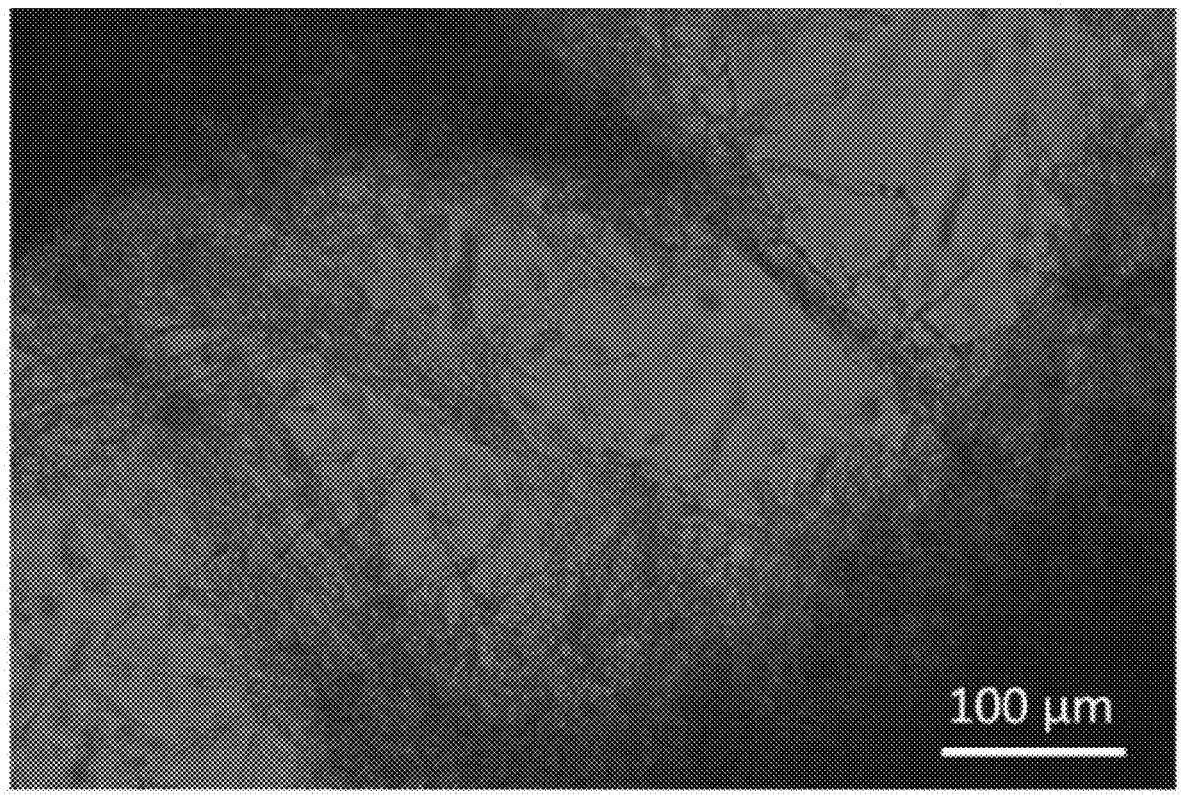
Figure 6B:
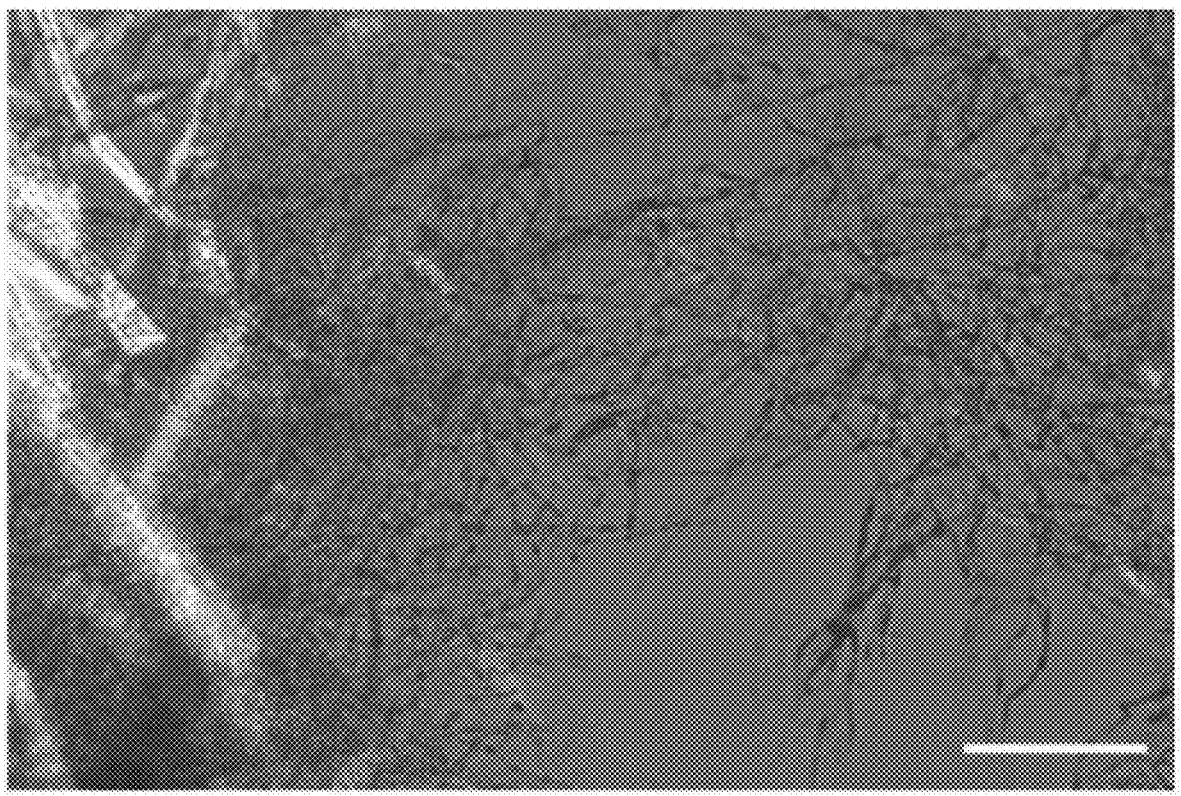
Figure 7A:
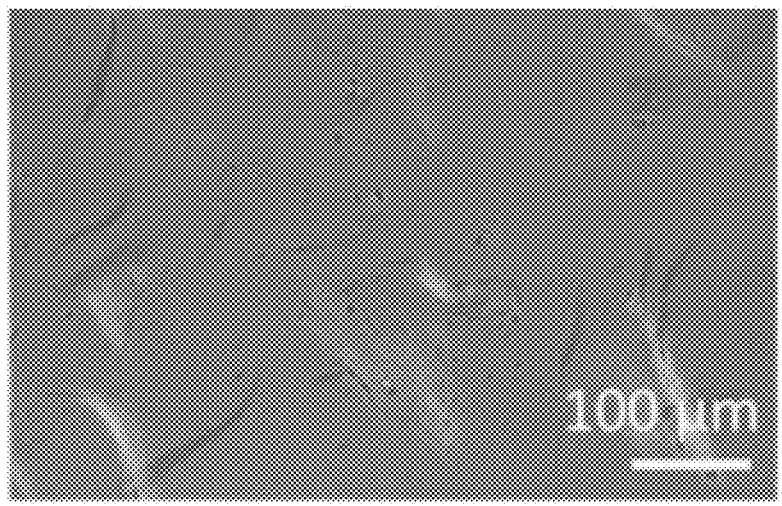
Figure 7B:
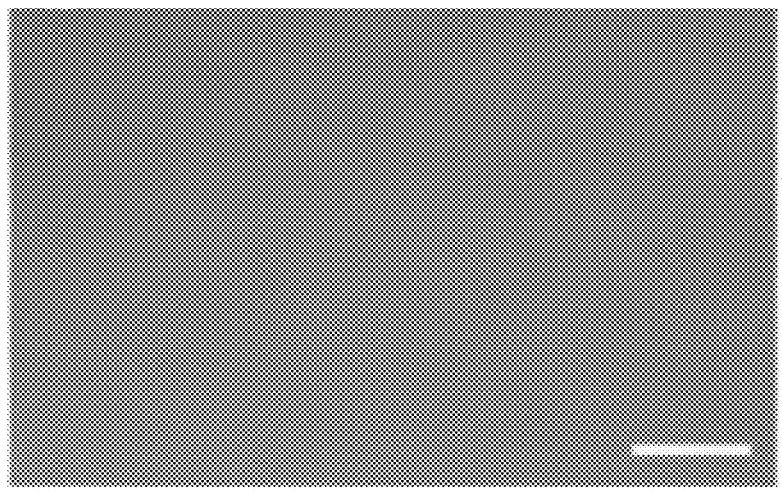
Figure 7C:
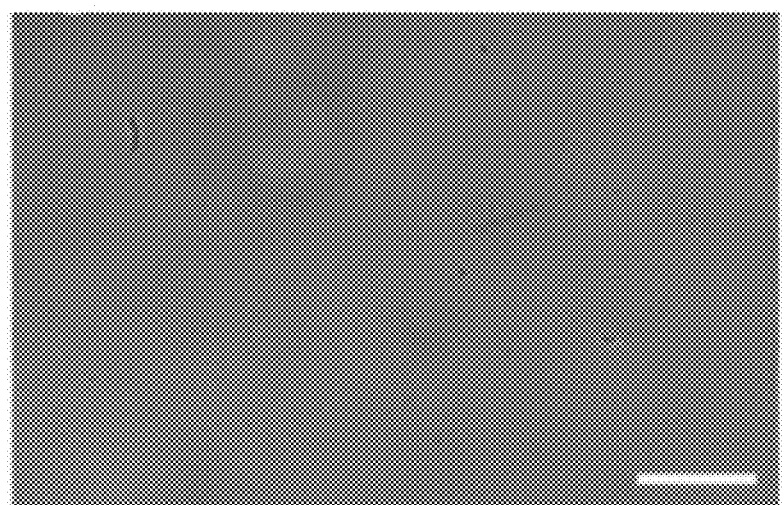
Figure 7D:
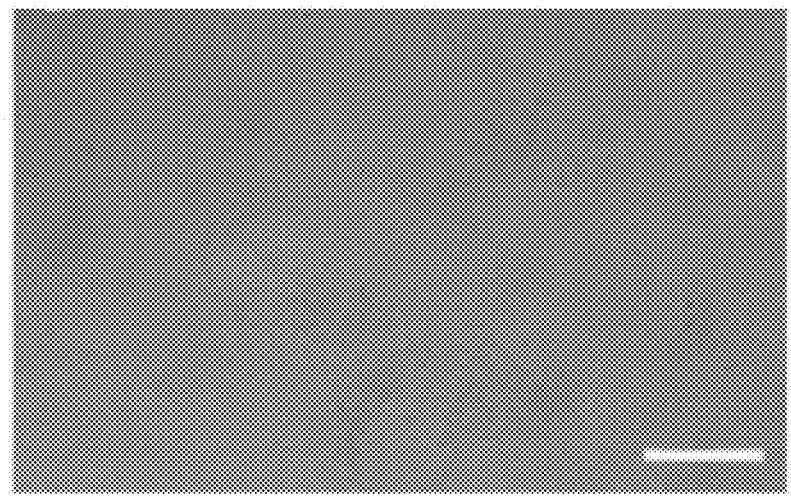
Figure 7E:
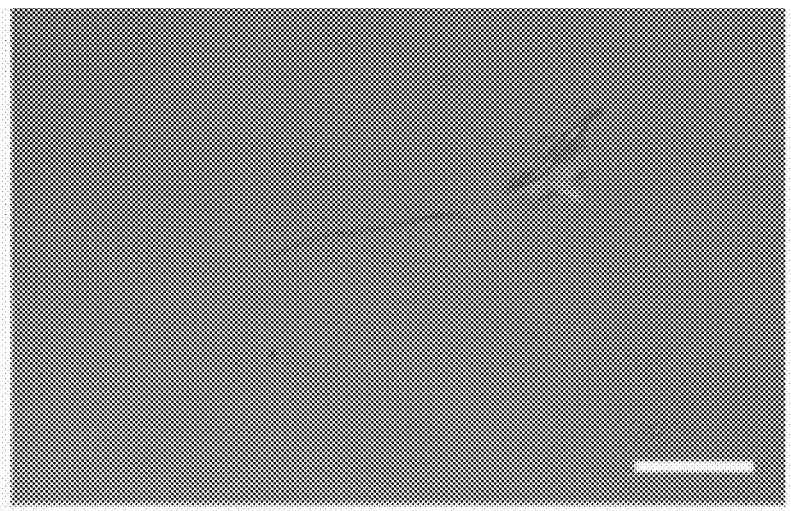
Figure 7F:
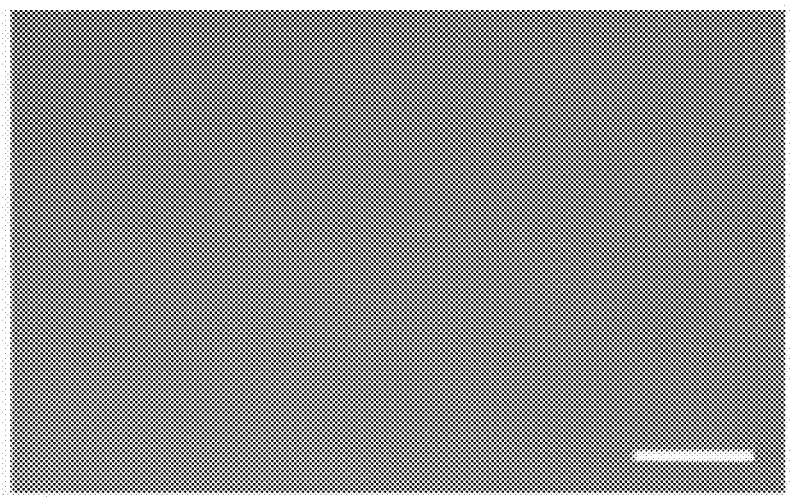

FIGS. 6A and 6B present polarized optical microscopy (POM) images of pellets obtained from pure *T. ochracea* (FIG. 6A) or from co-incubation of *T. ochracea* with 0.5% CNFs (DS 0.1, 1p grade) (FIG. 6B); pellets are pressed between a glass slide and coverslip, both scale bars=100 μm.

FIGS. 7A-7F present polarized optical microscopy (POM) images of CNF suspensions at 0.2% (FIGS. 7A, 7C and 7E) and corresponding featureless liquid medium after co-incubation of the CNF with *T. ochracea* (FIGS. 7B, 7D and 7F), for various grades of CNF: CNF DS 0.1, 1p grade (FIGS. 7A and 7B), CNF DS 0.1, 4p grade (FIGS. 7C and 7D), and CNF DS 0.3, 4p grade (FIGS. 7E and 7F) (all scale bars=100 μm).

Figure 8A:
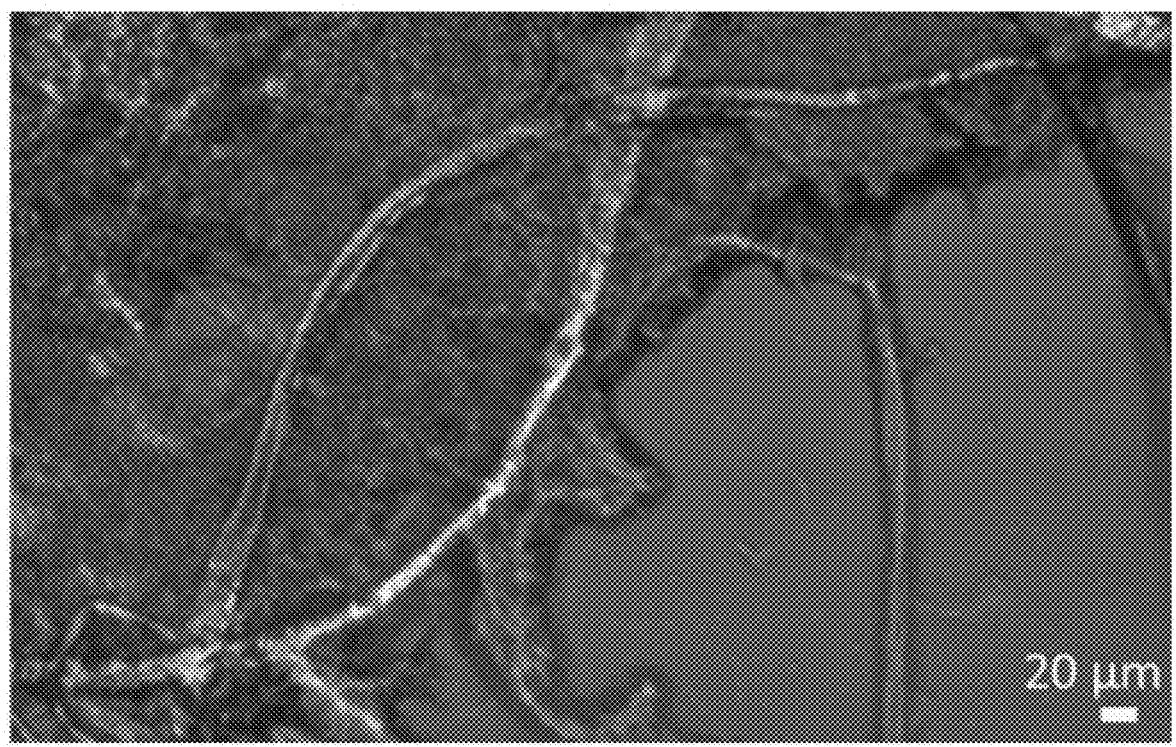
Figure 8B:
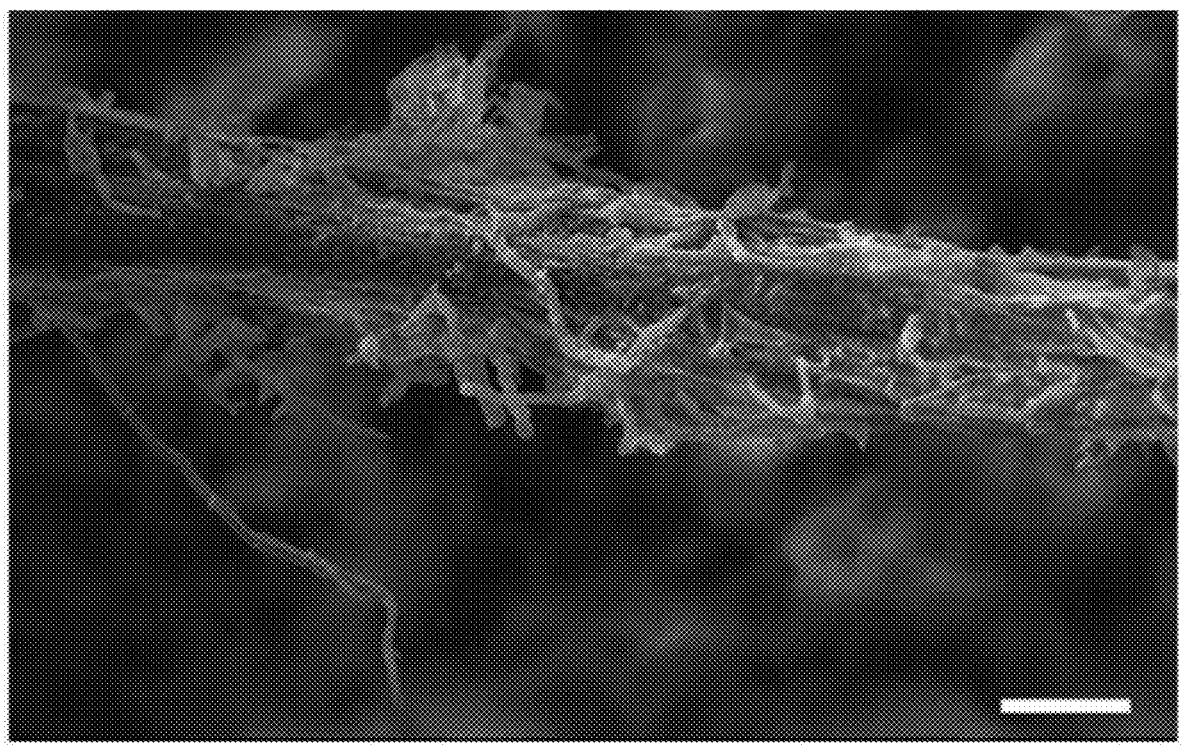
Figure 9A:
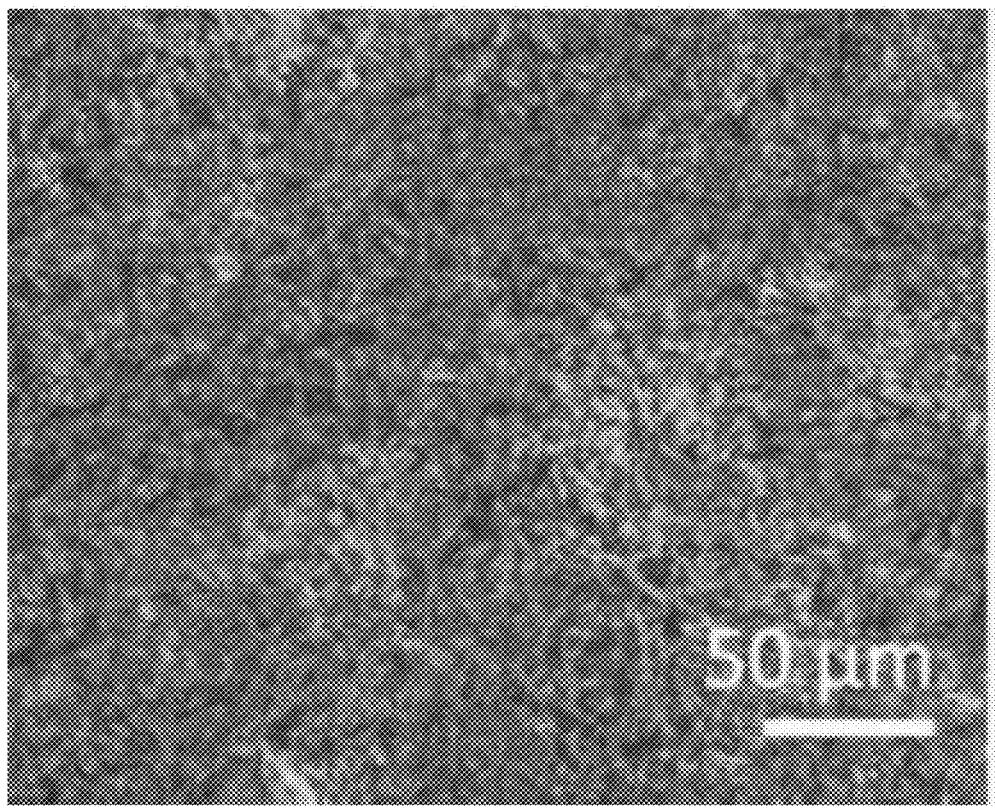
Figure 9B:
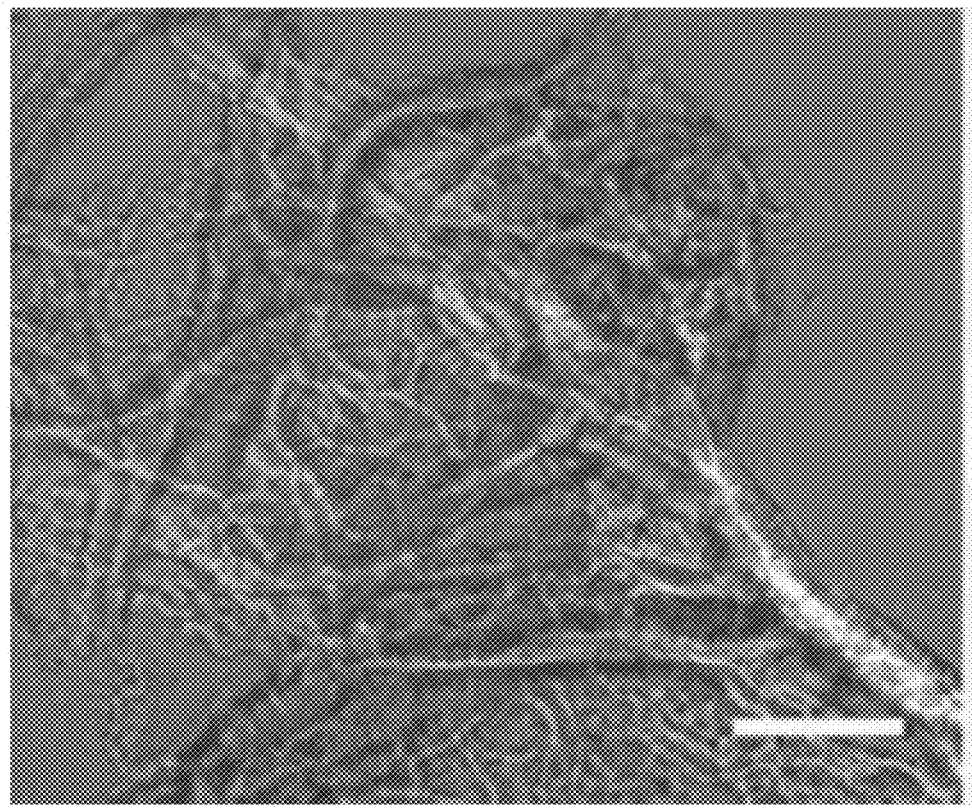
Figure 9C:
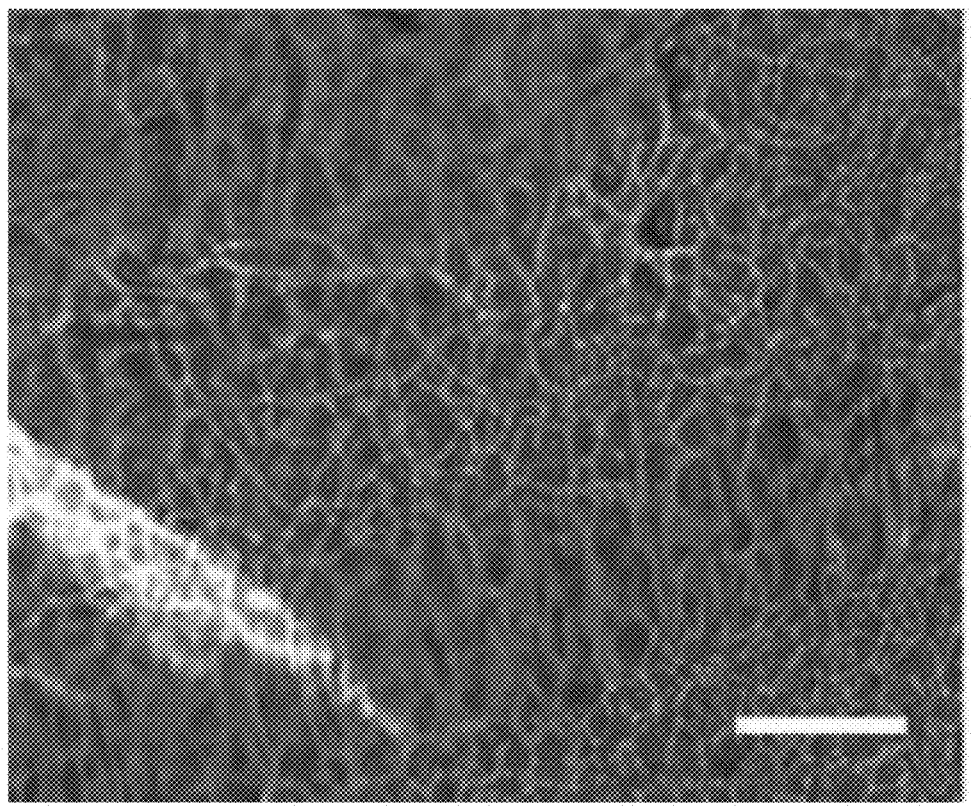
Figure 9D:
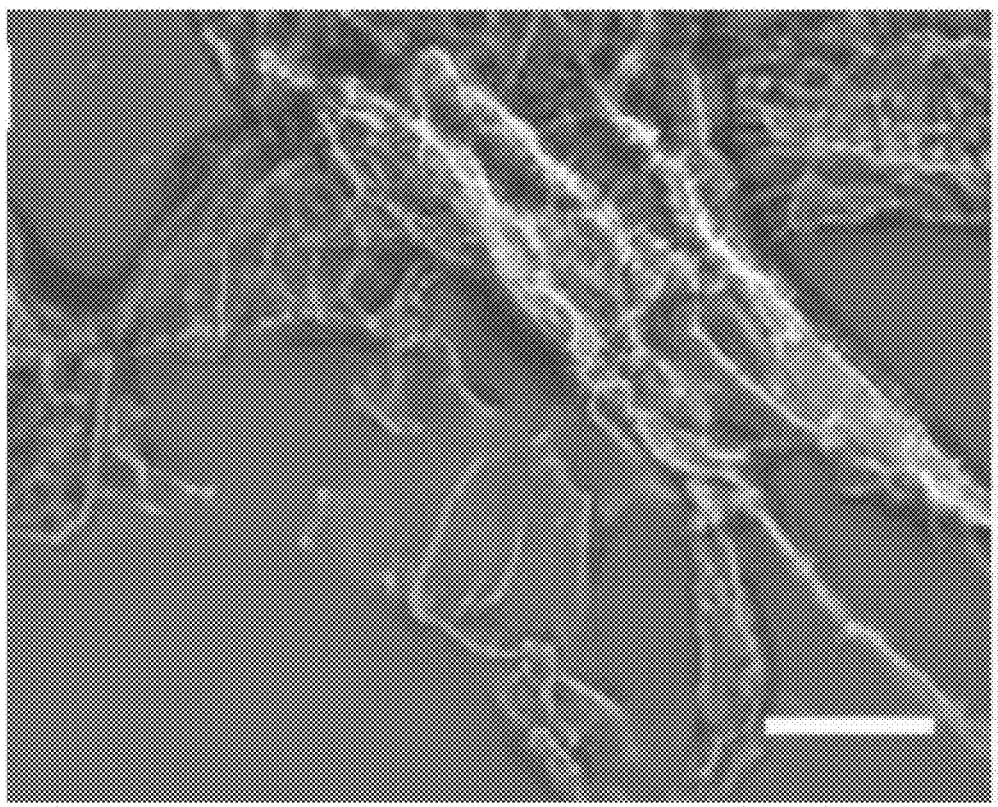

FIGS. 8A and 8B present a POM image of a pellet obtained by co-incubation of mycelium with 0.2% CNF (DS 0.1, 1p), and compression of the pellet between a glass slide and coverslip (FIG. 8A), and a scanning electron micrograph (FIG. 8B) of the same pellet after critical point drying (both scale bars=20 μm).

FIGS. 9A-9D present POM images of pellets dried onto glass slides, following co-incubation of *T. ochracea* with 0.2% CNF DS 0.1, 4p grade (FIG. 9A), 0.2% CNF DS 0.1, 1p grade (FIG. 9B), 0.2% CNF DS 0.3, 4p grade (FIG. 9C), and 0.5% CNF DS 0.1, 1p grade (FIG. 9D); in all cases, NC birefringence is closely associated with the mycelium network (all scale bars=50 μm).

Figure 10A:
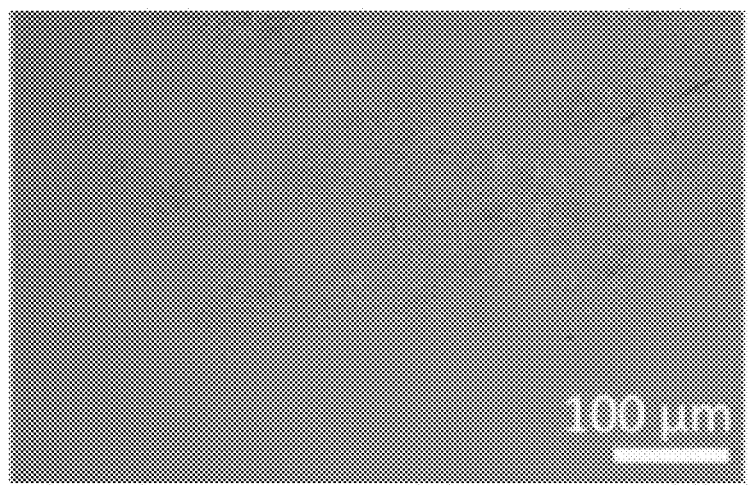
Figure 10B:
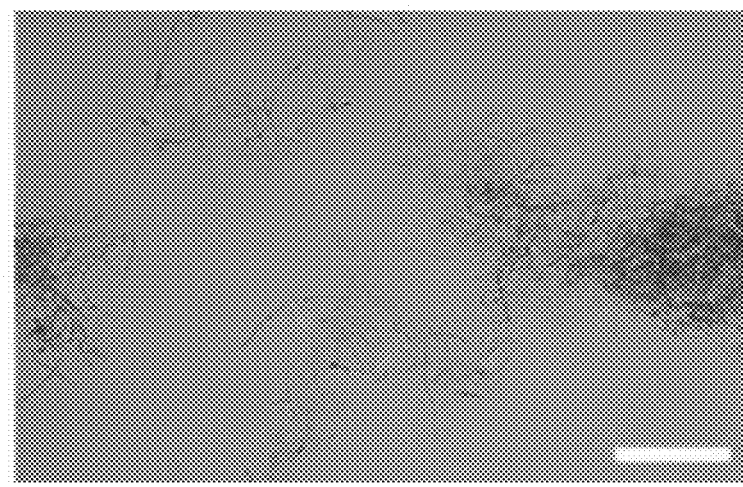
Figure 10C:
Figure 24:
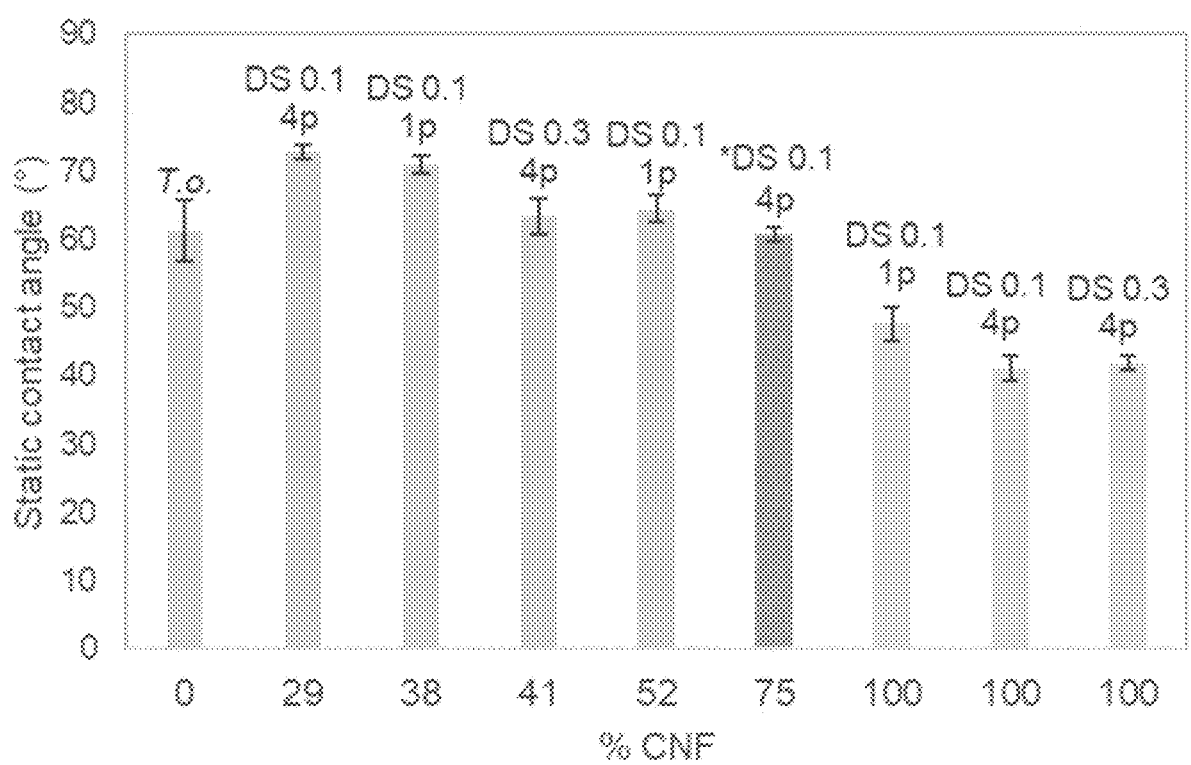

FIGS. 10A-10C present POM images of liquid medium containing enzymatic CNFs (10p) prior to co-incubation with *T. ochracea* (FIG. 10A), and of homogenized mixtures of *T. ochracea* following co-incubation with 0.25% of the enzymatic CNFs (FIG. 10B) or pulp fibers (FIG. 10C) (all scale bars=100 μm).

FIG. 11 presents ATR-FTIR spectra of films prepared from pure *T. ochracea*, pure CNFs (DS 0.1, 1p), or from a hybrid material (with ~30% CNF dry content) prepared by co-incubation of *T. ochracea* with 0.2% CNF (DS 0.1, 1p).

FIGS. 12A-12F present large scale (50 μm) AFM height images (FIGS. 12A and 12B), associated sections (FIGS. 12C and 12D), and small scale (2.5 μm) AFM height images (FIGS. 12E and 12F) for pure *T. ochracea* (FIGS. 12A, 12C and 12E) and hybrid material obtained by co-incubation of *T. ochracea* and 0.2% CNF (DS 0.1, 1p grade) (FIGS. 12B, 12D and 12F).

FIGS. 13A and 13B present AFM height (FIG. 13A) and amplitude (FIG. 13B) images of hyphae produced from the co-incubation of 2% CNCs with *T. ochracea.*

FIGS. 14A and 14B present cryo-scanning electron microscopy images of pellets obtained from pure *T. ochracea* (FIG. 14B) and *T. ochracea* co-incubated with 0.2% CNF (DS 0.1, 1p); hyphae cross-sections and organelle-filled interiors are seen in both samples (all scale bars=2 μm).

FIGS. 15A-15F present AFM height images of films formed from *T. ochracea* (FIGS. 15A-15C) or *T. ochracea* co-incubated with CNF (DS 0.1, 4p grade) (FIGS. 15D-15F), at scan sizes of 10×10 μm (FIGS. 15A and 15D), 5×5 μm (FIGS. 15B and 15E) and 0.3×0.3 μm (FIGS. 15C and 15F).

FIGS. 16A-16F present representative nanomechanical images of films formed from *T. ochracea* (FIGS. 16A-16C) or *T. ochracea* co-incubated with CNF (DS 0.1, 4p grade) (FIGS. 16D-16E), used to determine average elastic modulus of samples.

FIG. 17 presents a bar graph showing normalized absorbance at 550 nm after 0 or 12 hours for pure *T. ochracea* (T. o) liquid mixtures and hybrid mixtures produced by co-incubation of *T. ochracea* with 0.2% or 0.5% carboxymethylated CNFs (DS 0.1, 1p or DS 0.1, 4p or DS 0.3, 4p grades); undiluted samples (top; native sample concentrations are indicated above bars) are relatively stable over time, whereas samples diluted to 0.1 wt % (bottom) exhibit phase separation.

FIGS. 18A-18D present representative photographs showing stages of an exemplary bio-fabrication of mycelium-NC hybrids; mycelium-NC pellets in liquid culture are obtained upon incubation (FIG. 18A), and homogenized to form a suspension of mycelium-NC hybrid bio-composite (FIG. 18B), a film (d=8 cm) is obtained by vacuum filtration of a homogenized suspension (FIG. 18C), or an aerogel (d=4 cm) is obtained by freeze drying the homogenized suspension (FIG. 18D).

FIGS. 19A-19L presents photographs of exemplary films (FIGS. 19A-19H) and aerogels (FIGS. 19I-19L) prepared from mycelium-nanocellulose hybrid materials according to some embodiments of the invention (FIGS. 19A-19D, from pure mycelium (FIGS. 19E and 19I), pure CNFs (FIGS. 19F and 19J), or a mixture of 75% mycelium and 25% CNFs (FIG. 19H); nanocellulose in hybrid materials is 40% CNFs—DS 0.1, 4p (FIG. 19A) or 1p grade (FIG. 19B), 35% CNFs—DS 0.3, 4p grade (FIG. 19C), 60% CNFs—DS 0.1, 1p grade (FIG. 19D), about 50% CNCs (FIGS. 19G and 19K), or about 50% CNFs—DS 01, 1p grade (FIG. 19L).

FIG. 20A-20F present scanning electron micrographs of cross-sections of ruptured films formed from a mycelium-NC hybrid (FIG. 20A) of 40% CNFs (DS 03, 4p)+60% mycelium (showing layers of smashed mycelium), from a mixture (FIG. 20B) of 50% CNFs (DS 0.1, 4p) and 50% mycelium (showing air pockets with detached CNF nanofibers; area highlighted with arrow), from 100% CNFs (D3 0.3, 4p) (FIG. 20E) (showing clearly distinguished nanoscale fibers), or from 100% mycelium (FIG. 20D) (in which hyphae appear collapsed, with no distinct fibers), and of a top surface (FIG. 20C) of 100% mycelium film (clearly showing 2 μm hyphae); fibers incorporated into mycelium mass, and pulled out due to mechanical force are observable in a detailed micrograph of a mycelium-NC hybrid (FIG. 20F) of 40% CNFs (DS 03, 4p)+60% mycelium.

FIGS. 21A-21D present bar graphs showing tensile strength (FIGS. 21A and 21C) and strain at break (FIGS. 21B and 21D) of composite films prepared by adding CNFs (DS 0.1, 4p) to already grown mycelium (FIGS. 21A and 21B) or hybrid films prepared by co-incubation of mycelium with various CNF grades (FIGS. 21C and 21D).

FIGS. 22A and 22B present bar graphs showing the water uptake after 30 minutes of films prepared from a hybrid obtained by co-incubation of mycelium with 0, 40, or 60% CNFs—DS 0.1, 1p grade, or from 100% CNFs (FIG. 22A) and films prepared by post-incubation mixtures of mycelium with 0, 40, or 60% CNFs—DS 0.1, 4p grade, or from 100% CNFs (FIG. 22B).

FIGS. 23A and 23B present graphs showing the relationship between CNF content and density (FIGS. 23A and 23B), tensile strength (FIG. 23A) and water uptake (FIG. 23B) of exemplary films formed from 100% CNFs, 100% mycelium (0% CNFs) or from hybrid material obtained by co-incubation of mycelium and CNFs (DS 0.1, 1p grade).

FIG. 24 presents a bar graph showing static water contact angles of a film prepared from pure mycelium (T.o.), CNF-mycelium films (with 29%, 38%, 41% or 52% CNF) prepared from hybrid material obtained by co-incubation of mycelium with various CNF grades or from post-incubation mixture of 75% CNFs and 25% mycelium, and control films prepared from 100% CNFs of various grades; CNF grades indicated above bars, and CNF percentage indicated below bars.

Figure 25:

FIG. 25 presents an image showing a multi-cell tray (with separable cells) formed from a mycelium-containing composition according to some embodiments of the invention (composition is light-colored, whereas soil in tray is dark-colored).

Figure 26:
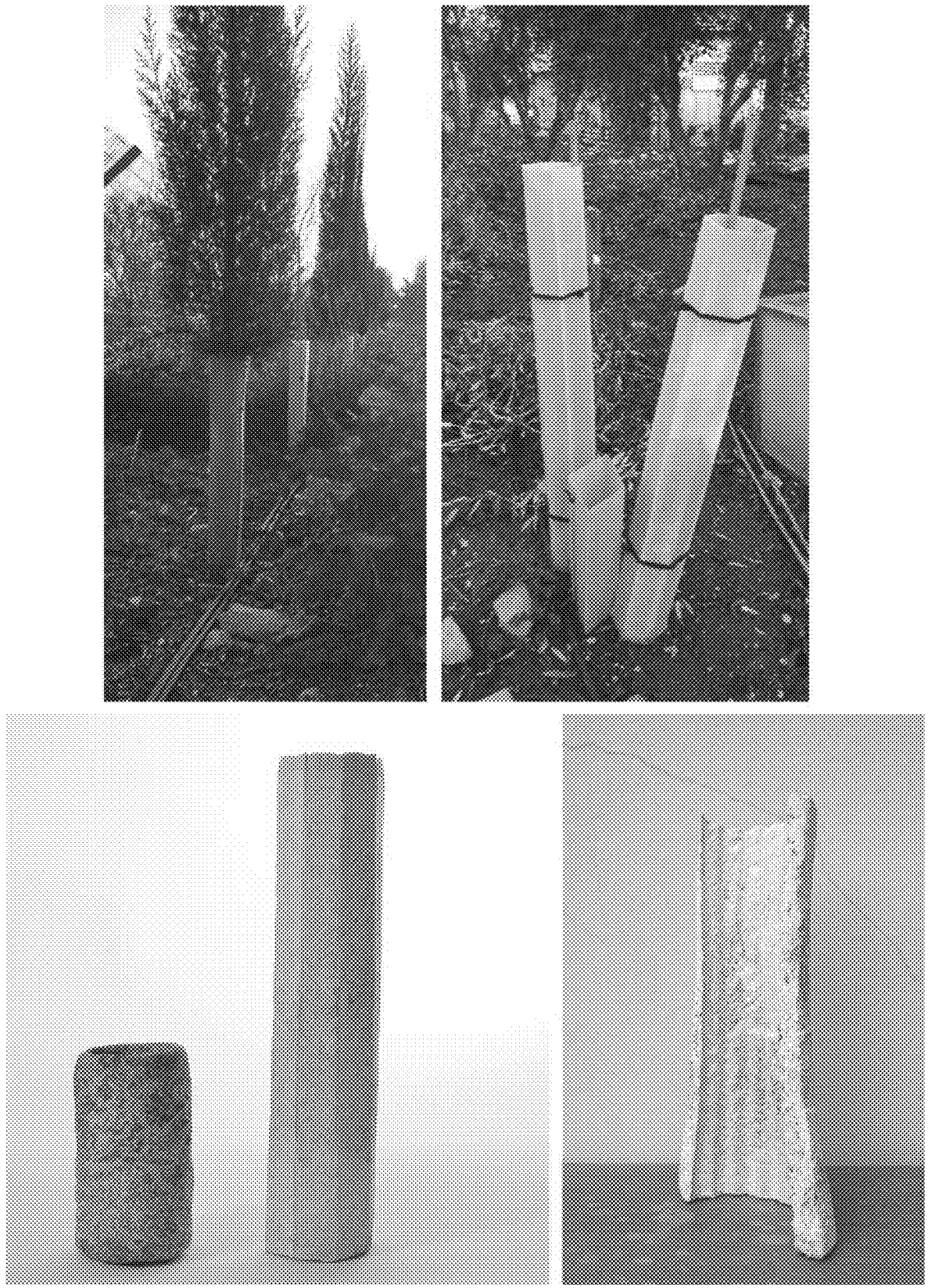

FIG. 26 presents images showing various tree protectors formed from a mycelium-containing composition according to some embodiments of the invention.

Figure 27:
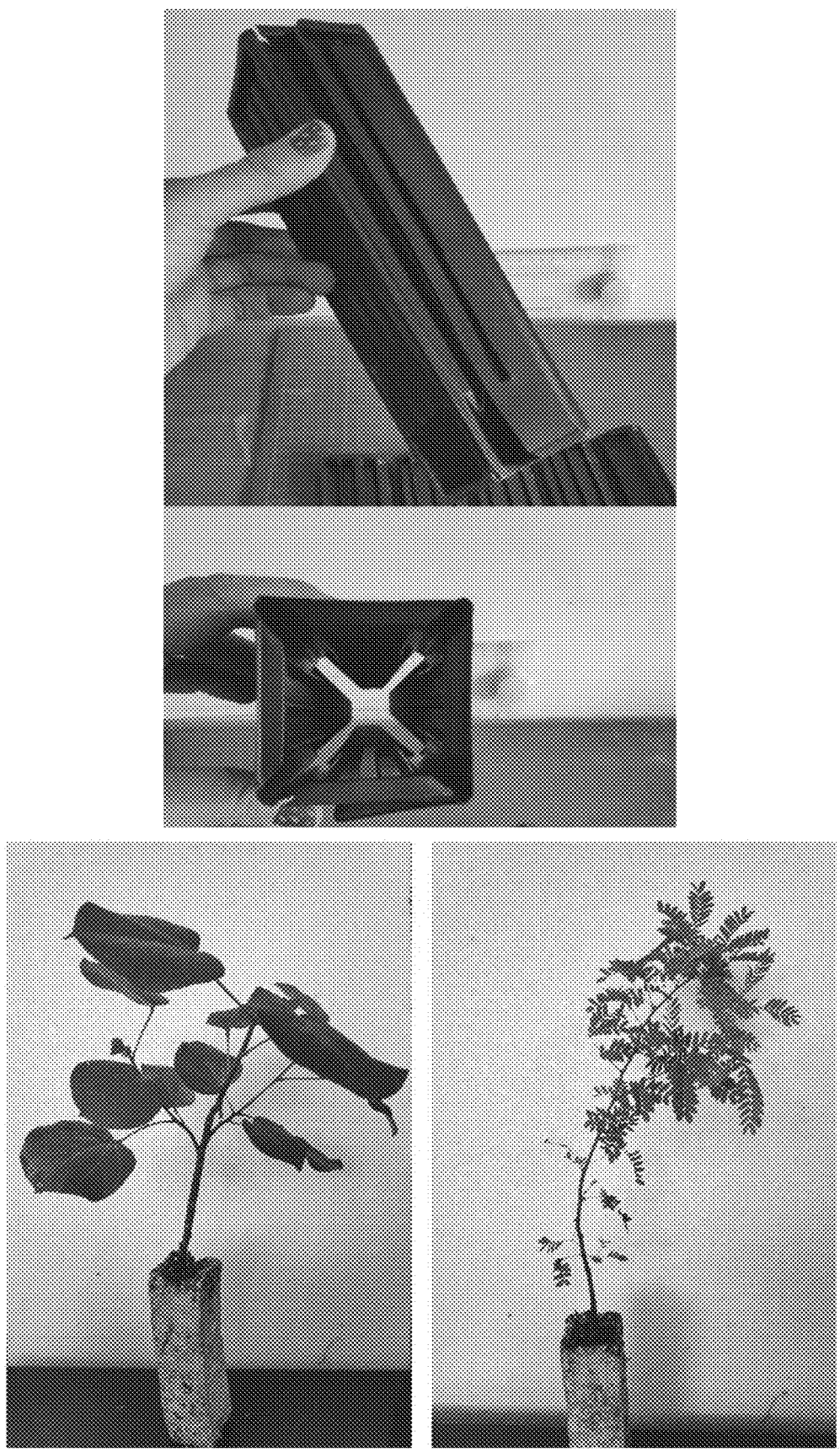

FIG. 27 presents images showing root trainers formed from a mycelium-containing composition according to some embodiments of the invention.

DESCRIPTION OF SPECIFIC EMBODIMENTS OF THE INVENTION

The present invention, in some embodiments thereof, relates to materials, and more particularly, but not exclusively, to composite (hybrid) materials that comprise mycelium in combination with plant-derived substances or synthetic analogs thereof, such as, for example, cellulose and/or cellulose-based materials.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered a mycelium-based hybrid, which can be produced in a single bio-fabrication step via an organic self-assembly process, where an additional substance (other than mycelium), such as nanocellulose (NC), or other types of cellulose or nanoparticles, becomes intimately enfolded within the mycelial network, as opposed to being simply mixed with the mycelium post-growth (e.g., as described by Sun et al. [*Sci Rep* 2019, 9:3766]). In particular, fungal mycelium is incubated alongside standard nutrients and the additional substance under agitated liquid culture conditions to produce a homogeneous network structure comprising both mycelium and the additional substance. The properties of the obtained material may be modulated by the nature of the assembly and the final material composition.

The additional substance may optionally comprise cellulose (e.g., in a form of fibers and/or nanoparticles such as CNCs or CNFs), and/or nanoparticles comprising a polymeric substance other than cellulose, such as polysaccharides (e.g., hemicellulose), polypeptides (e.g., silk), and/or synthetic polymers (e.g., polyester, nylon).

Some previously described mycelium-based bio-composites combine fungal inoculum with solid biomass such as woodchips or saw dust [Attias et al., *J Clean Prod* 2019, 119037; Jones et al., *J Bionanoscience* 2017, 11:241-257; Girometta et al., *Sustainability* 2019, 11:281]. In contrast, the approach described herein, whereby the additional substance (optionally biomass such as a nanoscale colloidal particle) is co-incubated with mycelium, has the advantages of efficient integration of the mycelium and non-mycelium components, and of producing a versatile liquid mass. This liquid may optionally be used to form materials of various types. For example, the liquid may be dried into sheets or films (which may optionally be used like paper and/or to coat another material), e.g., by vacuum and/or by spray drying the liquid. Alternatively, the liquid may be used to produce aerogels (which may optionally be used as a foam), e.g., by freeze-drying the liquid. In another alternative, the liquid may optionally be 3D-printed (e.g., by multi-component 3D-printing).

In addition, the hybrid may also optionally be processed by mixing the obtained hybrid with macro-scale solid biomass (e.g., woodchips, saw dust, or pulp fibers) to give a space-filling mycelium-based bio-composite such as described in the art, except that the bio-composite is strengthened or otherwise functionally modified by the inclusion of the additional substance.

Referring now to the drawings, FIGS. 1A-1D show various types of cellulose which may optionally be combined with mycelium according to some embodiments of the invention.

Figure 11:
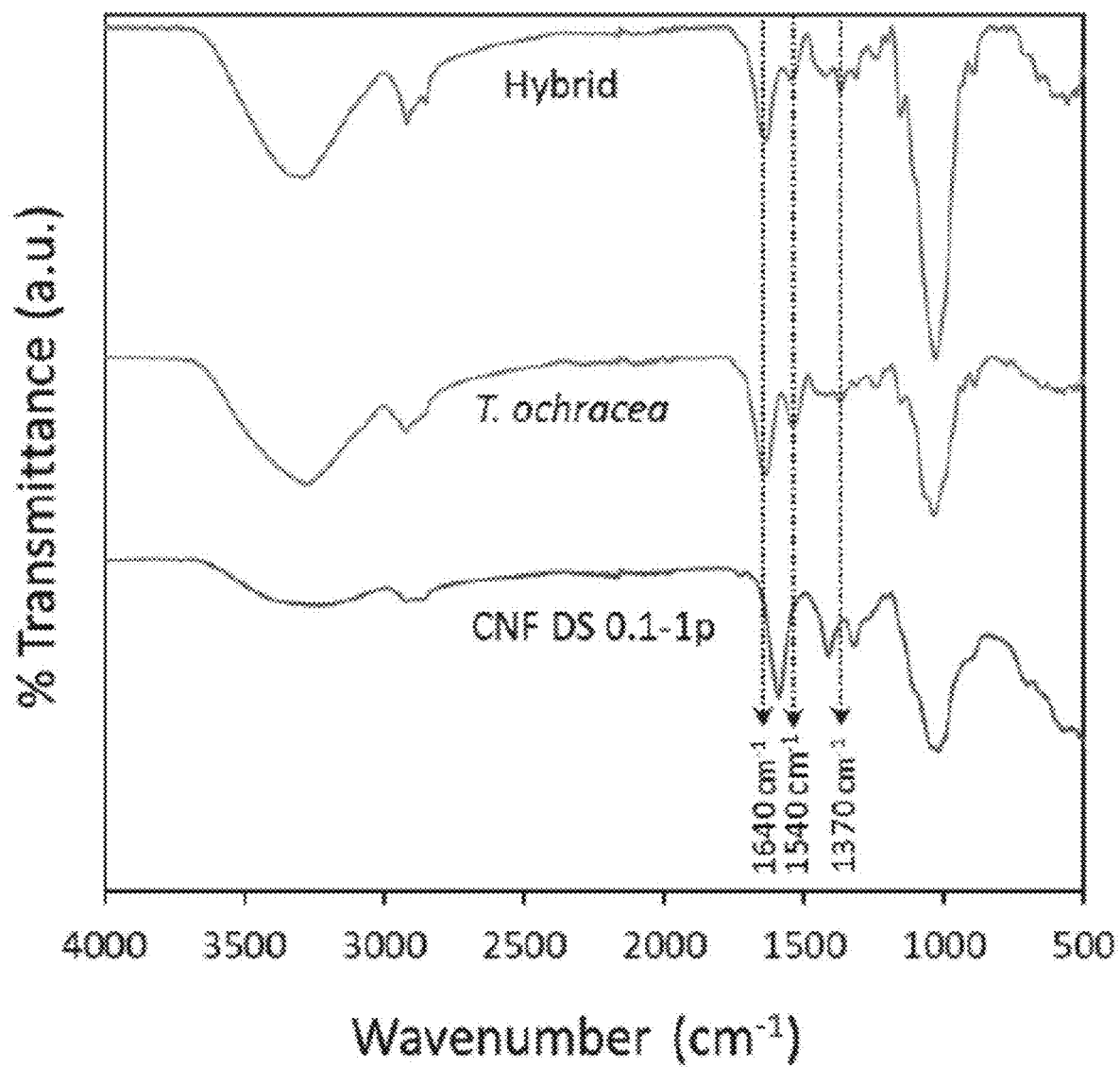

FIGS. 2A-3F show pellets obtained by co-incubation of a fungus and nanocellulose according to some embodiments of the invention. FIGS. 4A-5C, 8B and 13A-15B show the microscopic structure of the interior of pellets obtained from pure fungus and from co-incubation of a fungus and nanocellulose. FIGS. 6A-6B, 8A and 9A-9D show the cellulose (via polarized optical microscopy) of various pellets, and FIGS. 7A-7F and 10A-10C show the cellulose (via polarized optical microscopy) in the medium in which the fungus is grown. FIG. 11 shows that cellulose incubated with mycelium exhibits spectroscopic properties associated with mycelium.

Figure 17:
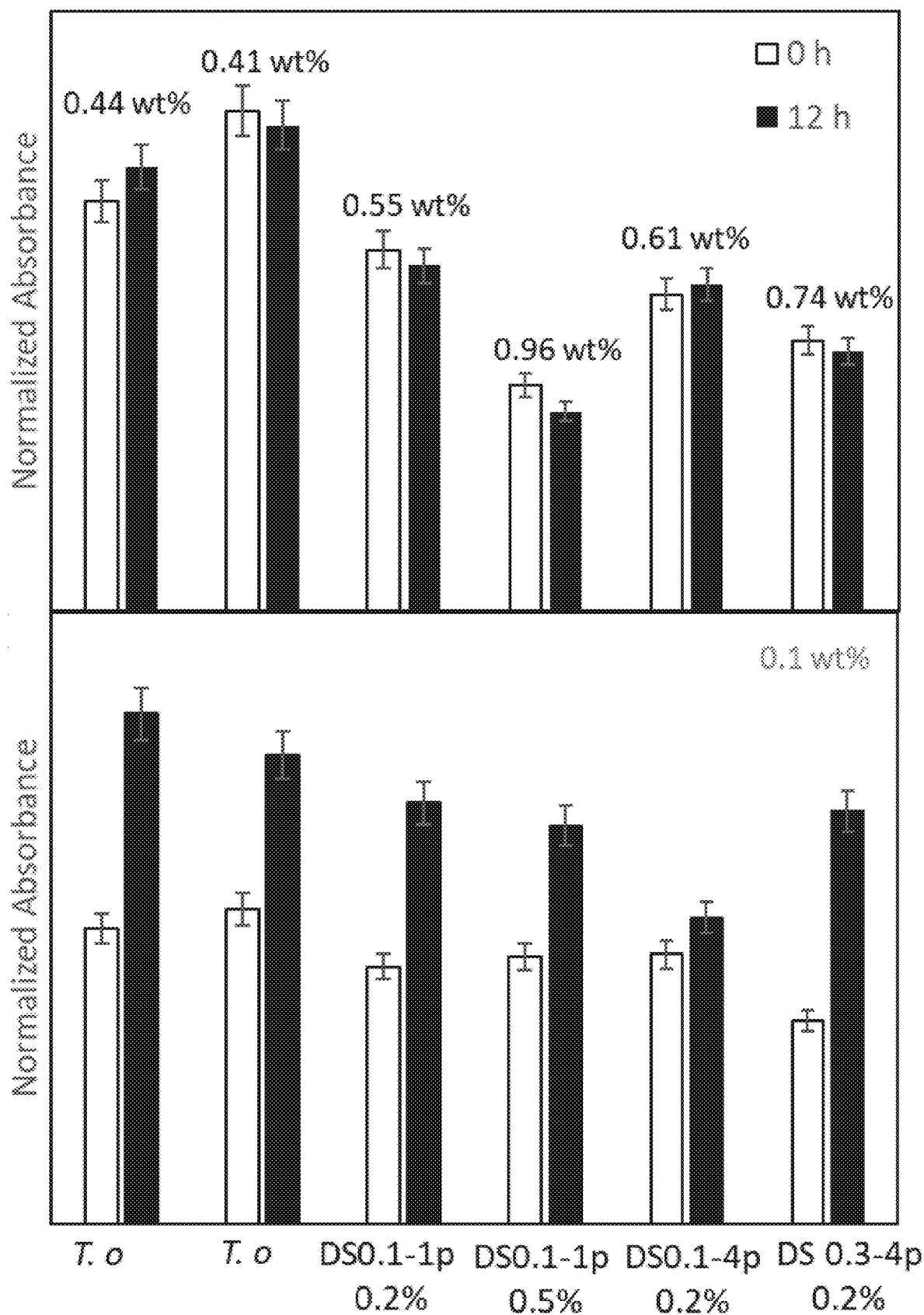

FIG. 15A-16F show the structure and mechanical properties of films formed from pure mycelium or mycelium co-incubated with nanocellulose according to some embodiments of the invention. FIG. 17 shows that exemplary hybrid materials resist dilution, with a water phase forming above the diluted material.

FIGS. 18A-18D show the stages of an exemplary bio-fabrication of a mycelium-nanocellulose hybrid material. FIGS. 19A-19L show exemplary films and aerogels prepared from mycelium-nanocellulose hybrid materials according to some embodiments of the invention. FIGS. 25-27 show various articles-of-manufacture prepared from a mycelium-containing composition according to some embodiments of the invention.

FIGS. 20A-24 compare the microscopic structure and physical properties of exemplary films prepared from a hybrid material obtained by co-incubation of mycelium and cellulose according to some embodiments of the invention with materials prepared by post-incubation mixtures of mycelium with cellulose.

Composition:

According to an aspect of some embodiments of the invention, there is a composition (also referred to herein interchangeably as a "hybrid" or "hybrid material") comprising mycelium and an additional substance, such as cellulose and/or a plurality of nanoparticles, as described herein in any of the respective embodiments, wherein at least a portion of the additional substance is incorporated within the mycelium.

Herein, the term "mycelium" refers to a mass of a fungus (representing a portion of the fungus or the entire fungus) formed from a plurality of filamentous multicellular structures (referred to as "hyphae").

In some of any of the embodiments described herein, the fungus comprises a fungus capable of digesting lignocellulose. Examples of fungus capable of digesting lignocellulose include, without limitation, white rot fungus, soft rot fungus and/or brown rot fungus.

Herein, the term "white rot fungus" refers to any fungus species capable of breaking down lignin in wood.

Herein, the term "soft rot fungus" refers to any fungus species capable of breaking down cellulose in wood via enzymatic activity of cellulase (e.g., at a faster rate than the lignin in the wood is broken down by the fungus).

Herein, the term "brown rot fungus" refers to any fungus species capable of breaking down cellulose in wood via hydrogen peroxide production (e.g., at a faster rate than the lignin in the wood is broken down by the fungus).

In some of any of the embodiments described herein, the fungus comprises a basidiomycotic fungus.

Herein, the term "basidiomycotic fungus" refers to any fungus belonging to the division Basidiomycota.

In some of any of the respective embodiments, at least a portion of the basidiomycotic fungus belongs to the class Agaricomycetes. In some embodiments, at least a portion of the basidiomycotic fungus belongs to the order Polyporales. In some embodiments, at least a portion of the basidiomycotic fungus belongs to the family Polyporaceae. In some embodiments, at least a portion of the fungus basidiomycotic fungus belongs to the genus *Trametes*. *Trametes ochracea* is an exemplary fungus.

Herein throughout, "incorporation" of a substance (e.g., cellulose and/or nanoparticles) within mycelium (or for a substance to be "incorporated within" mycelium, and other grammatical variants thereof) refers to the substance being encompassed within the cells (e.g., cell wall and/or cytoplasm) and/or adhering to the cells of the mycelium; and does not include mere presence of the substance in spaces between hyphae of the mycelium, or include breakdown products of the substance, such as digested cellulose (e.g., glucose), absorbed by the mycelium. In some of any of the respective embodiments described herein, incorporated substance refers to particles (e.g., crystalline and/or fibrillar particles) for which at least a portion of the particle is encompassed within the cells of the mycelium.

In some of any of the respective embodiments, the additional substance comprises a plurality of nanoparticles.

Herein, the term "nanoparticle" refers to any discrete mass having a cross section in at least one dimension, wherein the cross section is less than 1 micron in width in every direction within the plane of the cross section. Thus, a "nanoparticle" may have any length in a direction outside the plane of the cross section. Nanoparticles which are considerably longer along an axis roughly perpendicular to a cross section which is less than 1 micron in width are also referred to herein as "nanofibrils".

Nanoparticles according to any of the respective embodiments described herein may comprise a polymeric substance, for example, a polysaccharide (e.g., a cellulose and/or hemicellulose), a polypeptide (e.g., silk), a lignocellulose (i.e., a plant derived material comprising lignin, cellulose and/or hemicellulose), and/or a synthetic polymer (e.g., a polyester and/or a nylon), optionally a synthetic polymer suitable for forming fibers (e.g., textile fibers).

Alternatively or additionally, the nanoparticles may optionally comprise a form of carbon (e.g., graphene, carbon nanotubes, carbon nanofibrils, etc.) and/or an inorganic substance such as a metal and/or metal oxide.

Nanoparticles (as defined herein) which consist primarily of cellulose (i.e., at least 50% by weight of the nanoparticle is cellulose) are referred to herein interchangeably as "nanocellulose" or "NC".

In some of any of the respective embodiments, the additional substance comprises a cellulose.

Except when specifically indicated otherwise, cellulose according to any of the respective embodiments described herein may be derived from and/or comprised by any source of cellulose (e.g., a plant or bacterial source); including, for example, natural cellulose fibers, substantially pure cellulose, and/or cellulose-containing biomass, such as lignocellulose (e.g., from wood).

It is expected that during the life of a patent maturing from this application many relevant types of cellulose (and nanocellulose), e.g., differing by cellulose source, morphology, degree of crystallinity and/or type and/or degree of chemical modification, will be developed and the scope of the term "cellulose" (and "nanocellulose") is intended to include all such new technologies a priori.

In some of any of the respective embodiments, the cellulose may comprise a chemically unmodified cellulose and/or a chemically modified cellulose, which optionally comprises anionic groups and/or cationic (e.g., ammonium) groups.

In some of any of the respective embodiments, the anionic groups are carboxylic acid groups (i.e., —C(=O)OH and/or —$CO_2^-$ groups) and/or sulfate groups (i.e., —O—S(=O)$_2$—OH and/or —$OSO_3^-$ groups).

In some of any of the respective embodiments, the cellulose comprises carboxymethylated cellulose, e.g., cellulose with a —$CH_2$—C(=O)OH group attached to one or more oxygen atoms thereof.

Alternatively or additionally, carboxylic acid groups may optionally be obtained by oxidation (e.g., by TEMPO ((2,2,6,6-tetramethylpiperidin-1-yl)oxyl)), for example, oxidation of —$CH_2OH$ group to carboxylic acid groups.

In some of any of the respective embodiments, the cellulose comprises nanocellulose; optionally, cellulose nanofibrils (CNFs), cellulose nanocrystals (CNCs) and/or microfibrillated cellulose (MFC).

In some of any of the embodiments described herein relating to cellulose nanofibrils (CNFs) and/or microfibrillated cellulose (MFC), the CNFs and/or MFC is enzymatically treated and/or chemically modified (e.g., with a —$CH_2$—C(=O)OH group attached to one or more oxygen atoms thereof).

In some of any of the embodiments described herein relating to cellulose, the cellulose is in a form selected from the group consisting of pulp fibers, regenerated cellulose fibers (e.g., viscose, rayon and/or cellophane), and/or natural cellulose fibers (e.g., fibers derived from cotton or any other suitable fiber-bearing crop).

In some of any of the embodiments described herein relating to a composition, at least 1% (e.g., from 1% to 99%) or at least 3% (e.g., from 3% to 99%), and preferably at least 10% (e.g., from 10% to 99%) of the additional substance (e.g., cellulose and/or nanoparticles) in the composition (according to any of the respective embodiments described herein) is incorporated within the mycelium (as defined herein). Optionally, at least 20% (e.g., from 20% to 99%), or at least 30% (e.g., from 30% to 99%), or at least 40% (e.g., from 40% to 99%), or at least 50% (e.g., from 50% to 99%), or at least 60% (e.g., from 60% to 99%), or at least 70% (e.g., from 70% to 99%), or at least 80% (e.g., from 80% to 99%), or at least 90% (e.g., from 90% to 99%), or at least 95% (e.g., from 95% to 99%), or at least 98%, or at least 99% of the additional substance (e.g., cellulose and/or nanoparticles) in the composition is incorporated within the mycelium.

In some of any of the respective embodiments described herein, the additional substance (e.g., cellulose and/or nanoparticles) incorporated within the mycelium comprises at least 10% (e.g., from 10% to 90%), or at least 20% (e.g., from 20% to 90%), or at least 30% (e.g., from 30% to 90%), or at least 40% (e.g., from 40% to 90%), or at least 50% (e.g., from 50% to 90%), or at least 60% (e.g., from 60% to 90%), or at least 70% (e.g., from 70% to 90%), of the total dry weight of the mycelium and the additional substance (e.g., cellulose and/or nanoparticles, respectively) incorporated within the mycelium.

In some of any of the respective embodiments described herein, a water uptake of the composition (e.g., as determined upon exposure to water for 30 minutes at about 25° C.) is no more than 1000% (e.g., from 10% to 1000%) of the dry weight of the composition; and optionally no more than 800% (e.g., from 10% to 800%), or no more than 600% (e.g., from 10% to 600%), or no more than 500% (e.g., from 10% to 500%), or no more than 400% (e.g., from 10% to 400%), or no more than 300% (e.g., from 10% to 300%), or no more than 200% (e.g., from 10% to 200%) of the dry weight of the composition.

As exemplified herein, cellulose which is not incorporated into mycelium generally exhibits a greater water uptake, which commonly leads to structural weakening, or even mechanical failure.

Furthermore, relatively low water uptake (e.g., as described herein) may be associated with an advantageously increased dewatering rate during production. For example, the considerable time of dewatering is a significant problem in the manufacture of paper-like products from nanocellulose.

In some of any of the respective embodiments described herein, the composition is in a form of a layer (e.g., a flexible or rigid layer), optionally a film and/or sheet (e.g., paper-like sheet). The thickness of the layer is preferably considerably (e.g., at least 10-fold, or at least 100-fold) thinner than the length of the layer in both perpendicular directions. In some embodiments, the thickness of the layer is no more than 5 mm (e.g., from 0.01 to 5 mm), optionally no more than 2 mm (e.g., from 0.01 to 2 mm), optionally no more than 1 mm (e.g., from 0.01 to 1 mm), optionally no more than 0.5 mm (e.g., from 0.01 to 0.5 mm), optionally no more than 0.2 mm (e.g., from 0.01 to 0.2 mm), and optionally no more than 0.1 mm (e.g., from 0.01 to 0.1 mm).

In some of any of the respective embodiments described herein, the composition is in a form of porous structure (e.g., a flexible or rigid porous structure), optionally an aerogel and/or foam. The porosity (i.e., percentage of the volume of the structure which consists of voids) is optionally at least 50% (e.g., from 50% to 99% or from 50% to 90%), optionally at least 60% (e.g., from 60% to 99% or from 60% to 90%), optionally at least 70% (e.g., from 70% to 99% or from 70% to 90%), optionally at least 80% (e.g., from 80% to 99% or from 80% to 90%), and optionally at least 90% (e.g., from 90% to 99%). The density of the porous structure (including voids) when dry is optionally no more than 0.5 gram/cm$^3$ (e.g., from 0.01 to 0.5 gram/cm$^3$ or from 0.1 to 0.5 gram/cm$^3$), optionally no more than 0.4 gram/cm$^3$ (e.g., from 0.01 to 0.4 gram/cm$^3$ or from 0.1 to 0.4 gram/cm$^3$), no more than 0.3 gram/cm$^3$ (e.g., from 0.01 to 0.3 gram/cm$^3$ or from 0.1 to 0.3 gram/cm$^3$), no more than 0.2 gram/cm$^3$ (e.g., from 0.01 to 0.2 gram/cm$^3$ or from 0.1 to 0.2 gram/cm$^3$), and no more than 0.1 gram/cm$^3$ (e.g., from 0.01 to 0.1 gram/cm$^3$).

The composition according to any of the respective embodiments described herein may optionally be, but is not necessarily, prepared according to a method of preparing a composition described herein.

Process:

According to an aspect of some embodiments of the invention, there is provided a method of preparing a composition comprising mycelium of a fungus as described herein in any of the respective embodiments and an additional substance, such as cellulose and/or a plurality of nanoparticles, as described herein in any of the respective embodiments. The method comprises inoculating a liquid medium with the fungus (e.g., using a fungal spore and/or small portion of mycelium), the liquid medium comprising nutrients and the additional substance, thereby obtaining the composition comprising mycelium and additional substance. The composition comprising mycelium and additional substance is also referred to herein interchangeably as a "hybrid" or "hybrid material".

In some of any of the respective embodiments described herein, the liquid medium comprising a plurality of nanoparticles (e.g., nanoparticles according to any of the respective embodiments described herein). In some such embodiments, the obtained composition is a composition comprising mycelium and nanoparticles according to any of the respective embodiments described herein.

In some of any of the respective embodiments described herein, the liquid medium comprising a cellulose (e.g., a cellulose according to any of the respective embodiments described herein). In some such embodiments, the obtained composition is a composition comprising mycelium and cellulose according to any of the respective embodiments described herein.

In some of any of the respective embodiments, the additional substance (e.g., cellulose and/or nanoparticles) becomes incorporated (as defined herein) within the mycelium, following inoculation of the liquid medium with the fungus.

In some of any of the respective embodiments described herein, the nutrients in the medium suppress cellulase activity of the fungus; e.g., such that the cellulose included in the medium is not digested by the fungus.

In some of any of the respective embodiments described herein, the nutrients comprise at least one monosaccharide and/or disaccharide (e.g., glucose or a disaccharide comprising a glucose moiety). In some such embodiments, the nutrients comprise at least one monosaccharide. In some embodiments, the monosaccharide comprises glucose.

It is to be appreciated that the use of cellulose when nutrients are also provided distinguishes the method according to some embodiments from methods which utilize materials comprising cellulose as an energy source for the fungus.

In some of any of the respective embodiments described herein, the nutrients in the medium are in a form of a biomass (e.g., a waste material), optionally a lignocellulose (e.g., wood chips, sawdust and/or pulp fibers). In some such embodiments, any additional substance added to the medium (according to any of the respective embodiments described herein), such as cellulose (e.g., nanocellulose) and/or nanoparticles, is in a form which is at least partially resistant to digestion by the fungus, for example, a crystalline cellulose (e.g., CNCs); e.g., such that any cellulose included in the medium as an additional substance (according to any of the respective embodiments described herein) is distinct from, and is not digested along with, the biomass which serves as nutrients. The biomass is optionally only partially digested during mycelium growth, e.g., such that the remaining biomass may provide structural support to the mycelium.

Without being bound by any particular theory, it is believed that cellulose (e.g., nanocellulose) which is not digested may enhance the properties of the composition (relative to corresponding compositions comprising mycelium and biomass as an energy source, without nanocellulose) by enhancing water-holding capacity (optionally enhancing mycelium development and colonization of the biomass) and/or by enhancing mechanical properties (e.g., by incorporation of the nanocellulose into the mycelium).

In some of any of the respective embodiments described herein, the method comprises incubating the fungus in the liquid medium for a period of time sufficient to allow incorporation of at least a portion of the additional substance (e.g., cellulose and/or nanoparticles) according to any of the respective embodiments described herein in the liquid medium (according to any of the respective embodiments described herein) into the mycelium; for example, for a period of time sufficient to allow incorporation of at least 1% (e.g., from 1% to 99%), or at least 3% (e.g., from 3% to 99%), or at least 10% (e.g., from 10% to 99%), or at least 20% (e.g., from 20% to 99%), at least 30% (e.g., from 30% to 99%), at least 40% (e.g., from 40% to 99%), at least 50% (e.g., from 50% to 99%), at least 60% (e.g., from 60% to 99%), at least 70% (e.g., from 70% to 99%), at least 80% (e.g., from 80% to 99%), or at least 90% (e.g., from 90% to 99%), of the additional substance in the liquid medium into the mycelium.

In some of any of the respective embodiments described herein, the method further comprises killing the mycelium (e.g., to terminate the mycelium growth), optionally by heat treatment, dehydration, and/or chemical treatment.

In some of any of the respective embodiments described herein, the method further comprises drying the composition, e.g., to obtain a solid substance.

In some of any of the respective embodiments described herein, the method further comprising homogenizing the mycelium so as to obtain a homogenized composition comprising mycelium as well as the additional substance (e.g., cellulose and/or nanoparticles). Homogenization may optionally be effected prior to drying (e.g., wherein a homogenized liquid composition is dried) and/or subsequent to drying.

In some of any of the respective embodiments described herein, an initial concentration of the additional substance (e.g., cellulose and/or nanoparticles) according to any of the respective embodiments described herein in the liquid medium (i.e., the concentration upon initial contact with the mycelium) is at least 0.05 weight percent, or at least 0.1 weight percent, or at least 0.2 weight percent, or at least 0.5 weight percent, or at least 1 weight percent, or at least 2 weight percent.

In some of any of the respective embodiments described herein, an initial concentration of the additional substance (e.g., cellulose and/or nanoparticles) according to any of the respective embodiments described herein in the liquid medium (i.e., the concentration upon initial contact with the mycelium) is no more than 5 weight percent (e.g., from 0.05 to 5 weight percent or from 0.1 to 5 weight percent or from 0.2 to 5 weight percent or from 0.5 to 5 weight percent or from 1 to 5 weight percent or from 2 to 5 weight percent), or no more than 2 weight percent (e.g., from 0.05 to 2 weight percent or from 0.1 to 2 weight percent or from 0.2 to 2 weight percent or from 0.5 to 2 weight percent or from 1 to 2 weight percent), or no more than 1 weight percent (e.g., from 0.05 to 1 weight percent or from 0.1 to 1 weight percent or from 0.2 to 1 weight percent or from 0.5 to 1 weight percent), or no more than 0.5 weight percent (e.g., from 0.05 to 0.5 weight percent or from 0.1 to 0.5 weight percent or from 0.2 to 0.5 weight percent), or no more than 0.25 weight percent e.g., from 0.05 to 0.25 weight percent or from 0.1 to 0.25 weight percent).

In some of any of the respective embodiments described herein, the method further comprises shaping the obtained composition, for example, by forming a layer (e.g., a layer according to any of the respective embodiments described herein) and/or by forming a porous structure (e.g., a porous structure according to any of the respective embodiments described herein).

Hybrid materials described herein may optionally be processed by a variety of techniques; including, for example, heat treatment to kill the mycelium; pressing (e.g., by hot press); perforation and/or cutting; and/or mixture of the hybrid material with biomass (e.g., wood-based mass such as wood chips and/or sawdust), optionally biomass digestible by the mycelium. Processing may optionally be effected locally so as to selectively alter properties of the hybrid material in a selected region (e.g., enhanced permeability by perforation or reduced permeability by hot press).

By varying content and type of the additional substance, fungal species, growth conditions, and/or material processing and post-processing approaches, a variety of types and/or properties of mycelium-based hybrid materials may optionally be obtained.

According to an aspect of some embodiments of the invention, there is provided a composition comprising mycelium and an additional substance (e.g., a plurality of nanoparticles and/or a cellulose), the composition being obtainable according to the method described herein of preparing a composition comprising mycelium and an additional substance (according to any of the respective embodiments described herein).

Applications:

Hybrid materials such as described herein (according to any of the respective embodiments) may optionally be regarded as a modified form of mycelium, whereby the additional substance (e.g., nanoparticles and/or cellulose) incorporated within the mycelium results in modified properties such as enhanced mechanical strength. For example, enhanced mechanical properties of the hybrid material may optionally result in a more durable substance than pure mycelium, which may enhance longevity and/or allow use under a wider variety of conditions.

Alternatively or additionally, hybrid materials such as described herein (according to any of the respective embodiments) may be regarded as a modified form of the additional substance, for example, a modified form of cellulose (e.g., nanocellulose), whereby the mycelium covering the additional substance (e.g., cellulose) results in modified properties, such as enhanced water resistance.

Thus, such hybrid materials may optionally be used in applications known in the art for either mycelium or the additional substance (e.g., nanocellulose, pulp fibers).

In some of any of the respective embodiments described herein, a hybrid material described herein (according to any of the respective embodiments) is used a raw material for the preparation of various articles-of-manufacture (e.g., according to any of the embodiments described herein relating to an article-of-manufacture).

In some of any of the respective embodiments described herein, a hybrid material described herein (according to any of the respective embodiments) is used in agriculture.

In some of any of the respective embodiments described herein, a hybrid material described herein (according to any of the respective embodiments) is used in promoting symbiosis with a plant (e.g., mycorrhiza formation); for example, wherein the hybrid material comprises live fungus.

In some of any of the respective embodiments described herein, a hybrid material described herein (according to any of the respective embodiments) is used in facilitating hydroponic growth. In some such embodiments, the hybrid material floats on water. In some embodiments, the hybrid material which floats on water has a porous structure according to any of the respective embodiments described herein.

In some of any of the respective embodiments described herein, a hybrid material described herein (according to any of the respective embodiments) is used in preparation of biodegradable devices. In some embodiments, the biodegradable device is a disposable device (e.g., for using once) which can degrade in place without requiring removal (e.g., as would be required for devices prepared from conventional materials), such as planters, multi-cell trays, containers and/or tree protectors.

In some of any of the respective embodiments described herein, a hybrid material described herein (according to any of the respective embodiments) is for gradually releasing plant nutrients via release of any material (e.g., natural or synthetic fertilizer), for example, in the preparation of a compost. The plant nutrients may optionally be embedded in the hybrid material and/or be released via degradation of the mycelium (e.g., thereby releasing nitrogen-containing compounds), for example, degradation of a biodegradable device according to any of the respective embodiments described herein. Alternatively or additionally, the plant nutrients may optionally be produced via gradual digestion of a substrate (e.g., wood or similar material) to release natural compounds (e.g., saccharides), for example, wherein the hybrid material comprises live fungus.

In some of any of the respective embodiments described herein, a hybrid material described herein (according to any of the respective embodiments) is used for providing a controlled environment for a plant (e.g. a plant root, seed, seedling and/or cutting), before and/or after planting. The controlled environment may comprise, for example, physical protection and/or a high level of moisture. Such a controlled environment may optionally be in order to enhance plant yield and/or to enhance plant development.

In some of any of the respective embodiments described herein, a hybrid material described herein (according to any of the respective embodiments) is used for bioremediation, for example, in which the hybrid material comprises fungus in a live form and the fungus in the hybrid material accumulates or breaks down a pollutant.

In some of any of the respective embodiments described herein, a hybrid material described herein (according to any of the respective embodiments) is processed by a technique such as used for preparing molded pulp products (e.g., from recycled paper or paperboard). Examples of products prepared from molded pulp, which may also be prepared from a hybrid material according to embodiments of the invention, include, without limitation, packaging material, egg cartons, trays (e.g., food trays, egg trays, pallet trays), plates, bowls, beverage carriers, end caps, clamshell containers, slipper pans and urinals.

In some of any of the respective embodiments described herein, a hybrid material according to any of the respective embodiments described herein is used in circular production systems. A non-limiting example of a circular production system comprises using agricultural waste material (e.g., pruning waste) as a source of cellulose for production of hybrid materials used in agricultural (e.g., in an agricultural device or soft engineering described herein), whereupon the hybrid material may decompose and further promote plant growth.

Article-of-Manufacture:

According to an aspect of some embodiments of the invention, there is provided an article-of-manufacture comprising a composition according to any of the respective embodiments described herein.

The article-of-manufacture may be any type of article-of-manufacture which can be produced from mycelium and/or the additional substance according to any of the respective embodiments described herein; for example, cellulose (e.g., nanocellulose) and/or nanoparticles within the composition (according to any of the respective embodiments described herein).

The article-of-manufacture may also be any type of article-of-manufacture which comprises a film and/or porous material (e.g., aerogel and/or foam).

In some of any of the respective embodiments described herein, the article-of-manufacture comprises packaging material. The packaging material is optionally in a form of a film, for example, for applications in which a plastic film and/or paper is commonly used. Alternatively or additionally, the packaging material is a porous packaging material, for example, for applications in which a polystyrene foam is commonly used, such as disposable boxes and trays. The packaging material is optionally prepared by a technique such as used for preparing molded pulp products.

In some of any of the respective embodiments described herein, the article-of-manufacture comprises a foam; for example, a sponge, a foam used for cushioning, and/or a foam used for insulation. The foam may be a resilient (elastic) foam or non-resilient (non-elastic) foam.

In some of any of the respective embodiments described herein, the article-of-manufacture is a hygiene product (e.g., comprising a hybrid material having a porous structure according to any of the respective embodiments described herein), for example, an absorbent hygiene product. Examples of suitable hygiene products include without limitation, diapers, tampons, cleansing pads, wet wipes, toilet paper, and towels.

In some of any of the respective embodiments described herein, the article-of-manufacture is a textile (woven and/or non-woven). In some such embodiments, the hybrid material is used to forms fibers which are then used to prepare a woven or non-woven textile, using any technique known in the art to prepare a fiber and/or a textile from a fiber. In some embodiments, the hybrid material forms a non-woven mat, e.g., wherein the hyphae of the mycelium serve as fibers of the non-woven textile.

In some of any of the respective embodiments described herein, the article-of-manufacture is an article of clothing or portion thereof. The article of clothing or portion thereof may optionally be of a type commonly produced from leather or leather substitutes, such as belts, gloves, straps, and the like (e.g., wherein the hybrid material serves as a leather substitute), and/or of a type commonly produced from textiles (e.g., wherein the hybrid material serves as a textile).

In some of any of the respective embodiments described herein, the article-of-manufacture is a footwear (e.g., shoe, boot and/or sandal). In some such embodiments, the hybrid material serves as a leather substitute and/or as a woven or non-woven textile (according to any of the respective embodiments described herein).

In some of any of the respective embodiments described herein, the article-of-manufacture is a container (e.g., a food container, egg carton or egg tray, and/or a clamshell container) and/or tableware (e.g., a food tray, a plate and/or a bowl). The container is optionally prepared by a technique such as used for preparing molded pulp products.

In some of any of the respective embodiments described herein, the article-of-manufacture is a planter (i.e., a box or pot for plants) or multi-cell tray for plants (e.g., for growing small plants such as seedlings or liners). The multi-cell tray may optionally be configured such that different cells in the tray may be readily detached from one another; for example, by adapting the mechanical properties and width of the portion linking between different cells.

In some of any of the respective embodiments described herein, the article-of-manufacture is a tree protector (e.g., a biodegradable tree protector). The tree protector may optionally be an approximately tubular structure for surrounding young trees in tree plantations or elsewhere. Alternatively, the tree protector may optionally be a tile-like structure for covering the ground adjacent to a tree. The tree protector according to any of the respective embodiments described herein may optionally be porous and/or water-absorbent.

In some of any of the respective embodiments described herein, the article-of-manufacture is a food or food supplement. In some such embodiments, the hybrid comprises cellulose, and the cellulose serves as a dietary fiber.

In some of any of the respective embodiments described herein, the article-of-manufacture is a flame retardant.

In some of any of the respective embodiments described herein, the article-of-manufacture comprises a barrier element (e.g., a barrier against a liquid, such as water and/or oil; and/or air); for example, a coating, a container wall, a platform (e.g., a tray or plate), and/or a packaging material (e.g., a paper-substitute) which comprises the composition. In some embodiments, the barrier element is configured for serving as a barrier against an aqueous liquid and/or hydrophobic liquid (e.g., oil).

The article-of-manufacture may optionally be configured for use in agriculture (including horticulture). Such articles-of-manufacture may, for example, be used once and undergo biodegradation (e.g., when the hybrid composition comprises cellulose and/or a biodegradable nanoparticle in addition to mycelium) rather than be removed (as would typically be required for corresponding plastic products). For example, a planter may optionally be buried in soil upon planting (e.g., in the ground or in a larger planter), optionally providing a controlled environment after planting, avoiding potential damage associated with removal from a planter, and/or simply reducing the work, waste and/or costs involved in planting. Similarly, a multi-cell tray may optionally be separated into individual cells which may each be buried in soil (as described herein for a planter). Besides biodegradability, additional (or alternative) advantages (e.g., relative to typical plastic products) include, for example, a high water-holding capacity, which may be particularly useful for agricultural devices; porosity, which may facilitate water-holding capacity and/or root growth into the material (e.g., for reducing root entanglement, which may be harmful to the plant); and/or natural fertilization (e.g., by gradual release of nutrients via digestion of a substrate (e.g., wood or related material) by the mycelium (e.g., a biomass incorporated within a composition according to any of the respective described herein) and/or by decomposition of the mycelium by organisms in the soil).

A planter and/or multi-cell tray may optionally be configured as a root trainer, that is, a container shaped (e.g., by suitable ribs, ledges, overall shape and/or holes) to promote root formation in a manner advantageous to future planting, for example, by enhancing root branching, directing root tips towards openings, and/or reducing formation of particularly long roots (which may be regarded as similar to pruning long roots without creating a wound).

Enhancement of Fungus Growth:

As exemplified in the Examples section herein, the present inventors have uncovered that substances such as carboxymethylated cellulose can surprisingly enhance the yield of mycelium, even when the mycelium is grown under conditions (e.g., abundance of nutrients) which suppress cellulose digestion (such that the cellulose is not serving to any significant degree as a nutrient).

According to an aspect of some embodiments of the invention, there is provided a method of enhancing growth of a fungus, the method comprising contacting the fungus with a liquid medium comprising a polymer which comprises carboxylic acid groups.

Enhancement of mycelium growth according to any of the respective embodiments described herein may optionally be utilized when preparing hybrid materials such as described herein (according to any of the respective embodiments), as well as when growing fungi for any other purpose (e.g., for bioremediation; for agriculture; for biosynthesis of metabolic products such as antibiotics, proteins, exopolysaccharides; and/or for biomedical products and supplements).

The fungus according to this aspect may optionally comprise a fungus characterized by a mycelium (e.g., a fungus according to any of the respective embodiments described herein) and/or a fungus which is not characterized by a mycelium (e.g., a fungus which grows as single cells).

In some of any of the embodiments described herein, the polymer comprises cellulose modified to include carboxylic acid groups (e.g., according to any of the respective embodiments described herein), optionally carboxymethylated cellulose.

In some of any of the respective embodiments described herein, at least a portion of the cellulose (e.g., carboxymethylated cellulose) is in a form of nanofibrils (e.g., carboxymethylated CNFs according to any of the respective embodiments described herein).

In some of any of the embodiments described herein, a viscosity of the liquid medium is at least 10 cP (e.g., from 10 to 100000 cP or from 10 to 10000 cP), optionally at least 100 cP (e.g., from 100 to 100000 cP or from 100 to 10000 cP), optionally at least 1000 cP (e.g., from 1000 to 100000 cP or from 1000 to 10000 cP), and optionally at least 10000 cP (e.g., from 10000 to 100000 cP).

Viscosity (according to any of the respective embodiments described herein) is optionally determined at a temperature at which growth is effected, and/or at a temperature of 25° C.

In some of any of the embodiments described herein, the growth occurs under conditions wherein the fungus does not digest the polymer. For example, in any of the embodiments wherein the polymer comprises cellulose, growth is optionally under conditions which suppress cellulose digestion by the fungus (e.g., by suppressing cellulase activity), for example, in the presence of appropriate nutrients (according to any of the respective embodiments described herein).

Additional Definitions

It is expected that during the life of a patent maturing from this application many relevant applications and techniques utilizing fungus and/or mycelium will be developed and the scope of the terms "fungus", "mycelium" and "article-of-manufacture" are intended to include all such new technologies a priori.

As used herein the term "about" refers to ±10%.

The terms 'comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials

Culture of *Trametes ochracea* (also known as *Trametes multicolor*), a white-rot basidiomycetes fungus, was obtained from Mycelia NV (Belgium) and stored at 4° C.

The following standard reagents an materials were obtained from Sigma-Aldrich: D-glucose, peptone, yeast extract, malt extract, $KH_2PO_4$, $K_2HPO_4$, and $MgSO_4$ (for fungal growth media); NaOH; monochloric acetic acid; ethanol; isopropanol; methanol; sodium hydrogen carbonate; polyallylamine hydrochloride (PAH); and regenerated cellulose dialysis membranes (76 mm, 12-14 kDa MW cut-off).

Spray dried cellulose nanocrystals (CNCs), prepared by sulfuric acid hydrolysis of bleached softwood, were obtained from CelluForce.

Never-dried bleached softwood pulp (Dissolving Pulp Plus) was obtained from Domjsö-MORE, and was used as the cellulose source for various cellulose nanofibril (CNF) grades.

Mono-component endoglucanases (FiberCare®) used to pretreat the pulp for the enzymatic grade CNFs) was obtained from Novozymes.

Nanocellulose (NC) Processing and Production:

(I) Spray-dried cellulose nanocrystal (CNC) powder was combined with purified water (obtained via Milli-Q® system) to 2% consistency by overhead mixing, followed by probe sonication at 5000 J/g, and vacuum filtration using a Grade 3 filter (Munktell). This CNC grade has been thoroughly characterized in the literature and has a surface charge from sulfate half-ester groups of approximately 250 µeq/g [Reid et al., *Langmuir* 2017, 33:1583-1598].

(II) Carboxymethylated cellulose nanofibrils (CNFs) were produced according to procedures described by Wigberg et al. [*Langmuir* 2008, 24:784-795] to obtain a suspension with a degree of substitution (DS) of 0.1, or equivalently ca. 600 µeq/g, with DS defined in equation 1.

$$\frac{AGU\ MW\left(160\frac{g}{mol}\right)}{\left[\frac{1}{\text{Total charge}} - CH_3COONa\ MW\left(80\frac{g}{mol}\right)\right]} \qquad \text{Equation 1}$$

where AGU refers to anhydroglucose unit, and total charge is measured by the titration of an acidified suspension with sodium hydroxide. To achieve CNFs from the carboxymethylated pulp, the material was homogenized at 1700 bar, using an M-110EH Microfluidizer® processor (Microfluidics Corp.) with 1 pass (1p) through the homogenizer or 4 passes (4p) for a finer grade. The DS 0.3 carboxymethylated CNF (ca. 1700 µeq/g) used in this work was prepared in the same fashion as the DS 0.1 CNFs with the following modifications: a 4.4-fold increase in monochloric acetic acid content and 2.7-fold increase in sodium hydroxide.

(III) Enzymatically pretreated cellulose nanofibrils (CNFs) were produced from bleached softwood pulp treated with a mono-component endoglucanase, according to procedures described in detail by Henriksson et al. [*Eur Polym*

*J* 2007, 43:3434-3441], followed by 10 passes through the Microfluidizer® processor at 1700 bar. The enzymatic CNFs have a low negative total charge of ~30 µeq/g.

Nanocellulose (NC) Nano-Yield:

Approximate nano-yields of the NC samples were measured by high speed centrifugation (at 1000 g) of dilute suspensions (0.02 wt %, 1 liter volume, divided) for 20 minutes. Comparison of the solid content of the supernatant, containing the nm-scale NC, to the total solid content of the initial suspension, gives the nano-yield (%). As described, the nano-yield of the CNF samples was ca. 50-80% and 100% for the CNCs.

Mycelium Cultures:

*T. ochracea* was maintained in Petri dishes (85 mm-diameter) containing malt-agar. The malt-agar contained: agar (15 g), peptone (10 g), and malt extract (30 g), dissolved in deionized water (1 L) [Livne et al., *J Mater Chem B* 2019, 7:5725-5731].

Fungal Culture Conditions:

For pure *T. ochracea* culture, the following medium was used, as has been previously detailed by Livne et al [*J Mater Chem B* 2019, 7:5725-5731]: D-glucose (15 g), peptone (2.5 g), yeast extract (3 g), $KH_2PO_4$ (1 g), $K_2HPO_4$ (0.2 g), and $MgSO_4$ (0.5 g) dissolved in 1 liter deionized water and adjusted to pH 5.5. 8 mycelium disks (6 mm-diameter) cut from malt agar plates were used as inoculum for the incubations that were conducted in a 1 liter flask containing 600 ml medium for 14 days under a controlled conditions (50% relative humidity, 23° C.), in the dark, with continuous shaking at 120 rpm.

In order to terminate the mycelium growth, the mixtures were autoclaved (121° C., 1 hour). The pH after incubation and autoclave was observed to drop slightly to pH 5 for all samples. To remove excess salts and unconsumed nutrients, the autoclaved mixtures (pellets and surrounding liquid) were dialyzed for 2 days under running deionized water. In order to process into films or aerogels, the dialyzed liquid cultures were homogenized using a Polytron® PT 3100D homogenizer at 7500 rpm for 2 minutes.

Nanocellulose (NC)-Mycelium Co-Incubation:

The co-incubated samples were prepared as described above for the fungal incubations, with one exception: the water in the liquid medium was replaced with NC suspensions of different concentrations, ranging from 0.2-2 wt %. These NC-containing mixtures were thoroughly combined by magnetic stirring prior to autoclaving to encourage the uniform dispersal of the NC.

High Resolution Scanning Electron Microscopy (HR-SEM):

An Ultra Plus™ scanning electron microscope (Zeiss), equipped with a Schottky field-emission electron gun and a Gemini™ electron-beam column design, was used. The microscope was operated at low acceleration voltages of 1.5-2 kV and working distances of 3.5-4.5 mm. Everhart-Thornley secondary electron imaging detectors or high-resolution in-the-lens secondary electron detectors were used to acquire images. To improve electrical conductivity, samples were coated—using a Q150TES coating device (Quorum)—with several nanometers of carbon, using short pulses of low evaporation current to prevent organic material degradation. Pellets produced through the various incubations were submerged in ethanol overnight to solvent exchange, followed by critical point drying (CPD). Using tweezers, dried pellet pieces were carefully transferred to SEM stubs covered with carbon tape for imaging.

Cryo-Scanning Electron Microscopy (Cryo-SEM):

An Ultra Plus™ scanning electron microscope (Zeiss), equipped with a Schottky field-emission gun and with a Bal-Tec™ VCT100 cold-stage system maintained below −145° C., was used for cryo-SEM imaging. Specimens were imaged at low acceleration voltages of 1-1.4 kV and working distances of 3.5-5 mm. Everhart-Thornley secondary electron imaging detectors were used. Low-dose imaging was applied to all specimens to minimize radiation damage. Specimens were prepared by placing a mycelium pellet into a cross-sectional stub, which was then immersed into liquid ethane at −183° C. and transferred into liquid nitrogen to be screwed into a specialized sample table. Next, the frozen sample was transferred into a BAF060 freeze fracture system, where the pellets were fractured using a rapid stroke from a cooled knife to expose their inner structure. Following the fracturing, the sample was transferred into the precooled HR-SEM for imaging as described above. Imaging was performed as close as possible to the pellet surface, where the cooling rate is maximal. If needed, gentle sample sublimation was done inside the microscope by rapidly increasing the stage temperature to −100° C. and then decreasing it back to the initial temperature.

Atomic Force Microscopy (AFM):

(I) AFM images of NC and of mycelium materials were collected under ambient conditions using a MultiMode™ 8 AFM system (Bruker) with TappingMode™ imaging and RTESP-150 cantilevers having a nominal resonant frequency of 150 kHz and a spring constant of 5 N/m, respectively. Mycelium samples were prepared by spin coating onto plasma-cleaned cleaved silica wafers. For anionic NC samples, wafers were first coated with polyallylamine hydrochloride (0.1 wt %) followed by thorough rinsing. (II) The roughness of hybrid films was obtained from tapping mode images using a FastScan™ AFM system (Bruker) and a Tap300DLC AFM probe, with spring constant and actual tip outer radius calibrated prior to measurements. The DMT modulus was fitted to obtain the nanomechanical maps (obtained in PeakForce mode) used to calculate the average elastic moduli of the samples.

X-Ray Photoelectron Spectroscopy (XPS):

XPS spectra were recorded using an AXIS Ultra™ DLD x-ray photoelectron spectrometer (Kratos Analytical). The samples were analyzed using a monochromatic Al x-ray source, at a depth of ~10 nm and a lateral resolution of ~1 $mm^2$, with most of the signal from an area of ~700×300 µm. Survey spectra were run to detect elements present in the surface layer and relative surface compositions (expressed in atomic %) were then obtained from quantification of detailed spectra run for each element detected. In addition, high-resolution carbon spectra were curve-fitted, showing chemical shifts in the carbon signals due to different functional groups.

Attenuated Total Reflectance-Fourier Transform Infrared (ATR-FTIR) Spectroscopy:

A Spectrum One™ FT-IR spectrometer (Perkin Elmer) with attenuated total reflectance (ATR) accessory and diamond ATR crystal was used characterize the chemical signature of the fungal materials.

Polarized Optical Microscopy (POM):

An Axioplan™ polarized optical microscope (Zeiss) equipped with a 540 nm waveplate was used to visualize the various materials produced in this study (NC, pellets, surrounding liquid, homogenized mixtures, films, and aerogels) and to contrast between the non-birefringent hyphal network and birefringent NC.

Ultraviolet-Visible (UV-Vis) Spectroscopy:

UV-Vis spectroscopy was conducted to assess turbidity/stability by measuring absorbance at 550 nm as a function of time (0 hour and 12 hours), with and without dilution.

Liquids were placed into standard plastic cuvettes (10 mm path length) and absorbance was measured using a LAMBDA™ 265 UV/Vis spectrophotometer, with water used as a blank.

Example 1

Material Obtained by Co-Incubation of Mycelium with Nanocellulose

*T. ochracea* was grown in agitated liquid culture with nanocellulose (NC) uniformly dispersed within the growth medium concomitantly with the fungal inoculation. As the growth medium was rich in available nutrients, including readily digestible glucose, cellulase secretion was expected to be suppressed [Alfaro et al., *Sci Rep* 2020. 10:12421] and the NC was not expected to be digested. The effect of NC on the resultant mycelium under such conditions was investigated. The various types of NC used in the investigation, cellulose nanofibers (CNFs) and crystalline nanocellulose, are shown in FIGS. 1A-1D.

Most incubations proceeded via the formation of pellets, multiplying over time and accompanied by a thickening of the surrounding liquid media due to secreted exopolysaccharides (EPS) and proteins [Appels et al., *Sci Rep* 2018, 8:4703; Ruiz-Herrera & Ortiz-Castellanos, *Cell Surf* 2019, 5:100022].

As shown in FIGS. 2A-2F and 3A-3F, the fungal pellets were generally spherical, with diameters in the mm to cm range; with the exception of samples co-incubated with 2% CNCs (cellulose nanocrystals), which formed exceptionally small and oblong pellets (as shown in FIG. 3E).

The only co-incubation that did not produce pellets was with 2% carboxymethylated CNFs (cellulose nanofibrils), apparently because the high viscosity of this sample restricted flow, such that initial mycelium development occurred at the air-liquid interface and development within the liquid phase only occurred after manual agitation of the flask.

As further shown in FIGS. 2A-2F, pellet size and appearance varied across samples (even among replicates), ranging from smooth textures to rough surfaces with fingerlike protrusions, but were consistent within each incubation flask.

The color, consistency, and morphology of the mycelial aggregates obtained by submerged culture are diverse and influenced by confounding factors [Blanchette, *Annu Rev Phytopath* 1991, 29:381-403], however, some studies relate increasing broth viscosity and agitation speed to a smaller pellet size [Veiter et al., *Appl Microbiol Biothenol* 2018, 201:2997-3006; Gibbs et al., *Crit Rev Biotechnol* 2000, 20:17-48].

Pure *T. ochracea* incubations produced fewer pellets by mass (25-58 grams) at higher solid contents (7-3.1% by weight) compared to carboxymethylated CNF-mycelium bio-composites, with 108-160 grams of pellets produced (2.3-2.9% by weight) for 0.2% (by weight) CNF co-incubations, which approximately doubled to 253 grams (2.3% by weight) for a 0.5% CNF co-incubation.

These results confirm that mycelium development occurs in the presence of NC (CNCs or CNFs); and moreover, that CNFs actually enhance the growth of mycelium.

Furthermore, the microscopic morphology of the hyphae within the pellets was surprisingly influenced by the NC content, as determined by high resolution scanning electron microscopy (HR-SEM).

Figure 4A:
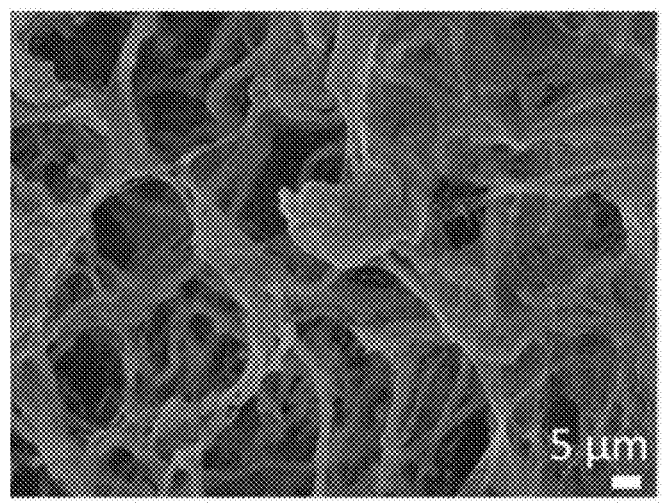
Figure 4B:
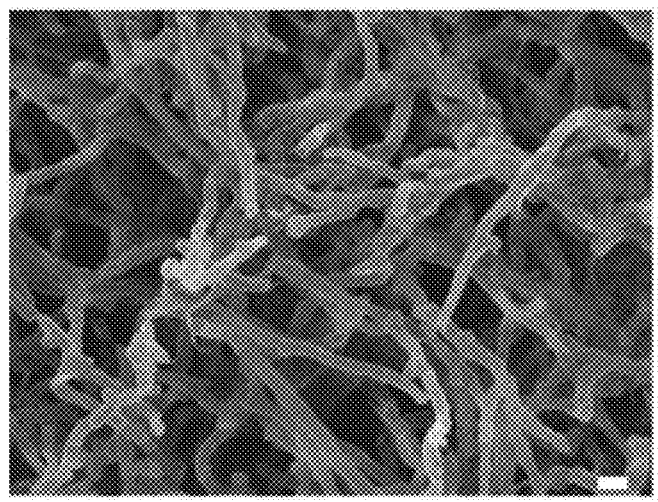
Figure 4C:

As shown in FIGS. 4A-4C, hyphae of *T. ochracea* in the absence of NC exhibit an ~2 µm-diameter branched and irregular form, covered in places by a fine web of EPS (FIG. 4A), whereas the hyphae became less branched and more regular with the addition of NC in a dose-dependent manner (FIGS. 4B and 4C), such that incubation with 2% CNFs resulted in hyphae with ~2 m diameters and smooth, continuous and spaghetti-like morphology, with fewer clear junctions (FIG. 4C).

As shown in FIGS. 5A-5C, hyphae with typical dimensions were obtained upon co-incubation with cellulose nanocrystals (CNCs), but the observed structure was dominated by nm-scale fibrillar features. These fibrillar features were also seen in other samples, but to a lesser extent.

These results indicate that incubation with NC alters the structure of hyphae; perhaps through a specific interaction between NC and mycelium, or through indirect factors, such as enhancement of viscosity by NC and consequent hindrances to mass transport and diffusivity.

Substrate type, nutrient profile, and growth conditions have been reported to exert an influence on hyphal appearance and properties [Veiter et al., *Appl Microbiol Biothenol* 2018, 201:2997-3006; Jones et al., *Process Biochem* 2019, 80:95-102; Sabantina et al., *Nanomaterials* 2019, 9:475].

Nanometer-scale NC was not clearly discernible by HR-SEM imaging. Consequently, various analyses were conducted to locate NC within the mycelium and to understand the influence of NC on the bio-composite properties. Polarized optical microscopy (POM) was used to distinguish between hyphae, which are not birefringent, and NC, which is birefringent.

As shown in FIGS. 6A and 6B, pure *T. ochracea* pellets exhibited a fine but non-birefringent hyphal network structure (FIG. 6A); whereas pellets from NC-mycelium co-incubation exhibited birefringent features, indicating the presence of NC (FIG. 6B).

Furthermore, as shown in FIGS. 7A-7F, no birefringence was detected in the surrounding liquid medium following co-incubation of mycelium and CNFs.

As further shown therein, 4p grade CNF suspensions exhibited fewer fragments observable by optical microscopy than did 1p grade CNF suspensions, confirming that the 4p grade CNF is finer than the 1p grade CNF.

As shown in FIGS. 8A and 8B, partially fibrillated micrometer scale carboxymethylated CNF fragments appear to be engulfed by hyphae.

Furthermore, as shown in FIGS. 8A and 9A-9D, for carboxymethylated CNFs, both distinct micrometer scale fibrils and assemblies of nanometer scale fibrils become fully integrated within the hyphal network, with no CNFs evidenced outside the cohesive mass generated via the co-incubation process.

As shown in FIGS. 10A-10C, similar results were observed for co-incubation with enzymatic CNF and pulp fibers, with mycelium growing on and around the cellulosic substrates.

Overall, observations by polarized optical microscopy (POM) and high resolution scanning electron microscopy (HR-SEM) suggest that NC accumulate and disperse within the mycelium pellets and become depleted or absent from the surrounding medium. Large NC fibrils (and pulp fibers) seem to act as a scaffold for mycelium growth, in ways similar to other macroscopic cellulosic substrates (e.g. woodchips, saw dust).

X-ray photoelectron spectroscopy (XPS) measurements were performed to determine atomic composition of freeze-dried pellets (both exterior surfaces, and interior surfaces exposed by fracture), a pure CNF aerogel, and films prepared by vacuum filtration after dialysis and homogenization of the liquid incubations. The results are summarized in Table 1 below. As CNFs do not contain nitrogen, all detected nitrogen was attributed to the chitin or other nitrogen containing species in the mycelium. The dilution of mycelium with NC was expected to manifest in higher O/C and lower N/C ratios for the NC-mycelium hybrids compared to pure *T. ochracea*.

However, as shown in Table 1, atomic distribution of pure *T. ochracea* mycelium and in NC-mycelium hybrids were similar, with O/C ratios of 0.59-0.65 and N/C ratios of 0.01-0.04 for pellets; and 0.48-0.49 and 0.05-0.06, respectively, for films.

The difference in O/C and N/C ratios between the pellets and films is likely related to the higher EPS content in the films, which were processed from the complete mixture of pellets and surrounding medium.

As the XPS measurements probe a depth of ~10 nm at a lateral resolution of ~1 mm$^2$, the similar values obtained whether NC was present or not, further supports the conclusion that NC is fully engulfed by mycelium, and potentially even integrated within the hyphal cell walls. Furthermore, the similar values obtained for pellet interiors and exteriors may reflect that fracture occurs between hyphal elements without NC exposure, an observation that may have implications for the mechanical behavior of the bio-composite.

As further shown in Table 1, the pure CNF aerogel had an O/C ratio that coincided with the theoretical value expected for cellulose (although the O/C for the CNF sample is expected to further deviate due to carboxymethyl surface groups).

TABLE 1

Atomic ratios of dialyzed and freeze-dried pellets, of vacuum-filtered films made from dialyzed and homogenized pellets and medium, and of CNF aerogel (control), as determined by XPS surface analysis (in all samples, CNF DS was 0.1 (1 p grade), with ~30% CNF dry content).

| Material | Atom ratio | Pellet interior | Pellet exterior | Film/aerogel Surface |
|---|---|---|---|---|
| *T. ochracea* | O/C | 0.59 | 0.65 | 0.48 (film) |
|  | N/C | 0.01 | 0.04 | 0.05 (film) |
| CNF + *T. ochracea* | O/C | 0.65 | 0.61 | 0.49 (film) |
|  | N/C | 0.02 | 0.03 | 0.06 (film) |
| CNF | O/C | — | — | 0.83 (aerogel) |
|  | N/C | — | — | — |

Similarly, exemplary films were analyzed by ATR-FTIR, which provides information regarding the film surface at a μm-scale depth of penetration.

As shown in FIG. 11, the mycelium-CNF hybrid film has mycelium-derived bands that do not occur in the pure CNF film; most notably bands at 1640 cm$^{-1}$ and 1540 cm$^{-1}$, assigned to protein, and a band at 1370 cm$^{-1}$, assigned to chitin; and the bands at 3300-2850 cm$^{-1}$ are more pronounced in mycelium-containing films, which may be due to the presence of lipids [Haneef et al., *Sci Rep* 2017, 7:41292].

It is difficult to identify entirely cellulose-derived bands in the hybrid film, which contains other carbohydrates, such as β-glucans, that have a chemical signature that overlaps with that of CNFs.

Taken together, the surface analyses presented in Table 1 and FIG. 11, indicate that compositionally similar qualities of mycelium are produced whether or not CNFs are included in the incubation, and that the mycelium signature is generally more prominent at the surface of the hybrids, including interior surfaces, further supporting the conclusion that co-incubation proceeds by the encapsulation of NC within the mycelium.

Nanoscale imaging by atomic force microscopy (AFM) provided further insights on the localization of NC and its influence on hyphal morphology. AFM images of homogenized mycelial mass (pellets+surrounding media, post-dialysis) are shown in FIGS. 12A and 12B.

Figure 12A:
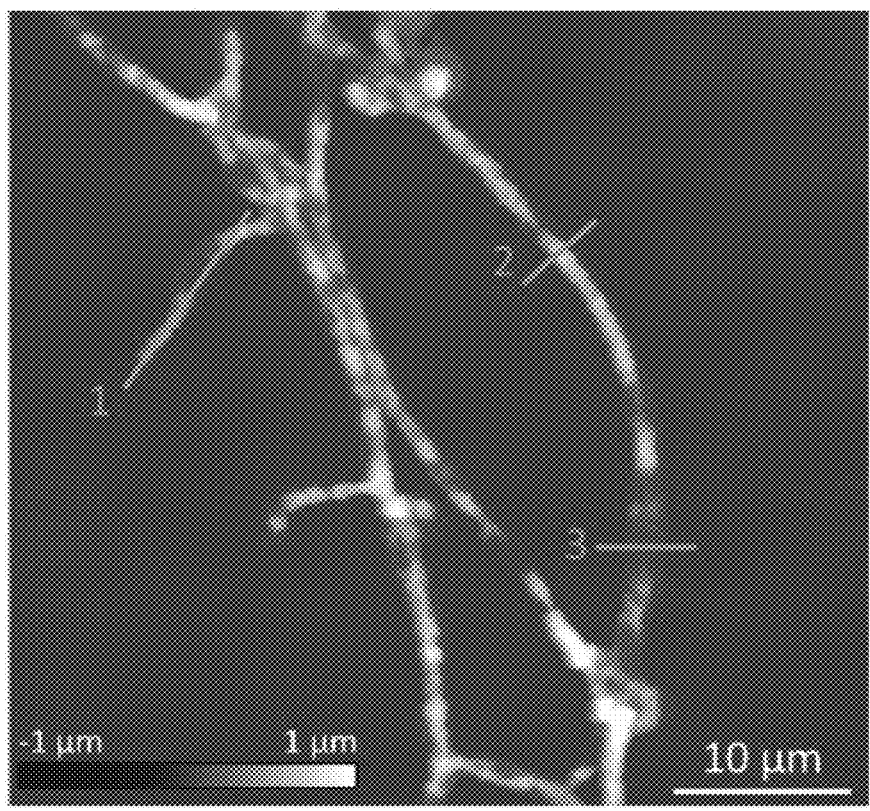
Figure 12B:
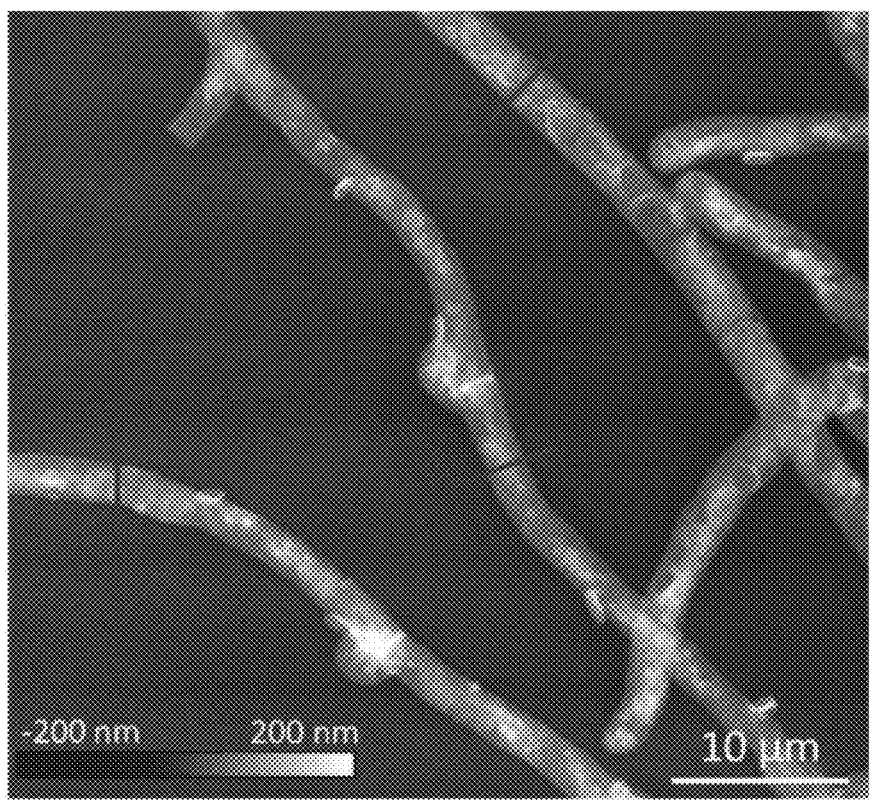

As shown in FIGS. 12A and 12B, a typical branched hyphal network, with some homogenization-induced breakages, and hyphae widths of about 2-3 μm were observed by AFM for pure *T. ochracea* (FIG. 12A) and a carboxymethylated CNF-mycelium hybrid (FIG. 12B).

Figure 12C:
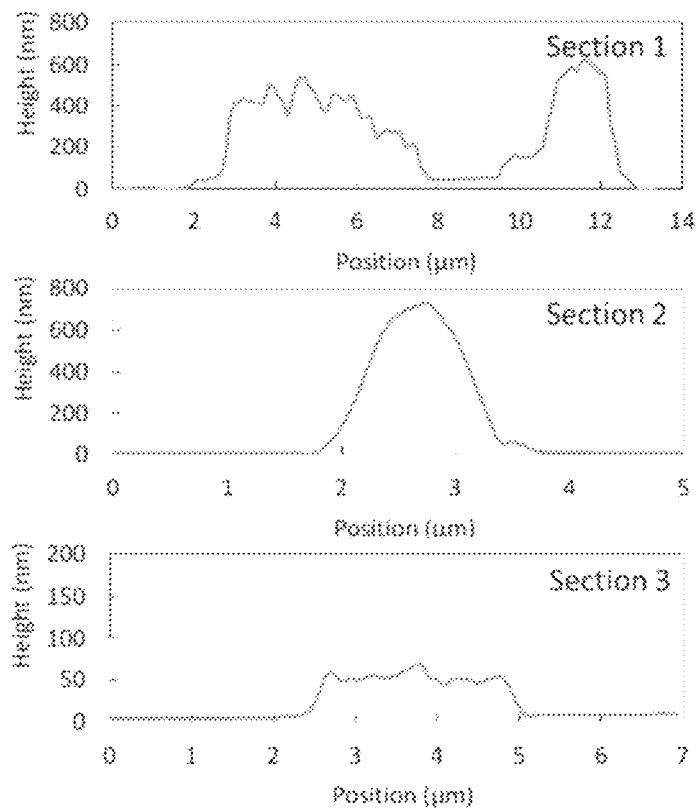
Figure 12D:
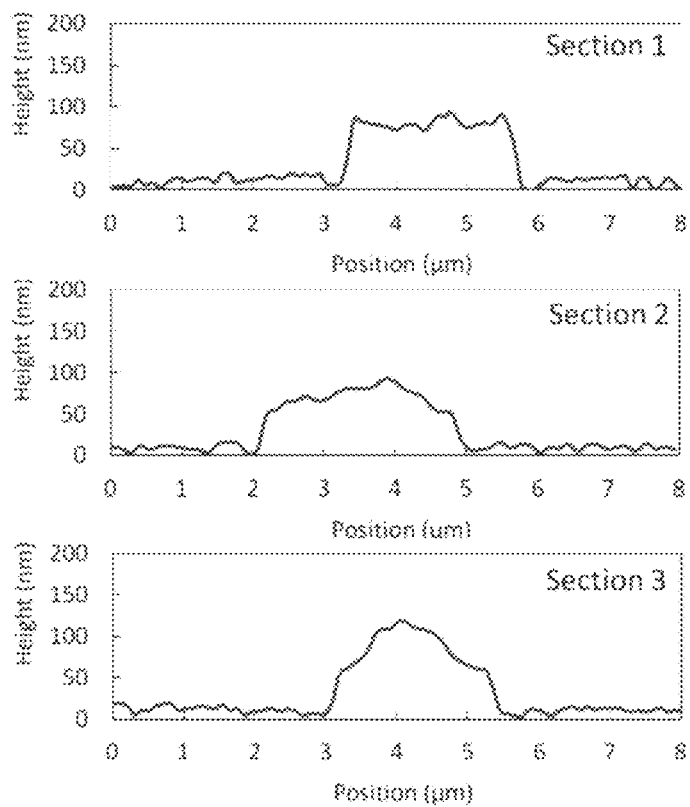

As shown in FIGS. 12C and 12D, sections along the *T. ochracea* hyphae presented low and high features, up to about 600 nm (FIG. 12C), whereas the CNF-mycelium hybrid was more uniform with a collapsed-hyphal height of about 100 nm (FIG. 12D).

These results, whereby more uniform morphologies are observed for the CNF-mycelium hybrid than for pure *T. ochracea* is generally consistent with the HR-SEM images presented in FIGS. 4A-4C.

Figure 12E:
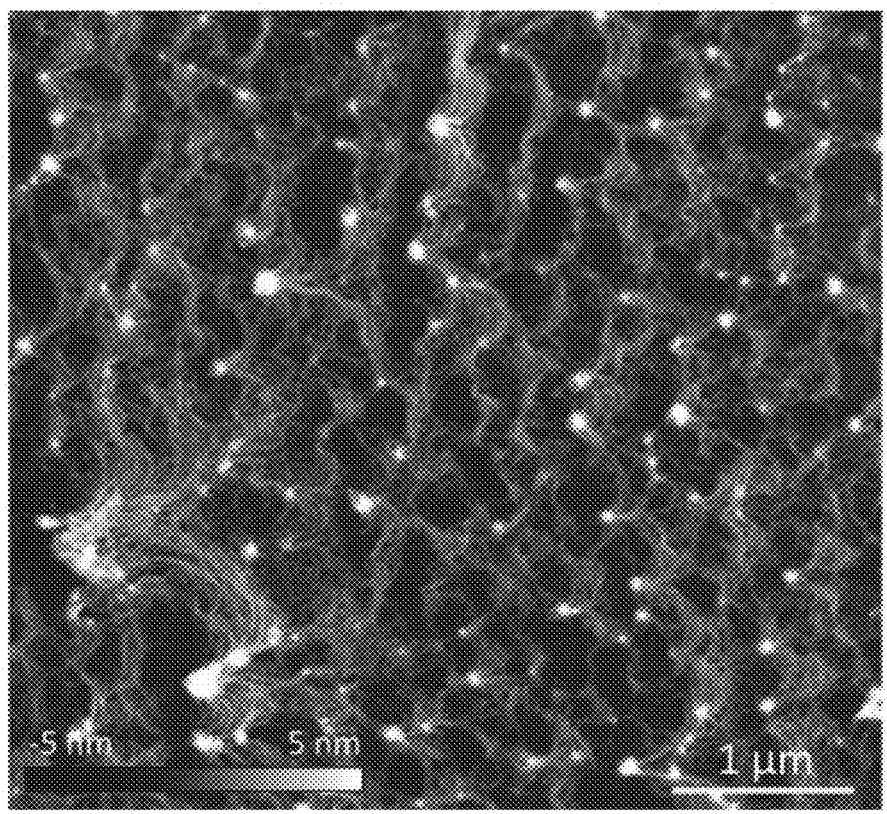
Figure 12F:
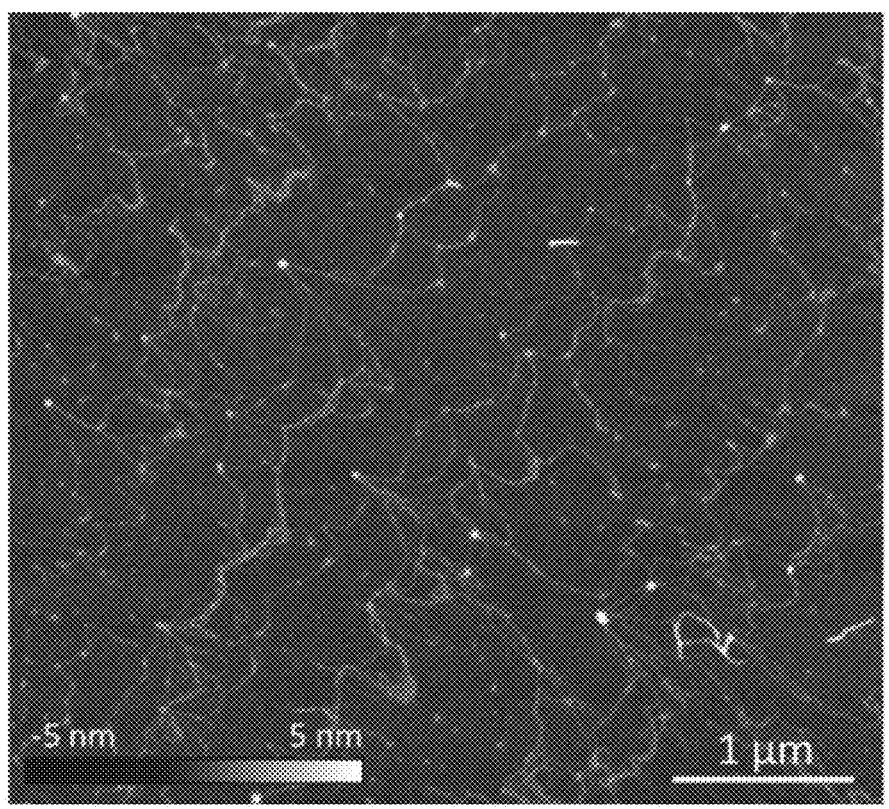

As shown in FIGS. 12E and 12F, closer inspection of the seemingly empty spaces in FIGS. 12A and 12B indicate that these regions are populated with a network of fine exopolysaccharides (EPS), with heights of about 1-3 nm. These results are consistent with previously published AFM images of fungal glucans [Puertas et al., *Fibers* 2014, 2:255-263].

Figure 13A:
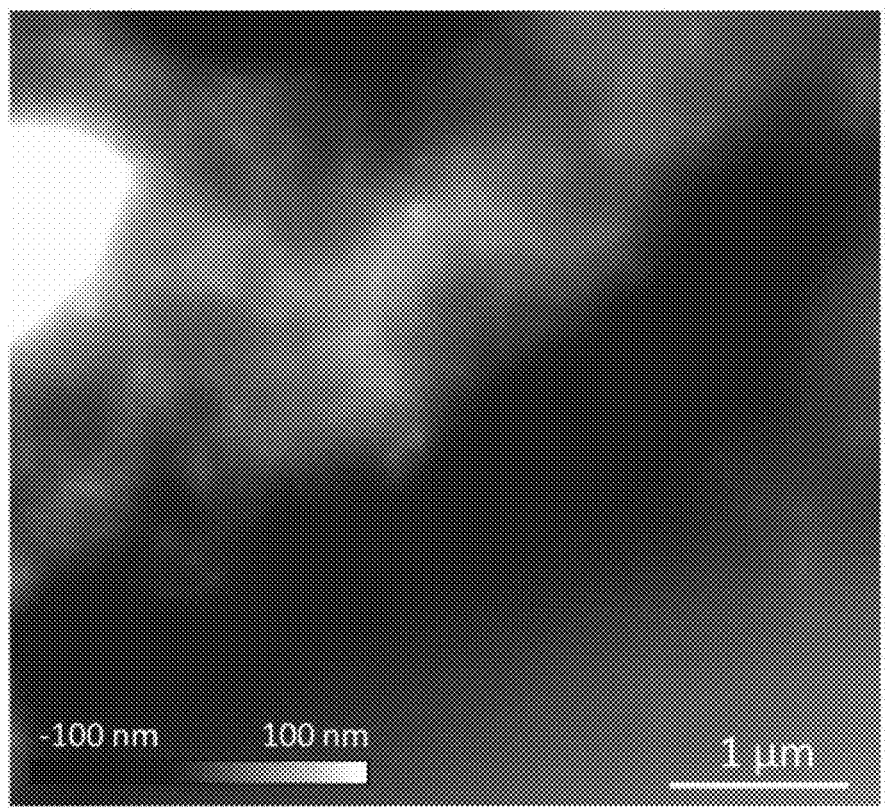
Figure 13B:
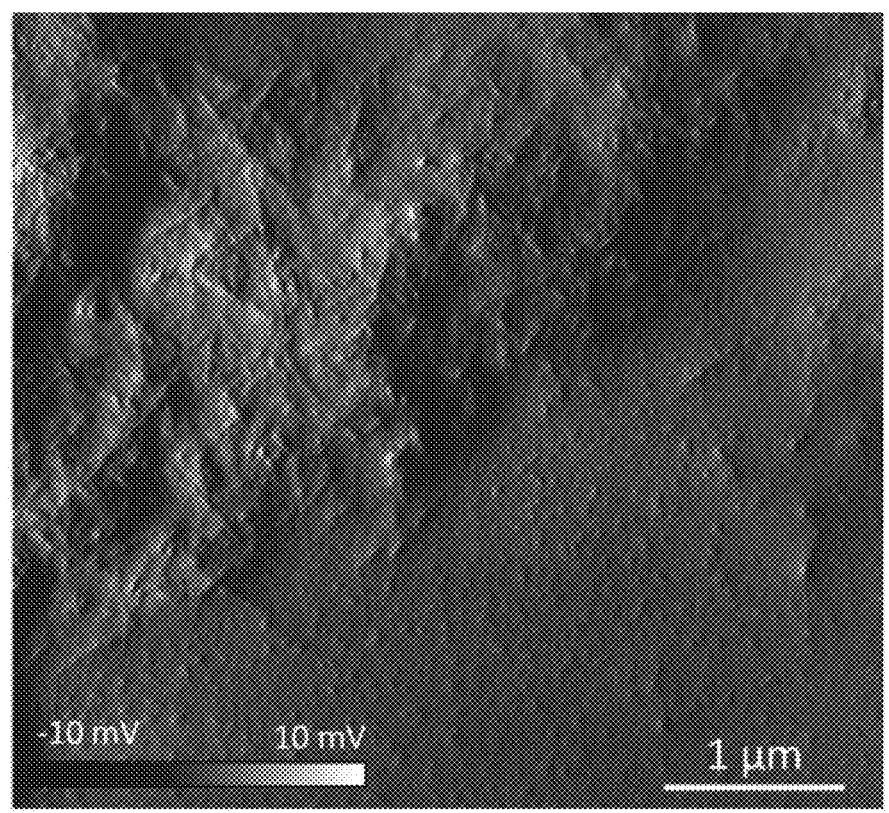

Furthermore, as shown in FIGS. 13A and 13B, a close-up by AFM of a CNC-mycelium hybrid hyphae shows nanocrystalline elements, apparently integrated within the external hyphal cell wall, and no CNCs discernible outside of the hyphae. Similar images were obtained for a CNF-mycelium hybrid, but CNFs were less clearly visualized; perhaps as it is more flexible and thinner than CNCs.

Three features stand out from the AFM: (1) CNF was absent from the areas around the hyphae, (2) EPS content appears to be higher in pure *T. ochracea* compared with the CNF-mycelium hybrid, and (3) the hyphae of the NC-mycelium hybrid dry to a more collapsed state. The first observation reinforces and extends the POM data discussed hereinabove, where the CNFs were observed only in close association to the mycelial network, but did not conclusively demonstrate the distribution of nm-scale CNFs too small to be visualized by optical microscopy. These nm-scale CNF fractions, which constitute most of the CNFs, are easily visualized by AFM, and yet were not observed in the areas surrounding the hyphae, further suggesting that they are somehow incorporated within the hyphae. Moreover, CNCs integrated within the hyphal walls was observed. This conclusion is also strongly supported by the XPS data, which did not detect exposed CNFs in the bio-composites.

The second AFM observation of an apparently denser EPS network in pure *T. ochracea* (FIG. 12E) is also supported by the HR-SEM images of the pellets (FIGS. 4A-C), where a fine intracellular EPS mesh covers the *T. ochracea* hyphae but is less pronounced in the hybrid pellets. As mentioned in the introduction, similarly to pellet formation [Gibbs et al., *Crit Rev Biotechnol* 2000, 20:17-48], EPS formation depends on many incubation-related factors, including substrate content (carbon and nitrogen sources), temperature, pH and incubation duration [Bolla et al., *Int J Biotechnol Mol Biol* 2010, 1:15-21; Tavares et al., *World J Microbiol Biotechnol* 2005, 21:1499-1507; Ma et al., *Front Microbiol* 2019, 10:2306]. EPS can be consumed in the later stages of fungal growth as a strategy to accumulate carbon and mass [Bolla et al., *Int J Biotechnol Mol Biol* 2010, 1:15-21], but at the same time EPS secretion is hindered by denser hyphal cell walls [Ma et al., *Front Microbiol* 2019, 10:2306].

To further address these aspects, determination of mass balance on a dry weight basis was conducted on selected co-incubation samples.

As shown in Table 2, the presence of carboxymethylated CNFs was associated with increased amounts of mycelial mass (hyphae+secreted matter); whereas CNCs, enzymatic CNFs, and pulp fibers were not associated with such an increase.

These results suggest that carboxymethylated CNFs encourage mycelial mass growth. As previously mentioned, the growth conditions employed in this work suppress cellulolytic enzymes and thus the increased yield is thought to be unrelated to CNF digestion. Instead, the higher yield with carboxymethylated CNFs may be related to EPS digestion or to the diversion of resources toward mycelium development due to diminished EPS secretion, or to some unknown mechanism, although some variability within co-incubations, even between sample replicates, is observed. CNCs, enzymatic CNFs, and pulp fibers do not seem to have the same impact on mycelial development as carboxymethylated CNFs, perhaps indicating a synergism between carboxymethylated CNFs and *T. ochracea* mycelium, which may be related to the carboxymethyl functionality per se or to the presence of non-crystalline carboxymethylated cellulose chains at the CNF surfaces.

TABLE 2

Mass balance for *T. ochracea* and NC-mycelium hybrids produced by co-incubation of *T. ochracea* with CNFs (DS 0.1, 1 p grade), CNCs, enzymatic CNFs, or pulp fibers (total solids determined for mixtures following autoclaving, dialysis, and homogenization).

| *T. ochracea* incubation | Total solids (grams) | NC mass (grams) | Mycelial mass (grams) | NC content | Mycelial content |
|---|---|---|---|---|---|
| pure | 2.1 | 0 | 2.1 | 0% | 100% |
| +0.25% CNF | 4.8 | 1.5 | 3.3 | 31% | 69% |
| +0.25% CNF (repeat) | 6.2 | 1.5 | 4.7 | 24% | 76% |
| +0.5% CNF | 6.1 | 3 | 3.1 | 50% | 50% |
| +0.25% CNC | 3.6 | 1.5 | 2.1 | 42% | 58% |
| +0.25% enzymatic CNF | 3.8 | 1.5 | 2.3 | 39% | 61% |
| +0.25% pulp fibers | 3.2 | 1.5 | 1.7 | 46% | 54% |

Cryo-scanning electron microscopy (cryo-SEM) and nano-indentation measurements were used to further investigate the hyphae height variation observed by AFM, where *T. ochracea* hyphae presented flat regions and elevated regions, whereas the hyphae in a mycelium-NC hybrid appeared uniformly flat upon drying.

Figure 14A:
Figure 14B:
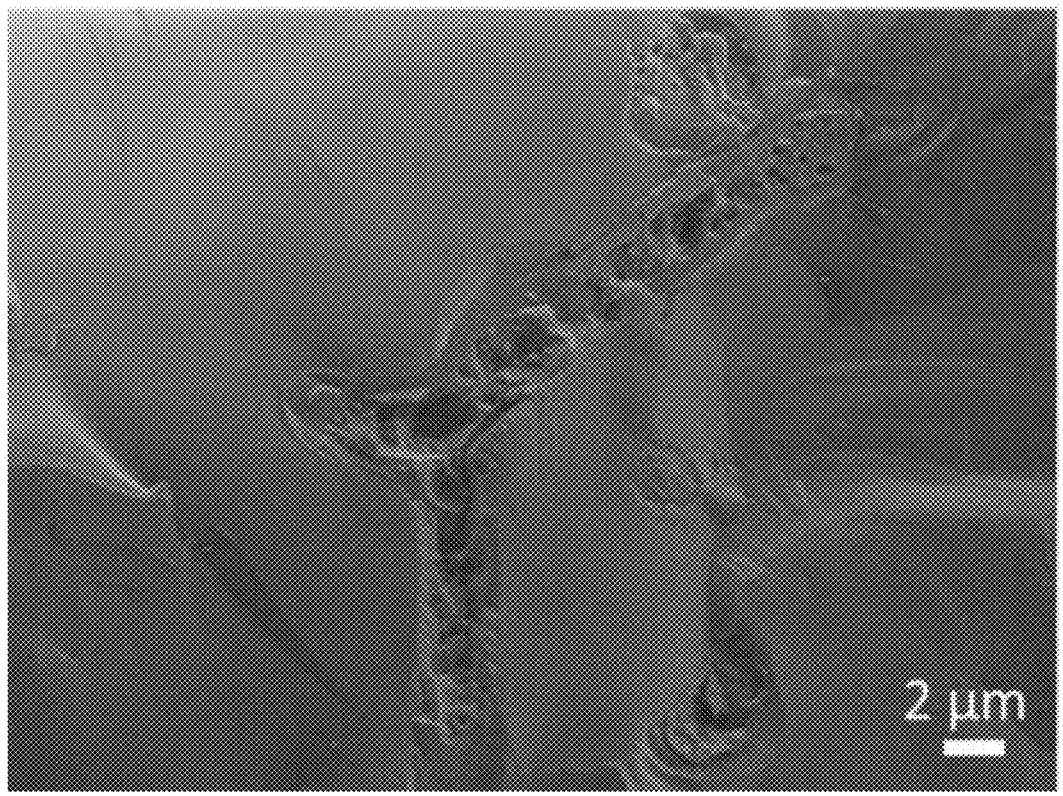
Figure 15A:
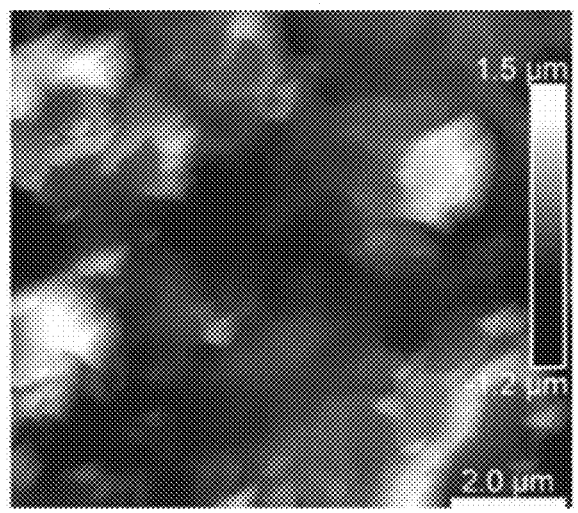
Figure 15B:
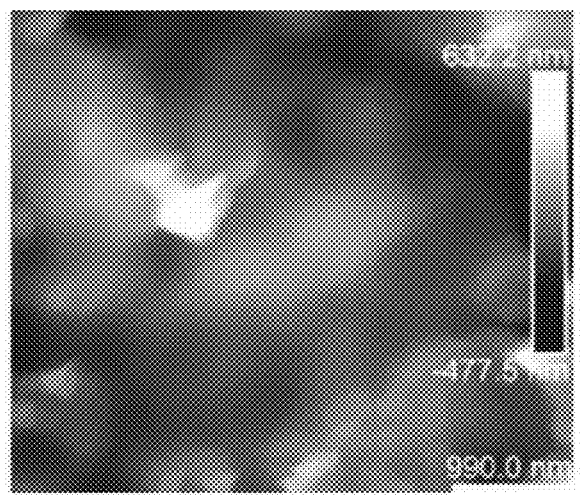
Figure 15C:
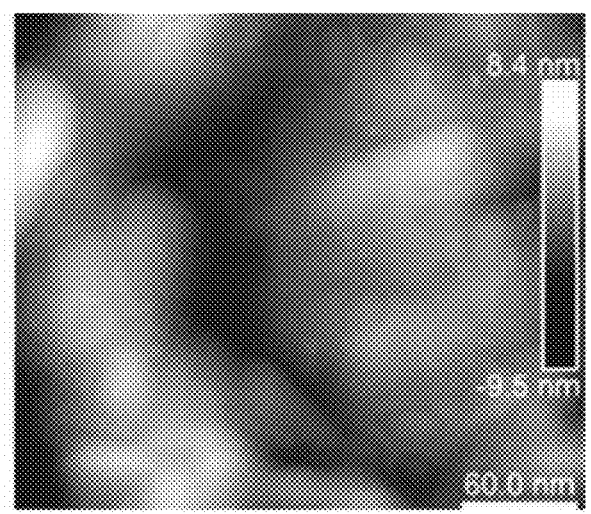
Figure 15D:
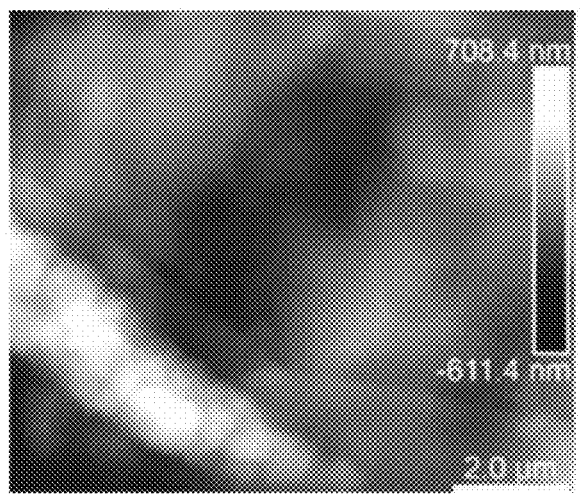
Figure 15E:
Figure 15F:
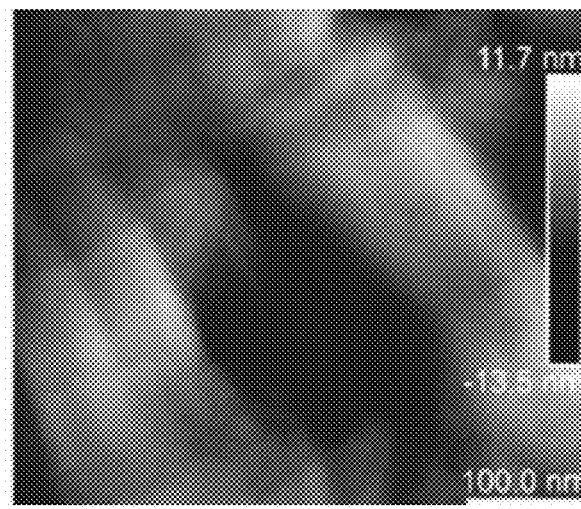
Figure 16A:
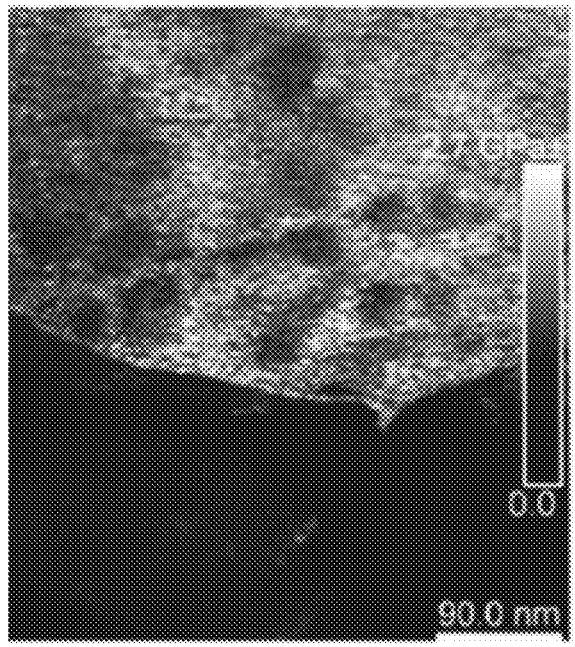
Figure 16B:
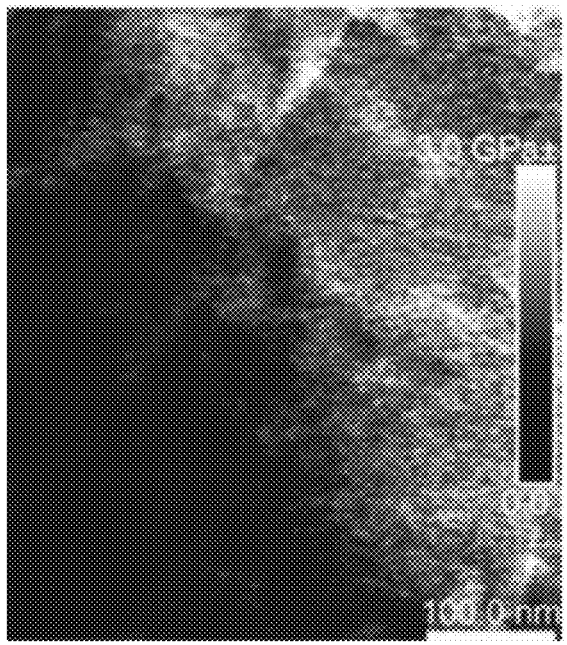
Figure 16C:
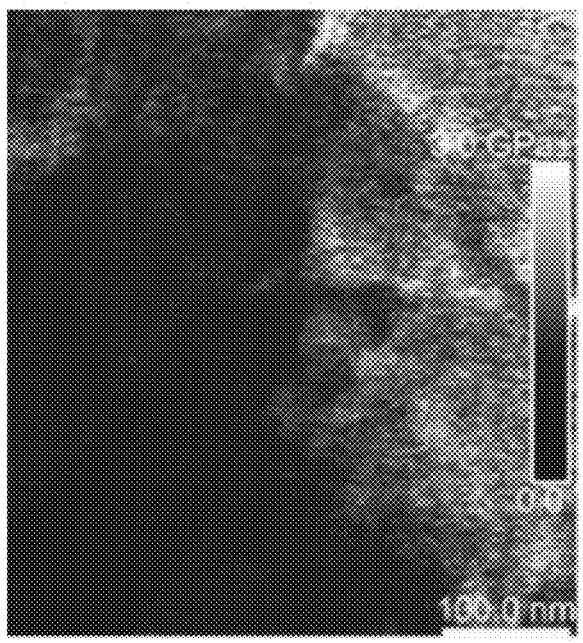
Figure 16D:
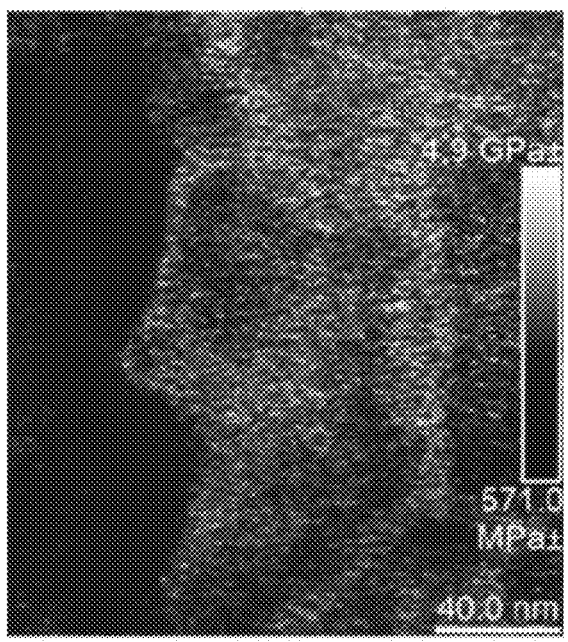
Figure 16E:
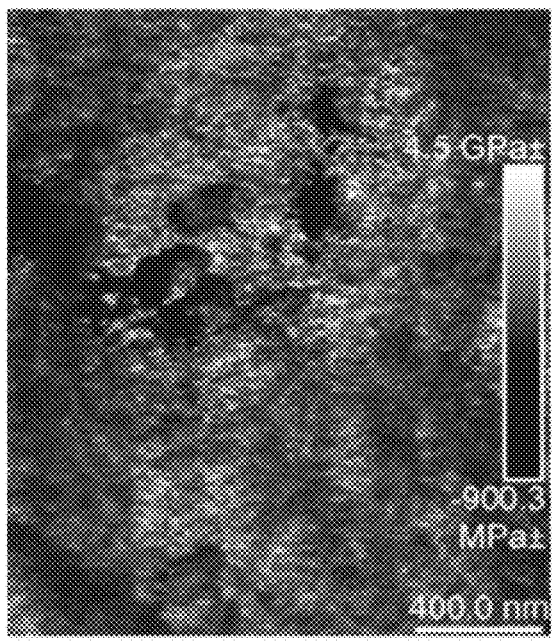
Figure 16F:
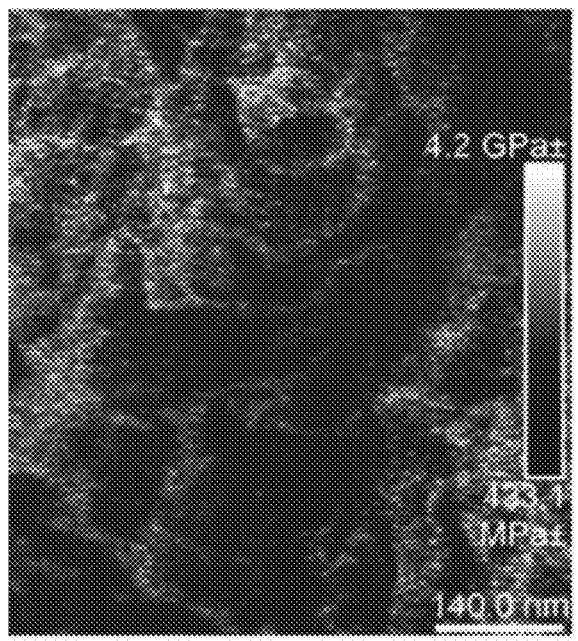

As shown in FIGS. 14A and 14B, typical organelle structures were observed by cryo-SEM within both the hyphae of *T. ochracea* (FIG. 14B) and the hyphae of the hybrid (FIG. 14A).

These results suggest that differences in cell wall properties are responsible for variations upon drying.

Without being bound by any particular theory, it is believed that introduction into the hyphal cell wall of CNFs densifies and stiffens the cell wall, such that upon drying, it may flatten the organelles, to give a more uniformly collapsed structure; whereas the pure *T. ochracea* cell wall, in the absence of NC reinforcement, is less rigid (and perhaps thinner) and better able to conform to the shape of the underlying organelles. It is further believed that the stiffer hyphal cell wall may be responsible for the apparent uniformity of the hybrid hyphae (e.g. as observed in FIG. 4C), which present fewer buckled and kinked features compared to the pure mycelium.

Representative topography and phase images associated with roughness measurements are presented in FIGS. 15A-15F; and representative nanomechanical mapping images, used to determine elastic modulus, are presented in FIGS. 16A-16F.

The roughness and elastic modulus of films formed from pure mycelium and mycelium-CNF hybrid are summarized in Table 3.

TABLE 3

Roughness at different size scales, and elastic modulus, as determined by nanomechanical mapping, of films formed from *T. ochracea* with or without co-incubation with carboxymethylated CNFs (CNF + *T. ochracea* has CNF dry content of about 30%).

| | 10 × 10 µm Ra (nm) | 5 × 5 µm Ra (nm) | 0.3 × 0.3 µm Ra (nm) | Elastic modulus (GPa) |
|---|---|---|---|---|
| *T. ochracea* | 268 | 110 | 1.9 | 1.6 ± 0.6 |
| CNF + *T. ochracea* | 135 | 53 | 3 | 2.3 ± 0.2 |

As shown in Table 3, the CNF-mycelium hybrid is less rough than pure mycelium at the micrometer scale, but that both exhibit similar roughness values at the nanometer scale (300×300 nm scan).

These results indicate that the more uniform hyphae, with fewer height variations, observed upon co-incubation of mycelium with CNFs (e.g., as shown in FIGS. 4A-4C and 12A-12F) are associated with smoother films upon formation of films from the mycelial material.

As shown in Table 3, the elastic modulus of the CNF-mycelium bio-composite film was 44% greater than that of the pure mycelium film.

These results indicate that CNFs remain intact within the hybrid, likely within the fungal cell wall, where they exert a mechanical strengthening effect (as occurs for other materials filled with NC). The coverage of NC by mycelium in the co-incubation process may reduce interface incompatibilities and may provide a promising NC modification approach for its incorporation as a strengthening additive in mycelium materials. The increased stiffness of the hybrid bio-composite is apparently sufficient to collapse the hyphae into comparatively flat, entangled ribbon-like structures upon drying. Finally, the relatively low standard deviation associated with the elastic modulus of the CNF-containing hybrid may reflect an overall compositional uniformity and the homogeneous distribution of NC.

White rot fungi, such as *T. ochracea*, are known for their ability to bind metal ions from the environment, a trait that is widely utilized for bioremediation [Osinska-Jaroszuk et al., *World J Microbiol Biotechnol* 2015, 31:1823-1844], but also for the in situ growth of metal and mineral ions into nanostructures [Livne et al., *J Mater Chem B* 2019, 7:5725-5731; Vigneshwaran et al., *Colloids Surfaces B Biointerfaces* 2006, 53:55-59; Prusinkiewicz et al., *Analyst* 2012, 137:4934-4942]. The interactions between the ions and the mycelium is apparently electrostatic, with positively charged ions binding to negative surface sites in the cell wall and associated EPS, but as the NC used is negatively charged (or basically uncharged for enzymatic CNFs and pulp fibers)—and furthermore, as charge effects are likely screened due to the high electrolyte content of the growth media—electrostatics are probably not the main factor involved in NC incorporation described herein. Instead, the interactions between NC and mycelium may be mediated by other binding interactions, perhaps the same interactions that bind mycelium to cellulose substrates in general. For example, fungi can bind to cellulose via carbohydrate binding modules (CBMs) [Baldrian & Valaskova, *FEMS Microbiol Rev* 2018, 32:501-521; Gaulin et al., *J Cell Sci* 2002, 115:4565-4575]. Previous studies have used the interactions between CBMs and cellulose to bind specific recombinant proteins to CNCs via a CBM, producing CNC-protein hybrid materials [Verker et al., *Cellulose* 2014, 21:4369-4379; Rivkin et al., *Ind Biotechnol* 2015, 11:44-58; Meirovitch et al., *Int J Mol Sci* 2016, 17:1573]. In the current study, NC becomes completely covered with mycelium during co-incubation, with the nano-fraction interwoven within the polysaccharide layers of the external hyphal cell wall and larger fibril fragments engulfed in mycelium, similar to what occurs with other micro- or macro-substrates, such as saw dust, woodchips, and pulp fibers, a general observation that supports a specific affinity between NC and mycelium.

In addition, as shown in FIG. 17, undiluted mycelium-CNF hybrids are stable as a function of time, with solid contents of 0.41-0.96% by weight; whereas diluted (0.1% by weight) mycelium-CNF hybrids exhibit significant an increase in turbidity (measured at 550 nm) over time, associated with sample phase separation which yields an upper water phase and a lower, densified phase.

These results indicate that mycelium-NC hybrids resist dilution, with a water phase forming above the diluted material.

In summary, the co-incubation approach described hereinabove used in this work proceeded via the production of mycelium pellets surrounded by a polysaccharide-rich broth, where the content and overall yield of the bio-composite are influenced by the presence of NC, and where NC was found to be concentrated within the hyphal cells and depleted from the liquid media surrounding the pellets. In this way, a nature-directed self-assembled bio-composite comprised of NC and mycelium intimately integrated into what is effectively a single cohesive material was obtained. After dialysis and homogenization, the bio-composite consisted of a uniform liquid mass comprised of a network NC-enriched mycelium structure (see, e.g., FIGS. 6B and 9A-9D), which resisted dilution.

Example 2

Figure 18A:
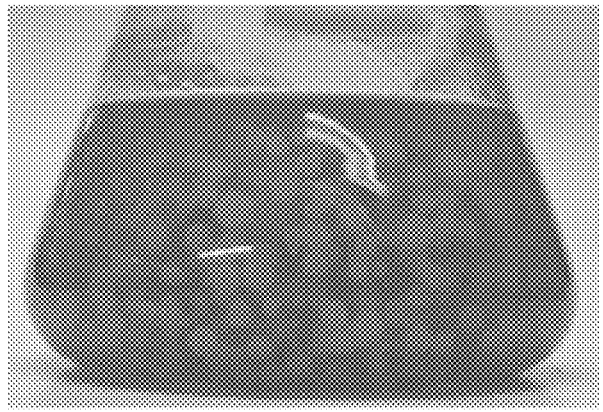
Figure 18B:
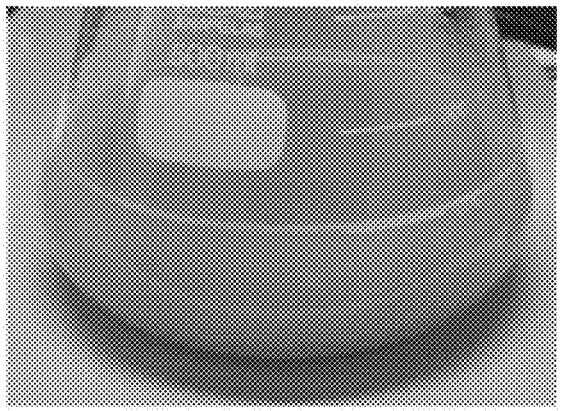
Figure 18C:
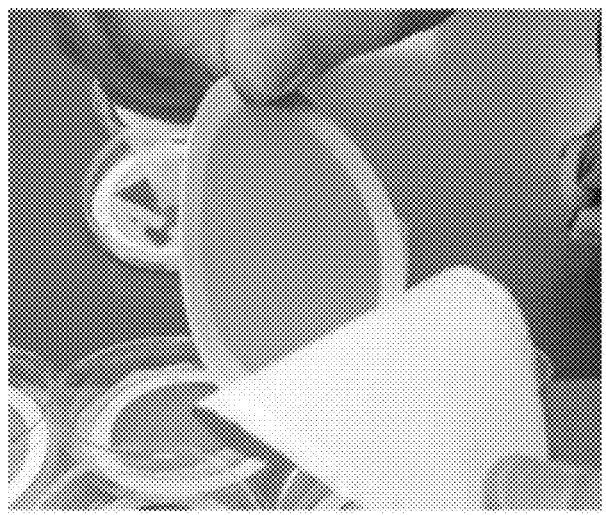
Figure 18D:

Chemical and Physical Properties of Exemplary Materials Obtained by Co-Incubation of Mycelium with Nanocellulose Following co-incubation of mycelium and nanocellulose, as described in Example 1, cultures were processed according to procedures depicted in FIG. 18A-18D. Pellets obtained as described hereinabove (FIG. 18A) were autoclaved, dialyzed, and homogenized into liquid suspension and diluted with deionized water to reach a desirable concentration (FIG. 18B). In order to prepare films, a semi-industrial paper-making vacuum-filtration system with designated filters was used. The films were dried overnight at 23° C., at a 50% relative humidity, and removed from the filter to obtain the film (FIG. 18C). Alternatively, the sample was subjected to freeze-drying, resulting in an aerogel (FIG. 18D).

These bio-fabrication processes indicate that various materials can be obtained by a sustainable production method with industrial scalability and applicability.

In order to compare the effects of co-incubation of mycelium and nanocellulose with simple admixture of mycelium and nanocellulose, similar films were prepared by mixing controlled quantities of NC into homogenized pre-grown mycelium pellets.

Figure 19A:
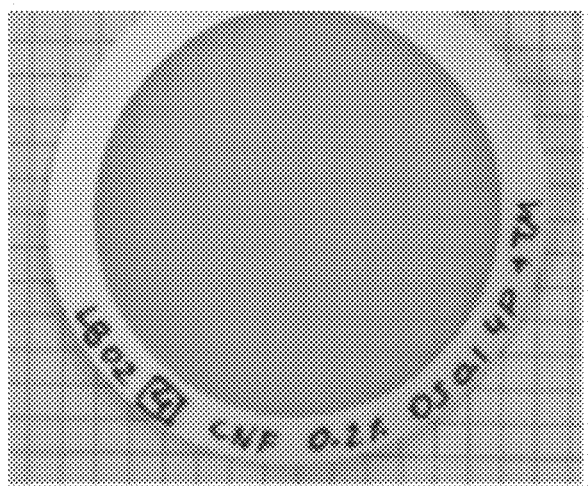
Figure 19B:
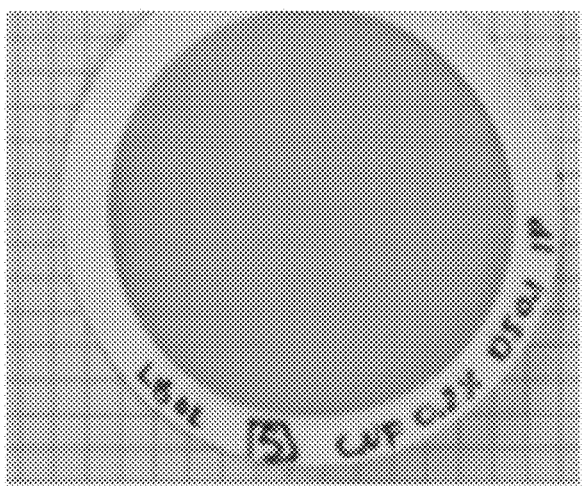
Figure 19C:
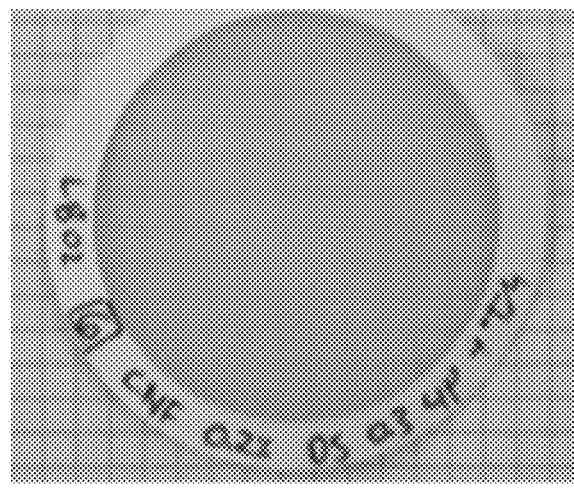
Figure 19D:
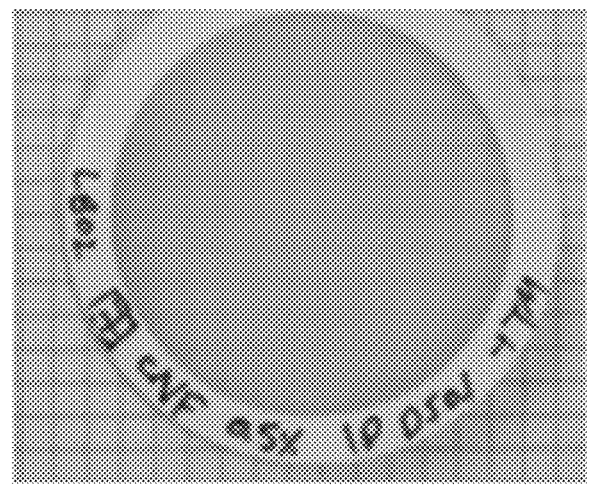
Figure 19E:
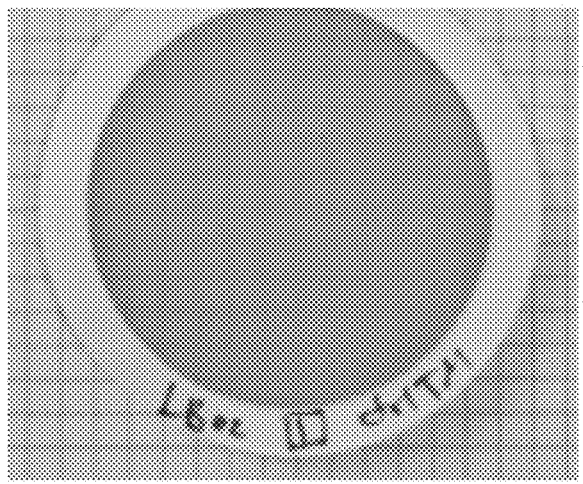
Figure 19F:
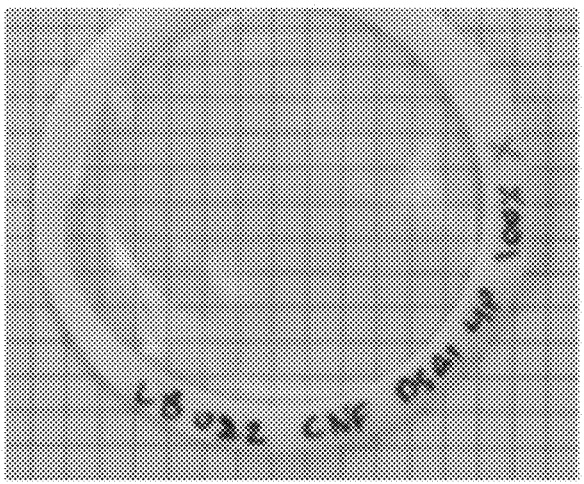
Figure 19G:
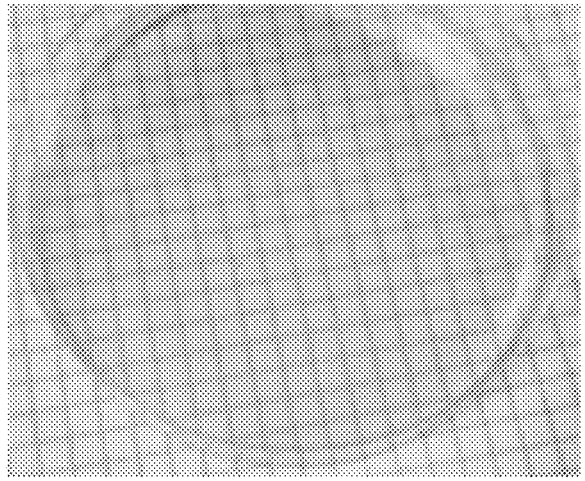
Figure 19H:
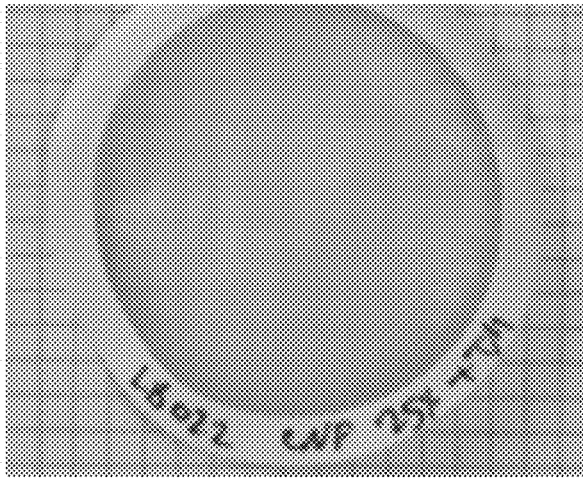
Figure 19I:
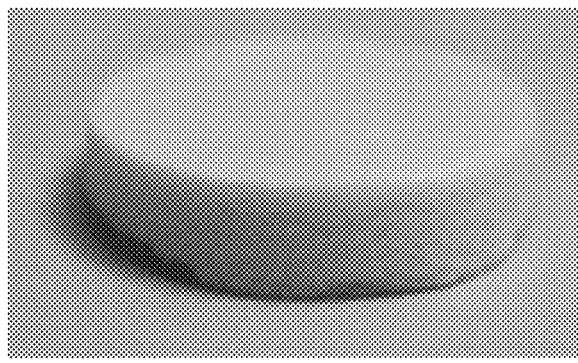

As shown in FIGS. 19A-19H, the various exemplary films (FIGS. 19A-19D and 19G) prepared from mycelium-NC hybrid material (prepared as described hereinabove) had a fine and uniform appearance, with a matte semi-opaque light brown color, similar to that of film prepared from pure mycelium (FIG. 19E), but softer in color and more transparent; whereas films formed from a simple (post-incubation) mixture of mycelium and nanocellulose (FIG. 19H) were more wrinkled, not homogeneous, and reflected the glossiness of pure CNF film (FIG. 19F). The different CNF types in various exemplary hybrid films resulted in a consistent appearance, with slight variations in color and texture, suggesting a tunable color scheme that can indicate material content or performance.

Figure 19J:
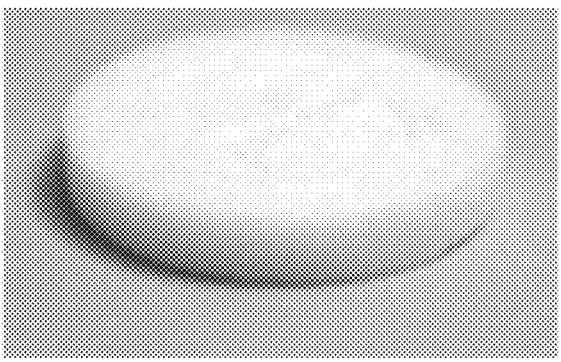
Figure 19K:
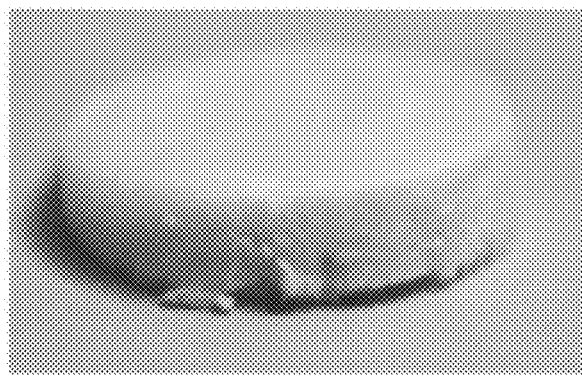
Figure 19L:
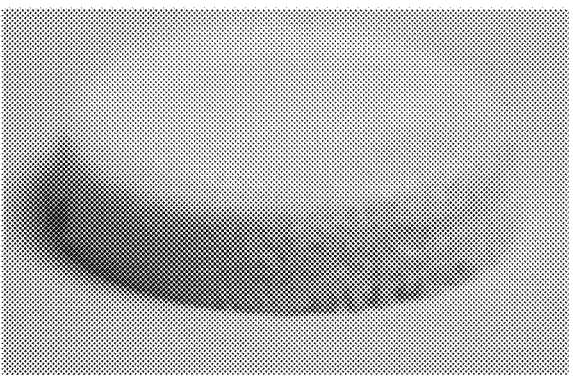

Similarly, as shown in FIGS. 19I-19L, exemplary aerogels prepared from mycelium-NC hybrid material (FIGS. 19K and 19L) had a similar, light brown appearance to aerogel prepared from pure mycelium (FIG. 19I), and differed strongly in appearance from aerogel prepared from pure CNFs (FIG. 19J).

The exemplary films were further characterized by a variety of techniques, such as tensile testing (of dry material), determination of water uptake and water contact angle to assess hydrophilicity and behavior in a wet environment, and examination of the structure of films by scanning electron microscopy (following tensile testing) with particular focus on the cross-section exposed during tensile testing.

Figure 20A:
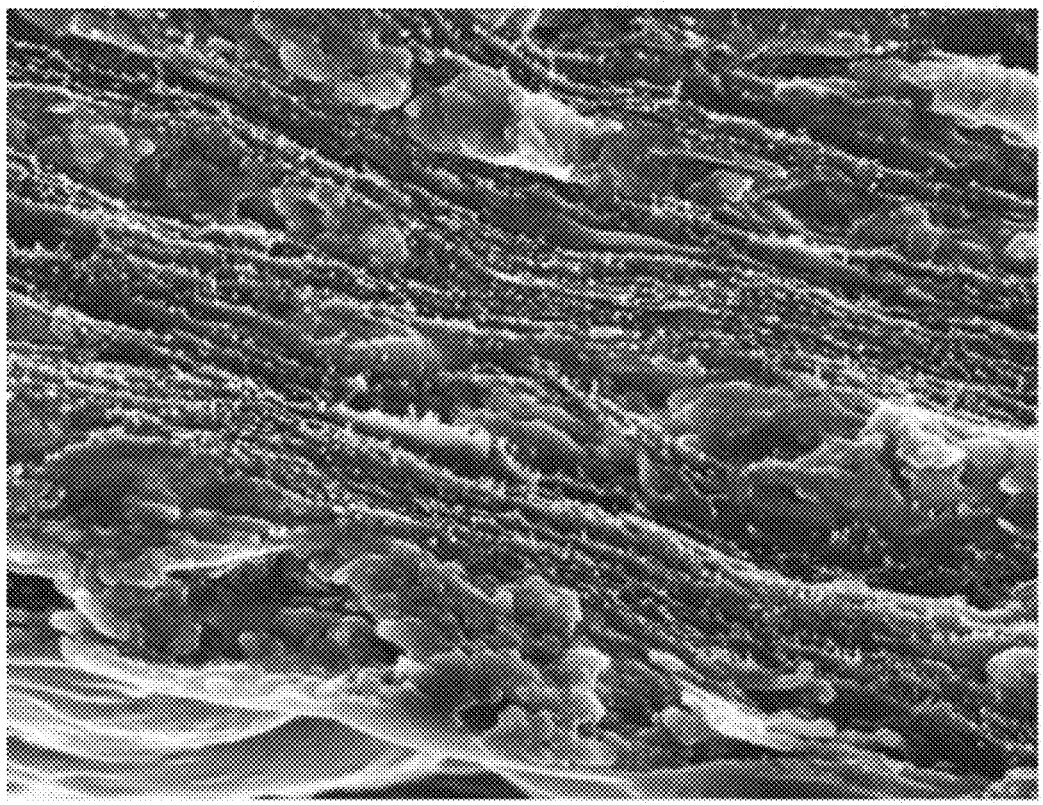
Figure 20B:
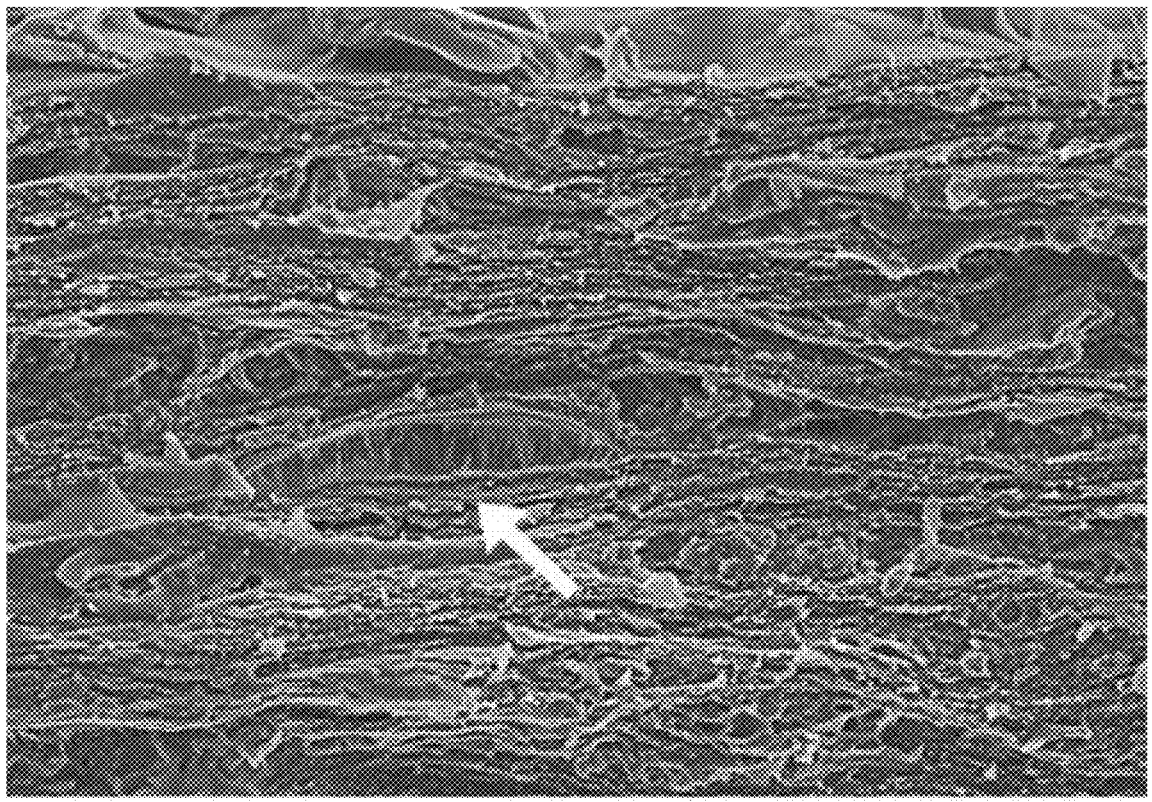

As shown in FIGS. 20A and 20B, films comprising mycelium and CNFs exhibited more exposed CNF and more air pockets when prepared from CNFs mixed with mycelium post-incubation (FIG. 20B) than when mycelium was incubated with CNFs (FIG. 20A), as determined by scanning electron microscopy.

Figure 20C:
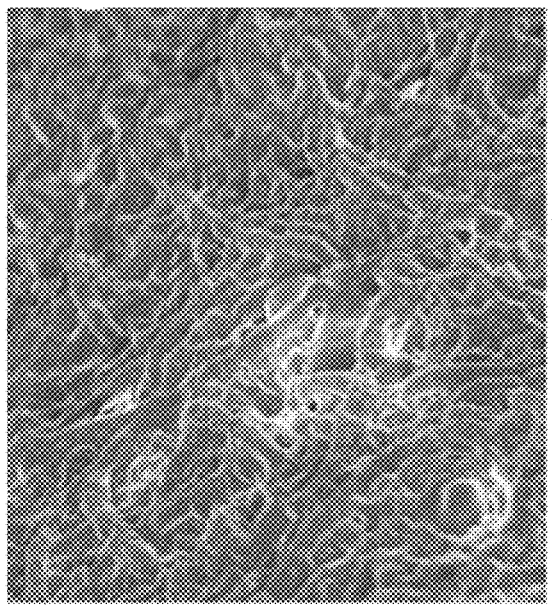
Figure 20D:
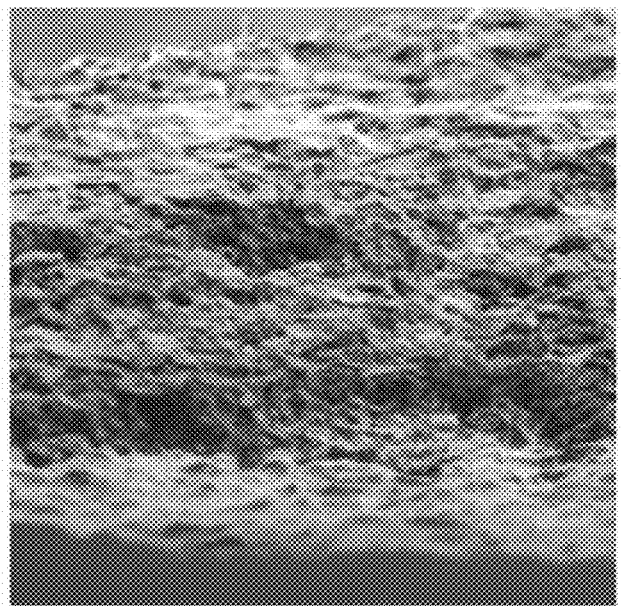
Figure 20E:
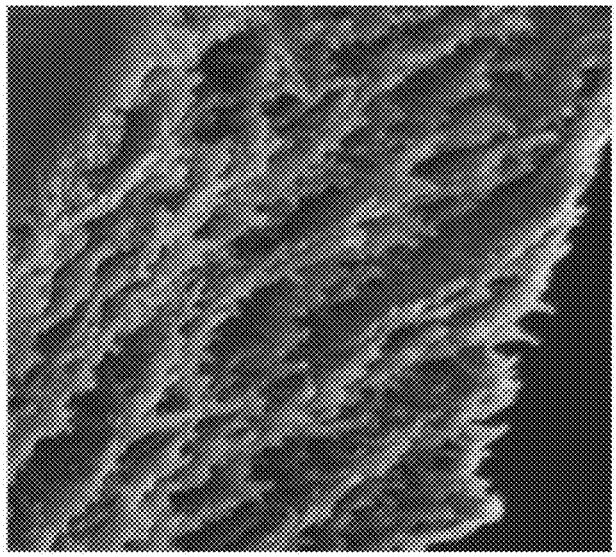
Figure 20F:
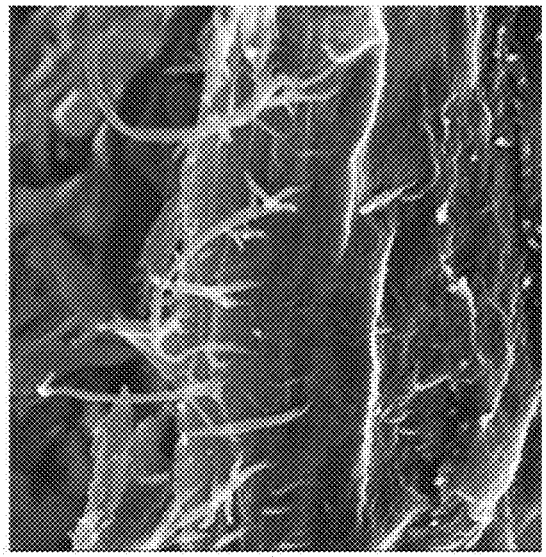

In addition, as shown in FIG. 20F, upon tearing, an exemplary mycelium-CNF hybrid material film exhibited exposed CNFs interwoven with clumps of mycelium at the rupture surface, indicating that the CNFs are fully covered by the mycelium (similarly to fibers bound by resin in a composite material).

In comparison, as shown in FIGS. 20C-20E, a pure mycelium film was characterized by 2 μm hyphae observable on the upper surface (FIG. 20C), with the cross-section having the appearance of an amorphous bulk without nanofibrils (FIG. 20D); whereas the cross-section of pure CNF films exhibited a layered formation of clearly distinct fibers (FIG. 20F), and a smooth upper surface.

Figure 21A:
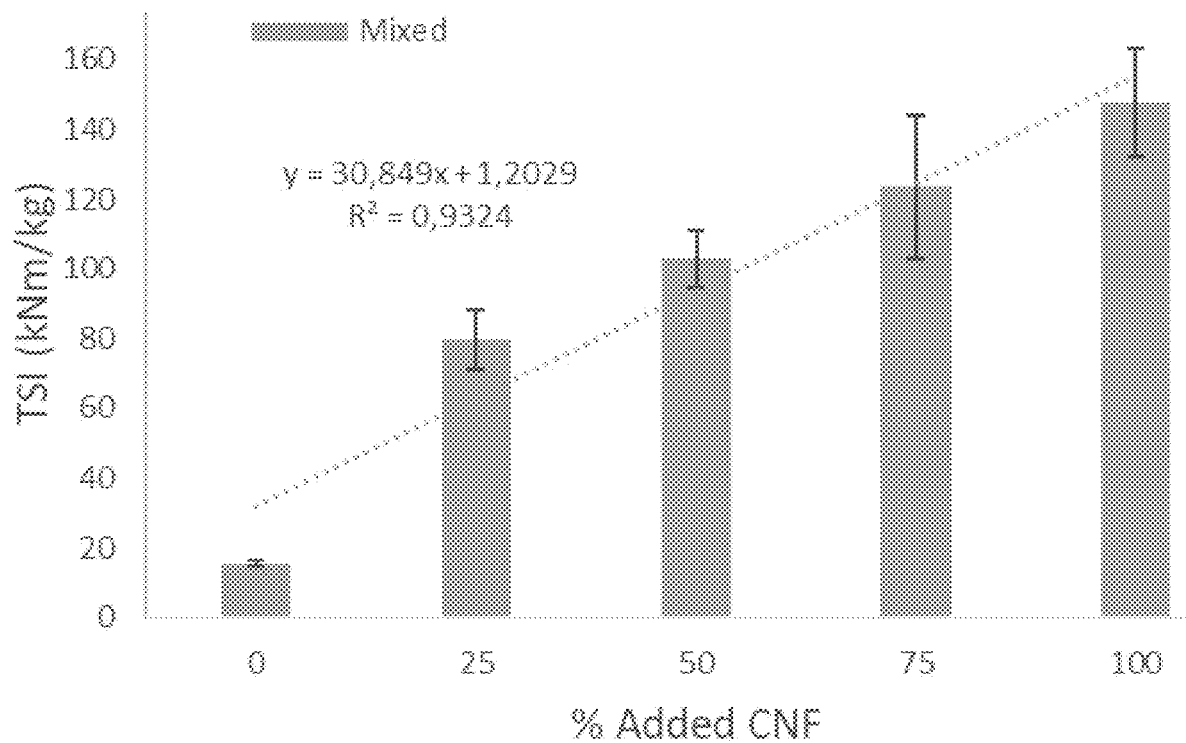
Figure 21B:
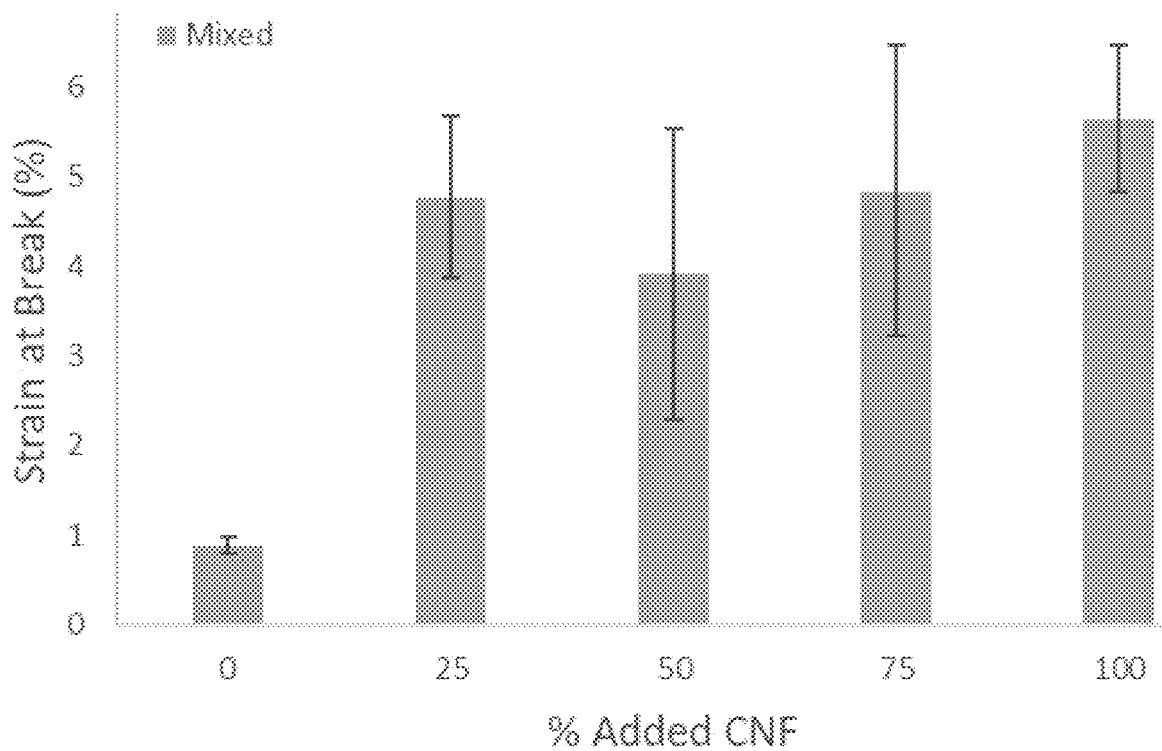
Figure 21C:
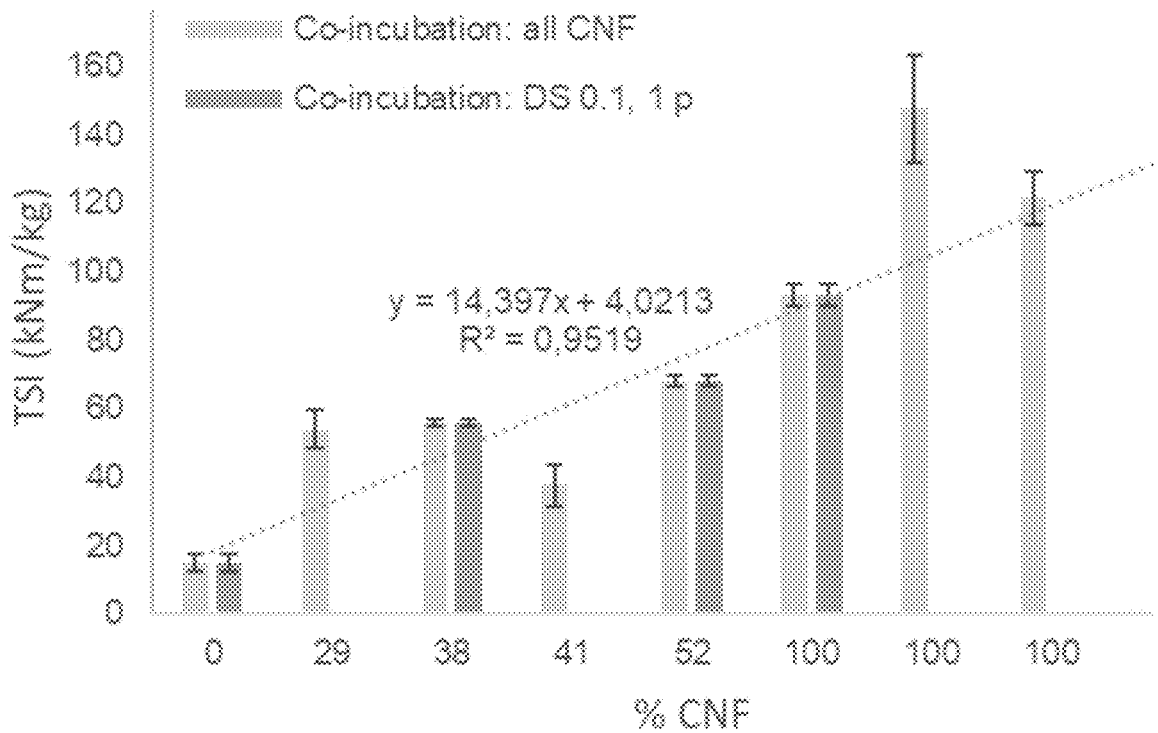
Figure 21D:
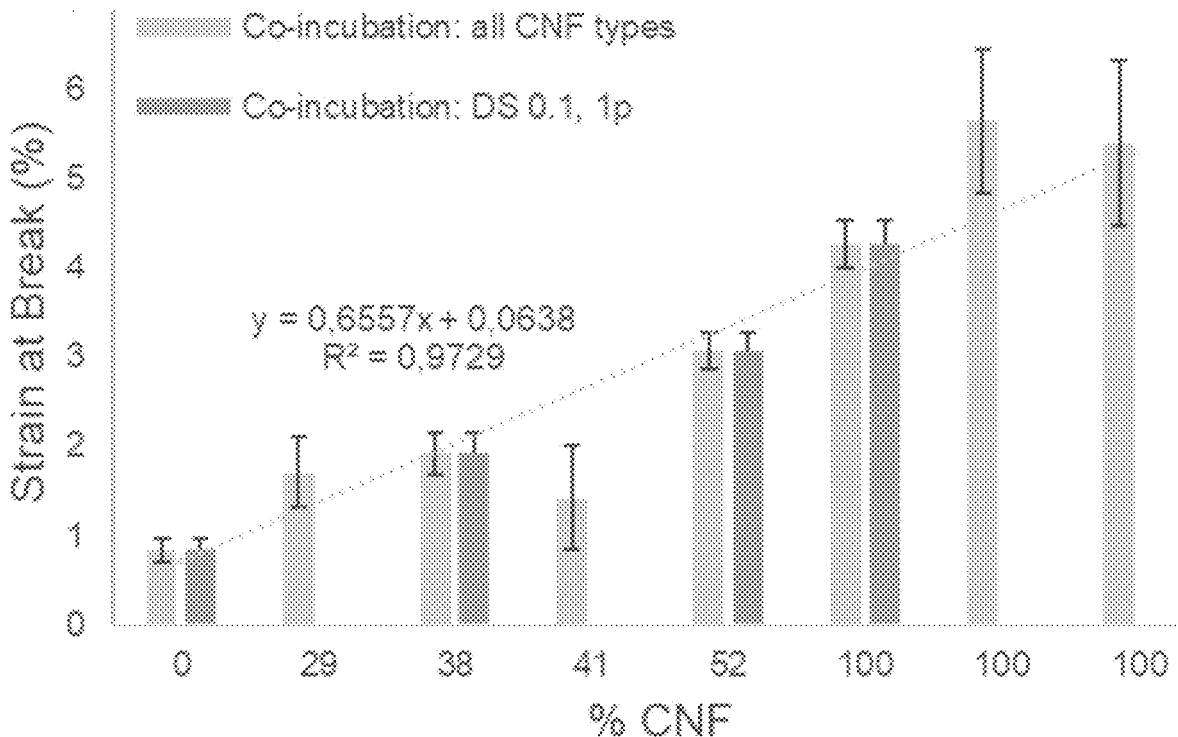

As shown in FIGS. 21A-21D, CNFs enhanced both tensile strength (FIGS. 21A and 21C) and strain at break (FIGS. 21B and 21D) of mycelium to a degree correlated with the amount of CNFs, whether the CNFs were co-incubated with mycelium (FIGS. 21C and 21D) or simply mixed with mycelium post-incubation (FIGS. 21A and 21B).

Upon contact with water, the DS 0.3, 4p grade CNFs almost totally dissolved after 30 minutes; whereas DS 0.1, 1p grade CNFs absorbed about 13,000% by weight of water, but also gradually dissolved from the start, and even gentle damping destroyed its structure so there was free water on the surface that probably resulted in an overestimate of actual absorption. DS 0.1, 4p grade CNFs absorbed less water than the other CNF types, and was more stable when wet, but started dissolving after 90 minutes.

In contrast, pure mycelium films did not swell, and maintained their structure underwater for over a month. When removed from the water, the film immediately folded, but reopened when returned to water.

The exemplary mycelium-NC hybrid films exhibit similar water uptake properties to those of pure mycelium films; the hybrid films maintained a stable structure and did not dissolve in water, and the structure did not collapse upon removal from water.

Figure 22A:
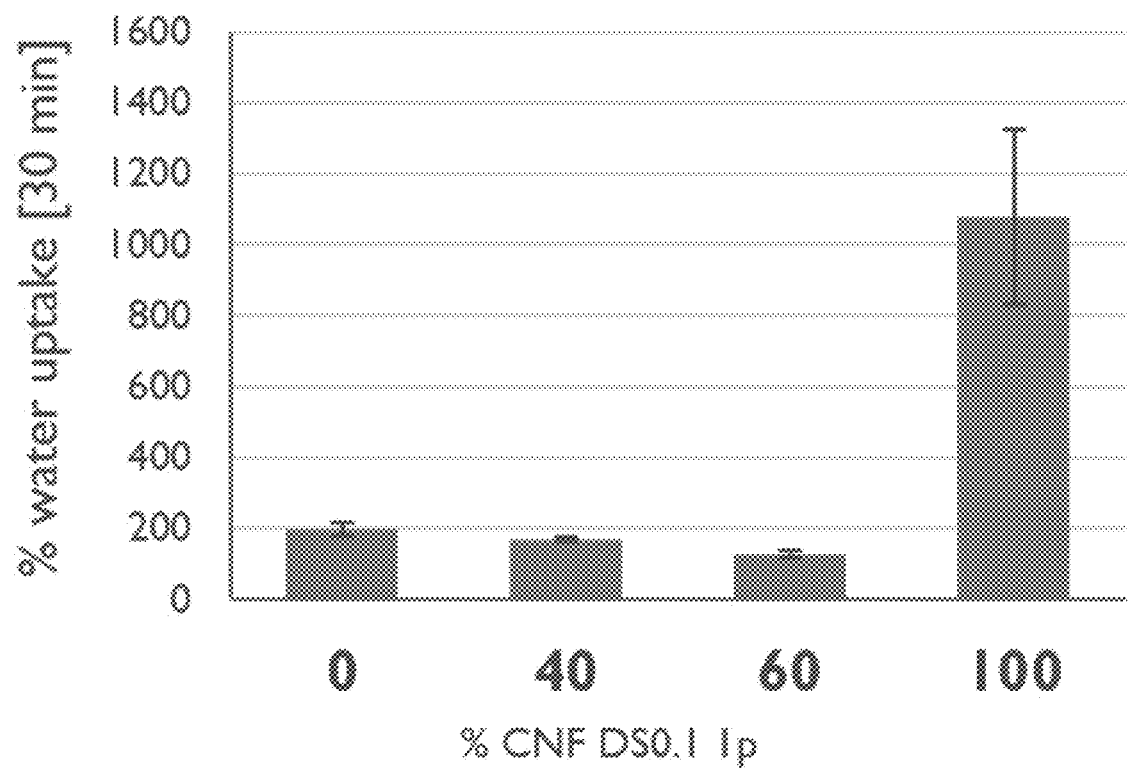
Figure 22B:
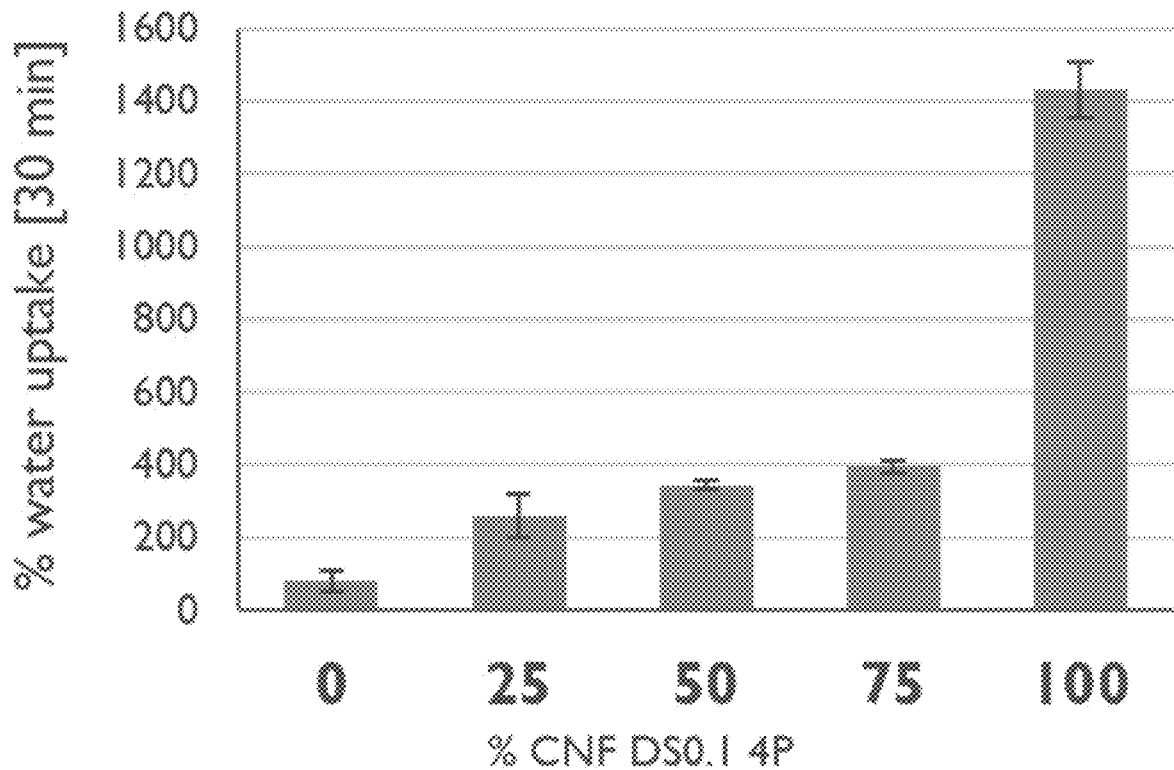
Figure 23A:
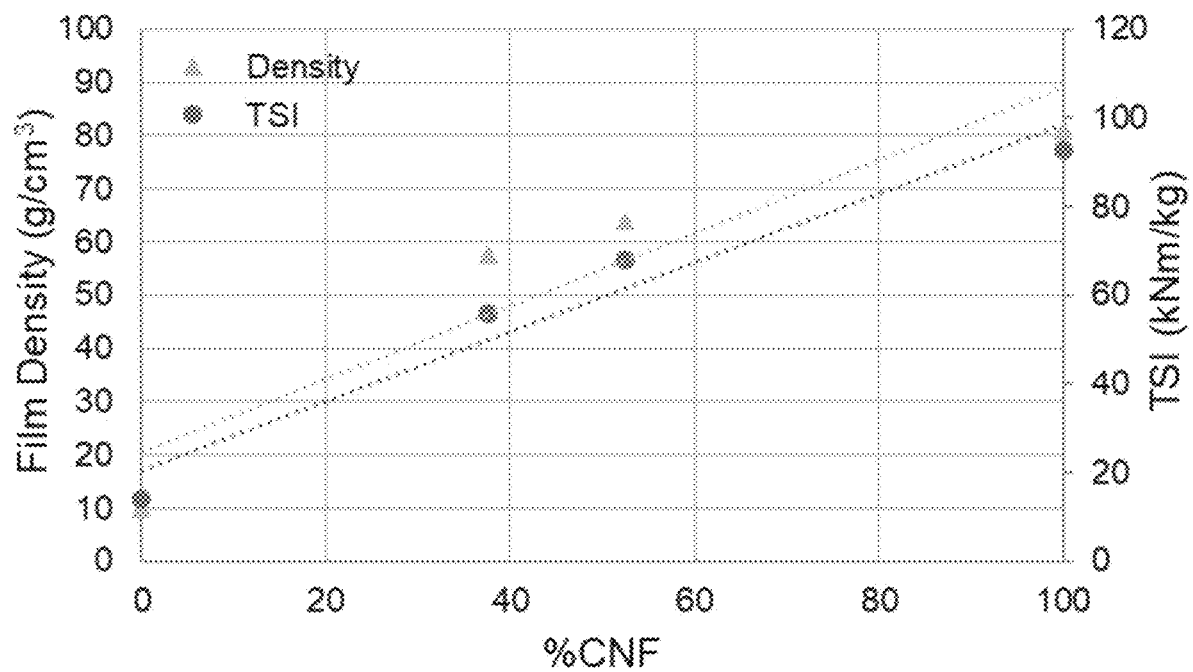
Figure 23B:
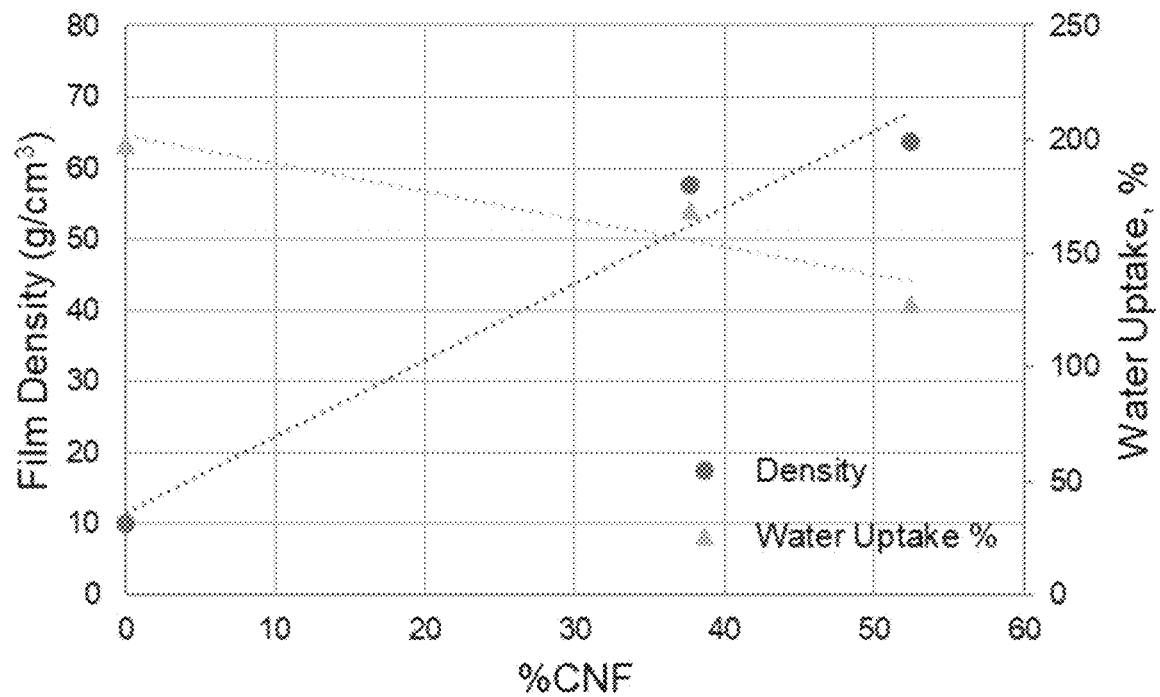

As shown in FIGS. 22A-23B, CNF content of exemplary hybrid materials was negatively correlated with water uptake (FIGS. 22A and 23B), and positively correlated with density (FIGS. 23A and 23B) and tensile strength (FIG. 22A); whereas proportions of CNF mixed with mycelium post-incubation was positively correlated with water uptake (FIG. 22B).

As further shown therein, pure CNF material was denser and stronger than a hybrid material containing 60% CNF (FIG. 23A), but absorbed about 10-folds more water (FIG. 22A), although the extreme swelling and dissolution of pure CNF material during the test means that the accuracy of the results was limited.

The results for pure CNF (and CNF mixed with mycelium post-incubation) are consistent with the ability of CNF to absorb considerable amounts of water between the fibers thereof. For example, The SEM images discussed hereinabove show that CNF mixed with mycelium post-incubation is not systematically bound by mycelium, and suggests that air pockets capable of trapping free water may remain abundant.

In contrast, the negative correlation between CNF content of exemplary hybrid materials and water uptake is surprising, and suggests that the mycelium alters the water absorbance properties of CNF, e.g., by filling gaps between the fibers with hydrophobic mycelium.

This phenomenon may be associated with an increased mycelium density at higher CNF content (as discussed hereinabove), and the observation that the CNFs are individually covered by mycelium and hydrophobic EPS, filling up nano-scale air pockets (as discussed hereinabove with respect to scanning electron microscopy images), limiting spaces between fibers, and consequently reducing water uptake.

In addition, without being bound by any particular theory, it is believed that the considerable difference in water uptake between post-incubation mixtures of even 75% CNFs (about 400% uptake) and pure CNFs may be due to mycelium migrating to the air interface of the film during fabrication, creating a hydrophobic exterior layer.

The similarity between water absorption of pure mycelium and mycelium-NC hybrid indicate that NC hydrophilicity is shielded by NC being covered by mycelium (e.g., suspended within a mycelium mesh).

These results suggest that mycelium-nanocellulose hybrid materials are associated with the mechanical strength characteristic of nanocellulose, and the hydrophobicity and limited water uptake and/or dissolution characteristic of mycelium upon exposure to water.

Although high water absorbance may be useful in many applications, such as healthcare, hygiene products and food packaging, maintaining integrity of the structure is commonly essential. Mycelium-nanocellulose hybrid materials can provide a combination of water absorption and structural integrity when wet.

The hydrophobicity of films prepared from exemplary hybrid materials and films prepared from CNF mixed with mycelium post-incubation was evaluated by determining static water contact angle.

As shown in FIG. 24, pure CNF films exhibited a static water contact angle of about 40°, indicative of a relatively hydrophilic material; whereas all tested films comprising mycelium and CNF exhibited a static water contact angle of about 60-70°.

These results indicate that the differences discussed hereinabove in water uptake between hybrid materials and CNF mixed with mycelium (post-incubation) cannot be explained simply by amount of hydrophobic substances in the film; and suggest that factors such as void structure may be more important.

Taken together, these results indicate that the reduced water uptake associated with CNF in exemplary hybrid materials is associated with increased density and reduction in hydrophilic voids suitable for absorbing water (e.g., as opposed to net amount of hydrophobic substances); whereas CNF mixed with mycelium post-incubation is associated with increased water uptake, suggesting that it retains hydrophilic voids (perhaps because it is more exposed).

Example 3

Exemplary Processed Materials Obtained by Co-Incubation of Mycelium with Nanocellulose Films were prepared by vacuum filtration (and ambient drying) of a hybrid material obtained by co-incubation of mycelium and nanocellulose (carboxymethylated CNFs co-incubated with mycelium at a concentration of 0.25% or 0.5%, or enzymatic CNFs co-incubated with mycelium at a concentration of 0.25%), according to procedures described hereinabove. The films were then subjected to a hot press (105° C. for 5 minutes). Pure CNF films (prepared from carboxymethylated CNFs or enzymatic CNFs) served as controls. The compositions of the films are summarized in Table 4.

The ability of films to serve as a barrier against oils—a property useful, for example, for packaging material for various products (e.g., many foods)—was determined by contacting the films with caprylic acid, a low molecular weight oil which is a good test of performance as a barrier. The caprylic acid was deposited in a circle; if after a time period of at least 24 hours, the caprylic acid did not spread, the film was deemed a good oil barrier.

All of the tested films (summarized in Table 4) were good oil barriers, as determined by the test described hereinabove.

TABLE 4

Composition of hybrid material used to prepare exemplary films

| Film composition | Solid content after incubation (% by weight) | Nanocellulose content of hybrid (% by dry weight) |
|---|---|---|
| Mycelium co-incubated with 0.25% carboxymethylated CNFs | 0.99% | 24% |
| Mycelium co-incubated with 0.25% carboxymethylated CNFs | 0.57% | 39% |
| Mycelium co-incubated with 0.5% carboxymethylated CNFs | 0.91% | 50% |

TABLE 4-continued

Composition of hybrid material used to prepare exemplary films

| Film composition | Solid content after incubation (% by weight) | Nanocellulose content of hybrid (% by dry weight) |
|---|---|---|
| Carboxymethylated CNFs (control) | N.A. | 100% |
| Enzymatic CNFs (control) | N.A. | 100% |

These results indicate that hybrid materials described herein may serve as barriers to hydrophobic substances, in addition to being more water resistant than nanocellulose (as discussed hereinabove); and may be useful, for example, as packaging materials for a variety of products.

Example 4

Material Obtained by Co-Incubation of Mycelium with Nanocellulose and Wood

Fungi (*Trametes versicolor*, *Trametes ochracea* or *Ganoderma sessile*) were incubated, at 24° C. and about 50% relative humidity, in combination with previously sterilized (at 121° C. for 15 minutes) nanocellulose (CNFs, or 2.05 or 7.9 weight % CNCs) and vine woodchips (sieved, 2 mm). After 14 days of incubation, growth was terminated by drying for 2 hours at 60'° C. Examination by optical microscopy showed an interlocking network of mycelium and woodchips.

A light-colored material with a mottled appearance was obtained using procedures such as described hereinabove. The material, comprising mycelium and woodchips, was molded to form a multi-cell tray (FIG. 25), tree protectors (FIG. 26) and root trainers (FIG. 27).

The chemical and physical properties of the obtained material are optionally determined (e.g., according to one or more technique described in Example 1 or 2), to thereby assess the effect of the nanocellulose on material; e.g., determination of incorporation of nanocellulose into the mycelium, and/or comparison of the properties of the material (e.g., in comparison to the a corresponding material without nanocellulose).

Example 5

Additional Materials Obtained by Co-Incubation of Mycelium with Cellulose or Cellulose Derivatives A hybrid material is obtained by co-incubation (according to procedures described hereinabove) of mycelium and any one or more of the following substances:
a) unmodified mechanically fibrillated nanocellulose (cellulose nanofibrils, microfibrillated cellulose and/or cellulose nanocrystals);
b) enzymatically treated cellulose nanofibrils and/or microfibrillated cellulose;
c) carboxymethylated microfibrillated cellulose;
d) oxidized (e.g., TEMPO-oxidized) cellulose nanofibrils and/or microfibrillated cellulose which comprise carboxylic acid groups;
e) cellulose nanocrystals with ionic sulfate groups at surface;
f) cellulose nanocrystals with carboxylic acid groups at surface;
g) nanocellulose (cellulose nanofibrils, microfibrillated cellulose and/or cellulose nanocrystals) with cationic groups;
h) pulp fibers;
i) regenerated cellulose fibers (e.g., rayon, viscose and/or cellophane);
j) natural cellulose fibers (e.g., from cotton); and
k) synthetic cellulose derivatives.

The chemical and physical properties of the obtained material are optionally determined (e.g., according to one or more technique described in Example 2), to thereby assess the effect of the tested substance on the properties of the material (e.g., in comparison to the nanocellulose types described in any of Examples 1-4).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A composition comprising a mycelium of a fungus and a cellulose, the composition being obtainable by a method comprising incubating said fungus in a liquid medium, said liquid medium comprising nutrients and said cellulose, wherein said cellulose is encompassed within and/or is adhered to cells of said mycelium, wherein said cellulose encompassed within and/or adhered to cells of said mycelium comprises at least 20 percent of a total dry weight of said mycelium and said cellulose, and wherein said cellulose encompassed within and/or adhered to cells of said mycelium is nanocellulose and is in a form which is at least partially resistant to digestion by the fungus.

2. A composition comprising a mycelium and a cellulose, wherein said cellulose is encompassed within and/or is adhered to cells of said mycelium, and said cellulose encompassed within and/or adhered to cells of said mycelium comprises at least 20 percent of a total dry weight of said mycelium and said cellulose, and wherein said cellulose encompassed within and/or adhered to cells of said mycelium consists of nanocellulose.

3. The composition of claim 2, wherein a water uptake of said composition is no more than 1000% of the dry weight of the composition.

4. The composition of claim 2, being in a form of a layer or a porous structure.

5. An article-of-manufacture comprising the composition of claim 2.

6. The composition of claim 1, wherein said nutrients comprise at least one monosaccharide.

7. The composition of claim 1, wherein said nutrients suppress cellulase activity of said fungus.

8. The composition of claim 1, wherein an initial concentration of said cellulose in said liquid medium is in a range of from 0.05 weight percent to 5 weight percent.

9. The composition of claim 1, wherein said method further comprises homogenizing said mycelium so as to obtain a homogenized composition comprising said mycelium and said cellulose.

10. The composition of claim 2, wherein a water uptake of said composition is no more than 200% of the dry weight of the composition.

* * * * *